US011696947B2

(12) United States Patent
Kraemer-Kuehl et al.

(10) Patent No.: US 11,696,947 B2
(45) Date of Patent: Jul. 11, 2023

(54) H52 IBV VACCINE WITH HETEROLOGOUS SPIKE PROTEIN

(71) Applicant: Boehringer Ingelheim Vetmedica GmbH, Ingelheim am Rhein (DE)

(72) Inventors: Annika Kraemer-Kuehl, Seesen (DE); Egbert Siegfried Mundt, Isernhagen (DE); Hans-Christian Philipp, Hemmingen (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 16/665,465

(22) Filed: Oct. 28, 2019

(65) Prior Publication Data

US 2020/0129614 A1    Apr. 30, 2020

(30) Foreign Application Priority Data

Oct. 31, 2018  (EP) .................................. 18203637

(51) Int. Cl.
*A61K 39/215* (2006.01)
*C12N 7/00* (2006.01)
*A61P 31/14* (2006.01)
*A61K 39/00* (2006.01)

(52) U.S. Cl.
CPC ............ *A61K 39/215* (2013.01); *A61P 31/14* (2018.01); *C12N 7/00* (2013.01); *A61K 2039/5256* (2013.01); *A61K 2039/552* (2013.01); *C12N 2770/20021* (2013.01); *C12N 2770/20022* (2013.01); *C12N 2770/20034* (2013.01); *C12N 2770/20071* (2013.01)

(58) Field of Classification Search
None
See application file for complete search history.

(56) References Cited

U.S. PATENT DOCUMENTS

2012/0177675 A1*  7/2012  Britton ................... A61P 31/16
                                                              424/186.1

FOREIGN PATENT DOCUMENTS

| CN | 103642759 A | 3/2014 |
| CN | 104694488 A | 6/2015 |
| WO | 2004078203 A2 | 9/2004 |

OTHER PUBLICATIONS

Hodgson et al. Recombinant Infectious Bronchitis Coronavirus Beaudette with the Spike Protein Gene of the Pathogenic M41 Strain Remains Attenuated but Induces Protective Immunity. Journal of Virology, Dec. 2004, vol. 78, p. 13804-13811.*
Geerligs et al. Efficacy and safety of an attenuated live QX-like infectious bronchitis virus strain as a vaccine for chickens. Avian Pathology (Feb. 2011) 40(1), 93-102.*
GenBank: ATE90980.1. spike protein [Avian coronavirus]. Dated Oct. 2, 2017.*
Casais et al. Recombinant avian infectious bronchitis virus expressing a heterologous spike gene demonstrates that the spike protein is a determinant of cell tropism. J Virol. Aug. 2003;77(16):9084-9.*
Bickerton et al. Recombinant infectious bronchitis viruses expressing heterologous S1 subunits: potential for a new generation of vaccines that replicate in Vero cells. J Gen Virol. Dec. 2018; 99(12):1681-1685. Epub Oct. 24, 2018.*
Armesto et al. A Recombinant Avian Infectious Bronchitis Virus Expressing a Heterologous Spike Gene Belonging to the 4/91 Serotype. PLoS ONE, 2011,6(8): e24352.*
GenBank: CAZ86699.1. spike protein [Infectious bronchitis virus ITA/90254/2005]. Dated Oct. 23, 2009.*
Shan, Dan, et al. "Effects of hypervariable regions in spike protein on pathogenicity, tropism, and serotypes of infectious bronchitis virus." Virus research 250 (2018): 104-113.
Zhou, Ying Shun, et al. "Establishment of reverse genetics system for infectious bronchitis virus attenuated vaccine strain H120." Veterinary microbiology 162.1 (2013): 53-61.
Ellis, Samantha, et al. "Recombinant infectious bronchitis viruses expressing chimeric spike glycoproteins induce partial protective immunity against homologous challenge despite limited replication in vivo." Journal of virology 92.23 (2018): e01473-18.
Zhou, Yingshun, et al. "The establishment and characteristics of cell-adapted IBV strain H120." Archives of virology 161.11 (2016): 3179-3187.
Wei, Yan-Quan, et al. "Development and characterization of a recombinant infectious bronchitis virus expressing the ectodomain region of S1 gene of H120 strain." Applied microbiology and biotechnology 98.4 (2014): 1727-1735.
Armesto, Maria, et al. "A recombinant avian infectious bronchitis virus expressing a heterologous spike gene belonging to the 4/91 serotype." PLoS One 6.8 (2011): e24352.
Hodgson, Teri, et al. "Recombinant infectious bronchitis coronavirus Beaudette with the spike protein gene of the pathogenic M41 strain remains attenuated but induces protective immunity." Journal of virology 78.24 (2004): 13804-13811.
Casais, Rosa, et al. "Recombinant avian infectious bronchitis virus expressing a heterologous spike gene demonstrates that the spike protein is a determinant of cell tropism." Journal of virology 77.16 (2003): 9084-9089.

(Continued)

Primary Examiner — Nianxiang Zou
(74) Attorney, Agent, or Firm — Jamie L. Graham

(57) ABSTRACT

The present invention relates i.a. to an H52 IBV (infectious bronchitis virus) encoding for a heterologous S (spike) protein or fragment thereof. Further, the present invention relates to an immunogenic composition comprising said H52 IBV encoding for a heterologous S (spike) protein or fragment thereof. Furthermore, the present invention relates to methods for immunizing a subject comprising administering to such subject the immunogenic composition of the present invention. Moreover, the present invention relates to methods of treating or preventing clinical signs caused by IBV in a subject of need, the method comprising administering to the subject a therapeutically effective amount of an immunogenic composition according to the present invention.

18 Claims, 3 Drawing Sheets

Specification includes a Sequence Listing.

(56) References Cited

OTHER PUBLICATIONS

Bickerton, Erica, Giulia Dowgier, and Paul Britton. "Recombinant infectious bronchitis viruses expressing heterologous S1 subunits: potential for a new generation of vaccines that replicate in Vero cells." Journal of General Virology 99.12 (2018): 1681-1685.
Valastro, Viviana, et al. "S1 gene-based phylogeny of infectious bronchitis virus: an attempt to harmonize virus classification." Infection, Genetics and Evolution 39 (2016): 349-364.
Van Beurden et al., "A reverse genetics system for avian coronavirus infectious bronchitis", Virology Journal,, Dec. 2017, vol. 14, No. 1, 12.
Cavanagh et al. "Variation in the spike protein to the 793/B type . . ." Avian Pathology, No. 34, No. 1, Feb. 1, 2005, p. 20-25.
Geerligs et al.; Avian Pathology; Feb. 2011; 40(1), 93-102.
Li and Yang, 2001, Avian Pathol 30, 535-541.
The Free Dictionary [Internet] "heterologous protein". Farlex Partner Medical Dictionary,; Farlex, 2012 [retrieved on Dec. 21, 2022].
Khanh et al., Molecular Characterization of QX-Like and Variant Infectious Bronchitis Virus Strains in Malaysia Based on Partial Genomic Sequences Comprising the S-3a/3b-E-M-Intergenic Region-5a/5b-N Gene Order, Avian Dis. Dec. 2017, ol.61, No. 4,pp. 442-452.

\* cited by examiner

SEQUENCE LISTING

```
<160> NUMBER OF SEQ ID NOS: 85

<210> SEQ ID NO 1
<211> LENGTH: 1162
<212> TYPE: PRT
<213> ORGANISM: Avian infectious bronchitis virus

<400> SEQUENCE: 1

Met Leu Val Thr Pro Leu Leu Leu Val Thr Leu Leu Cys Ala Leu Cys
1               5                   10                  15
```

```
Ser Ala Ala Leu Tyr Asp Ser Ser Tyr Val Tyr Tyr Gln Ser
            20              25              30

Ala Phe Arg Pro Pro Asp Gly Trp His Leu His Gly Ala Tyr Ala
        35              40              45

Val Val Asn Ile Ser Ser Glu Ser Asn Ala Gly Ser Ser Ser Gly
    50              55              60

Cys Thr Val Gly Ile Ile His Gly Gly Arg Val Val Asn Ala Ser Ser
65              70              75              80

Ile Ala Met Thr Ala Pro Ser Ser Gly Met Ala Trp Ser Ser Gln
                85              90              95

Phe Cys Thr Ala Tyr Cys Asn Phe Ser Asp Thr Thr Val Phe Val Thr
                100             105             110

His Cys Tyr Lys His Gly Gly Cys Pro Ile Thr Gly Met Leu Gln Gln
                115             120             125

His Ser Ile Arg Val Ser Ala Met Lys Asn Gly Gln Leu Phe Tyr Asn
    130             135             140

Leu Thr Val Ser Val Ala Lys Tyr Pro Thr Phe Lys Ser Phe Gln Cys
145             150             155             160

Val Asn Asn Leu Thr Ser Val Tyr Leu Asn Gly Asp Leu Val Tyr Thr
                165             170             175

Ser Asn Glu Thr Thr Asp Val Thr Ser Ala Gly Val Tyr Phe Lys Ala
            180             185             190

Gly Gly Pro Ile Thr Tyr Lys Val Met Arg Glu Val Arg Ala Leu Ala
        195             200             205

Tyr Phe Val Asn Gly Thr Ala Gln Asp Val Ile Leu Cys Asp Gly Ser
    210             215             220

Pro Arg Gly Leu Leu Ala Cys Gln Tyr Asn Thr Gly Asn Phe Ser Asp
225             230             235             240

Gly Phe Tyr Pro Phe Thr Asn Ser Ser Leu Val Lys Gln Lys Phe Ile
                245             250             255

Val Tyr Arg Glu Asn Ser Val Asn Thr Thr Phe Thr Leu His Asn Phe
                260             265             270

Thr Phe His Asn Glu Thr Gly Ala Asn Pro Asn Pro Ser Gly Val Gln
            275             280             285

Asn Ile Gln Thr Tyr Gln Thr Gln Thr Ala Gln Ser Gly Tyr Tyr Asn
290             295             300

Phe Asn Phe Ser Phe Leu Ser Ser Phe Val Tyr Lys Glu Ser Asn Phe
305             310             315             320

Met Tyr Gly Ser Tyr His Pro Ser Cys Asn Phe Arg Leu Glu Thr Ile
                325             330             335

Asn Asn Gly Leu Trp Phe Asn Ser Leu Ser Val Ser Ile Ala Tyr Gly
            340             345             350

Pro Leu Gln Gly Gly Cys Lys Gln Ser Val Phe Ser Gly Arg Ala Thr
            355             360             365

Cys Cys Tyr Ala Tyr Ser Tyr Gly Gly Pro Leu Leu Cys Lys Gly Val
            370             375             380

Tyr Ser Gly Glu Leu Asp His Asn Phe Glu Cys Gly Leu Leu Val Tyr
385             390             395             400

Val Thr Lys Ser Gly Gly Ser Arg Ile Gln Thr Ala Thr Glu Pro Pro
            405             410             415

Val Ile Thr Gln His Asn Tyr Asn Asn Ile Thr Leu Asn Thr Cys Val
        420             425             430
```

```
Asp Tyr Asn Ile Tyr Gly Arg Thr Gly Gln Gly Phe Ile Thr Asn Val
            435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Ser Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
                500                 505                 510

Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Ser Val Glu
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
                580                 585                 590

Thr Val Thr Asp Glu Tyr Ile Gln Thr Arg Met Asp Lys Val Gln Ile
    595                 600                 605

Asn Cys Leu Gln Tyr Ile Cys Gly Asn Ser Leu Glu Cys Arg Asn Leu
610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
                660                 665                 670

Gly Glu Phe Asn Ile Thr Leu Phe Leu Thr Thr Pro Ser Ser Pro Arg
            675                 680                 685

Arg Arg Ser Phe Ile Glu Asp Leu Leu Phe Thr Ser Val Glu Ser Val
    690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Thr Leu Tyr Thr Ser
                740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
    770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Asn Lys Gln Ser Ala Ile Leu
                820                 825                 830

Thr Glu Thr Met Ala Ser Leu Asn Lys Asn Phe Gly Ala Ile Ser Ser
            835                 840                 845

Val Ile Gln Glu Ile Tyr Gln Gln Leu Asp Ala Ile Gln Ala Asn Ala
```

```
                850                 855                 860
Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
                900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
        930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile  Val Thr Leu Thr Ser  Cys Gln Ala
        995                 1000                1005

Asn Tyr  Val Ser Val Asn Lys  Thr Val Ile Thr Thr  Phe Val Asp
    1010                1015                1020

Asn Asp  Asp Phe Asp Phe Asn  Asp Glu Leu Ser Lys  Trp Trp Asn
    1025                1030                1035

Asp Thr  Lys His Glu Leu Pro  Asp Phe Asp Lys Phe  Asn Tyr Thr
    1040                1045                1050

Val Pro  Ile Leu Asp Ile Asp  Ser Glu Ile Asp Arg  Ile Gln Gly
    1055                1060                1065

Val Ile  Gln Gly Leu Asn Asp  Ser Leu Ile Asp Leu  Glu Lys Leu
    1070                1075                1080

Ser Ile  Leu Lys Thr Tyr Ile  Lys Trp Pro Trp Tyr  Val Trp Leu
    1085                1090                1095

Ala Ile  Ala Phe Ala Thr Ile  Ile Phe Ile Leu Ile  Leu Gly Trp
    1100                1105                1110

Val Phe  Phe Met Thr Gly Cys  Cys Gly Cys Cys Cys  Gly Cys Phe
    1115                1120                1125

Gly Ile  Met Pro Leu Met Ser  Lys Cys Gly Lys Lys  Ser Ser Tyr
    1130                1135                1140

Tyr Thr  Thr Phe Asp Asn Asp  Val Val Thr Glu Gln  Tyr Arg Pro
    1145                1150                1155

Lys Lys  Ser Val
    1160

<210> SEQ ID NO 2
<211> LENGTH: 409
<212> TYPE: PRT
<213> ORGANISM: Avian infectious bronchitis virus

<400> SEQUENCE: 2

Met Ala Ser Gly Lys Thr Thr Gly Lys Thr Asp Ala Pro Ala Pro Val
1               5                   10                  15

Ile Lys Leu Gly Gly Pro Lys Pro Lys Val Gly Ser Ser Gly Asn
            20                  25                  30

Ala Ser Trp Phe Gln Ala Leu Lys Ala Lys Lys Leu Asn Ser Pro Pro
        35                  40                  45
```

-continued

```
Pro Lys Phe Glu Gly Ser Gly Val Pro Asp Asn Glu Asn Leu Lys Leu
     50                  55                  60

Ser Gln Gln His Gly Tyr Trp Arg Arg Gln Ala Arg Tyr Lys Pro Gly
 65                  70                  75                  80

Lys Gly Gly Arg Lys Ser Val Pro Asp Ala Trp Tyr Phe Tyr Tyr Thr
                 85                  90                  95

Gly Thr Gly Pro Ala Ala Asp Leu Asn Trp Gly Asp Ser Gln Asp Gly
            100                 105                 110

Ile Val Trp Val Ser Ala Lys Gly Ala Asp Thr Lys Ser Arg Ser Asn
            115                 120                 125

Gln Gly Thr Arg Asp Pro Asp Lys Phe Asp Gln Tyr Pro Leu Arg Phe
    130                 135                 140

Ser Asp Gly Gly Pro Asp Gly Asn Phe Arg Trp Asp Phe Ile Pro Ile
145                 150                 155                 160

Asn Arg Gly Arg Ser Gly Arg Ser Thr Ala Ala Ser Ser Ala Ala Ser
                165                 170                 175

Ser Arg Ala Pro Ser Arg Asp Gly Ser Arg Gly Arg Arg Ser Gly Ala
            180                 185                 190

Glu Asp Asp Leu Ile Ala Arg Ala Ala Lys Ile Ile Gln Asp Gln Gln
            195                 200                 205

Lys Lys Gly Ser Arg Ile Thr Lys Ala Lys Ala Asp Glu Met Ala His
    210                 215                 220

Arg Arg Tyr Cys Lys Arg Thr Ile Pro Pro Gly Tyr Lys Val Asp Gln
225                 230                 235                 240

Val Phe Gly Pro Arg Thr Lys Gly Lys Glu Gly Asn Phe Gly Asp Asp
                245                 250                 255

Lys Met Asn Glu Glu Gly Ile Lys Asp Gly Arg Val Thr Ala Met Leu
            260                 265                 270

Asn Leu Val Pro Ser Ser His Ala Cys Leu Phe Gly Ser Arg Val Thr
            275                 280                 285

Pro Lys Leu Gln Pro Asp Gly Leu His Leu Arg Phe Glu Phe Thr Thr
    290                 295                 300

Val Val Ser Arg Asp Asp Pro Gln Phe Asp Asn Tyr Val Lys Ile Cys
305                 310                 315                 320

Asp Gln Cys Val Asp Gly Val Gly Thr Arg Pro Lys Asp Asp Glu Pro
                325                 330                 335

Arg Pro Lys Ser Arg Pro Asn Ser Arg Pro Ala Thr Arg Thr Ser Ser
            340                 345                 350

Pro Ala Pro Arg Gln Gln Arg Gln Lys Lys Glu Lys Lys Ser Lys Lys
            355                 360                 365

Gln Asp Asp Glu Val Asp Lys Ala Leu Thr Ser Asp Glu Glu Arg Asn
    370                 375                 380

Asn Ala Gln Leu Glu Phe Asp Asp Glu Pro Lys Val Ile Asn Trp Gly
385                 390                 395                 400

Asp Ser Ala Leu Gly Glu Asn Glu Leu
                405
```

<210> SEQ ID NO 3
<211> LENGTH: 110
<212> TYPE: PRT
<213> ORGANISM: Avian infectious bronchitis virus

<400> SEQUENCE: 3

```
Val Met Met Asn Leu Leu Asn Lys Ser Leu Glu Glu Asn Gly Ser Phe
 1               5                  10                  15
```

Leu Thr Ala Leu Tyr Ile Phe Val Gly Phe Leu Ala Phe Tyr Leu Leu
                20                  25                  30

Gly Arg Ala Leu Gln Ala Phe Val Gln Ala Ala Asp Ala Cys Cys Leu
            35                  40                  45

Phe Trp Tyr Thr Trp Leu Val Ile Pro Gly Val Lys Gly Thr Ala Phe
 50                  55                  60

Val Tyr Lys Tyr Thr Tyr Gly Arg Lys Leu Asn Asn Ser Glu Leu Glu
 65                  70                  75                  80

Ala Val Val Val Asn Glu Phe Pro Lys Asn Gly Trp Asn Asn Lys Asn
                85                  90                  95

Pro Ala Asn Phe Gln Asp Val Gln Arg Asn Lys Leu Tyr Ser
            100                 105                 110

<210> SEQ ID NO 4
<211> LENGTH: 225
<212> TYPE: PRT
<213> ORGANISM: Avian infectious bronchitis virus

<400> SEQUENCE: 4

Met Ser Asn Glu Thr Asn Cys Thr Leu Asp Phe Glu Gln Ser Val Glu
 1               5                  10                  15

Leu Phe Lys Glu Tyr Asn Leu Phe Ile Thr Ala Phe Leu Leu Phe Leu
                20                  25                  30

Thr Ile Ile Leu Gln Tyr Gly Tyr Ala Thr Arg Ser Lys Phe Ile Tyr
            35                  40                  45

Ile Leu Lys Met Ile Val Leu Trp Cys Phe Trp Pro Leu Asn Ile Ala
 50                  55                  60

Val Gly Val Ile Ser Cys Ile Tyr Pro Pro Asn Thr Gly Gly Leu Val
 65                  70                  75                  80

Ala Ala Ile Ile Leu Thr Val Phe Ala Cys Leu Ser Phe Val Gly Tyr
                85                  90                  95

Trp Ile Gln Ser Ile Arg Leu Phe Lys Arg Cys Arg Ser Trp Trp Ser
            100                 105                 110

Phe Asn Pro Glu Ser Asn Ala Val Gly Ser Ile Leu Leu Thr Asn Gly
            115                 120                 125

Gln Gln Cys Asn Phe Ala Ile Glu Ser Val Pro Met Val Leu Ser Pro
130                 135                 140

Ile Ile Lys Asn Gly Val Leu Tyr Cys Glu Gly Gln Trp Leu Ala Lys
145                 150                 155                 160

Cys Glu Pro Asp His Leu Pro Lys Asp Ile Phe Val Cys Thr Pro Asp
                165                 170                 175

Arg Arg Asn Ile Tyr Arg Met Val Gln Lys Tyr Thr Gly Asp Gln Ser
            180                 185                 190

Gly Asn Lys Lys Arg Phe Ala Thr Phe Val Tyr Ala Lys Gln Ser Val
            195                 200                 205

Asp Thr Gly Glu Leu Glu Ser Val Ala Thr Gly Gly Ser Ser Leu Tyr
            210                 215                 220

Thr
225

<210> SEQ ID NO 5
<211> LENGTH: 1155
<212> TYPE: PRT
<213> ORGANISM: Avian infectious bronchitis virus

<400> SEQUENCE: 5

```
Met Leu Asp Lys Pro Leu Leu Leu Val Thr Leu Trp Tyr Ala Leu Cys
1               5                   10                  15

Ser Ala Leu Leu Tyr Asp Asn Asn Thr Tyr Val Tyr Tyr Tyr Gln Ser
            20                  25                  30

Ala Phe Arg Pro Gly Pro Gly Trp His Leu Tyr Gly Gly Ala Tyr Ala
            35                  40                  45

Val Asp Arg Val Phe Asn Glu Thr Asn Asn Ala Gly Ser Ala Ser Asp
50              55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
                100                 105                 110

His Cys Phe Lys Asn Gln Leu Gly Ser Cys Pro Leu Thr Gly Met Ile
            115                 120                 125

Pro Gln Asn His Ile Arg Ile Ser Ala Met Arg Asp Gly Val Leu Phe
            130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
                180                 185                 190

Lys Ser Gly Gly Pro Val Thr Tyr Lys Val Met Lys Glu Val Lys Ala
            195                 200                 205

Leu Ala Tyr Phe Ile Asn Gly Thr Ala Gln Glu Val Ile Leu Cys Asp
210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Leu Lys Leu Thr
                260                 265                 270

Asn Phe Ser Phe Thr Asn Val Ser Asn Ala Ser Pro Asn Ser Gly Gly
            275                 280                 285

Val Asp Thr Phe Gln Leu Tyr Gln Thr Ser Thr Ala Gln Asp Gly Tyr
            290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr
            340                 345                 350

Tyr Gly Pro Ile Gln Gly Gly Cys Lys Gln Ser Val Phe Ser Asn Arg
            355                 360                 365

Ala Thr Cys Cys Tyr Ala Tyr Ser Tyr Gln Gly Pro Ser Arg Cys Lys
            370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415
```

```
Pro Leu Val Leu Thr Gln Tyr Asn Tyr Asn Asn Ile Thr Leu Asn Lys
            420                 425                 430

Cys Val Glu Tyr Asn Ile Tyr Gly Arg Val Gly Gln Gly Phe Ile Thr
            435                 440                 445

Asn Val Thr Glu Ala Thr Ala Asn Tyr Ser Tyr Leu Ala Asp Gly Gly
            450                 455                 460

Leu Ala Ile Leu Asp Thr Ser Gly Ala Ile Asp Ile Phe Val Val Gln
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
            500                 505                 510

Ser His Asn Glu Thr Gly Ser Glu Ser Ile Glu Asn Gln Phe Tyr Ile
            515                 520                 525

Lys Leu Thr Asn Gly Thr Arg Arg Ser Arg Arg Ser Val Thr Gly Asn
            530                 535                 540

Val Thr Asn Cys Pro Tyr Val Ser Tyr Gly Lys Phe Cys Ile Lys Pro
545                 550                 555                 560

Asp Gly Ser Leu Ser Ile Ile Val Pro Gln Glu Leu Glu Gln Phe Val
                565                 570                 575

Ala Pro Leu Phe Asn Val Thr Glu His Val Leu Ile Pro Asp Ser Phe
            580                 585                 590

Asn Leu Thr Val Thr Asp Glu Tyr Ile Gln Thr Arg Met Asp Lys Val
            595                 600                 605

Gln Ile Ile Cys Leu Gln Tyr Val Cys Gly Asn Ser Ile Glu Cys Arg
610                 615                 620

Lys Leu Phe Gln Gln Tyr Gly Pro Val Cys Asp Asn Ile Leu Ser Val
625                 630                 635                 640

Val Asn Gly Val Gly Gln Arg Glu Asp Met Glu Leu Leu Ser Phe Tyr
                645                 650                 655

Ser Ser Thr Lys Pro Ser Gly Tyr Asn Thr Pro Ile Phe Asn Asn Val
            660                 665                 670

Ser Thr Gly Asp Phe Asn Ile Ser Leu Leu Leu Thr Pro Pro Asn Ser
            675                 680                 685

Pro Thr Gly Arg Ser Phe Ile Glu Asp Leu Leu Phe Thr Ser Val Glu
690                 695                 700

Ser Val Gly Leu Pro Thr Asp Glu Glu Tyr Lys Lys Cys Thr Ala Gly
705                 710                 715                 720

Pro Leu Gly Phe Val Lys Asp Leu Val Cys Ala Arg Glu Tyr Asn Gly
                725                 730                 735

Leu Leu Val Leu Pro Pro Ile Ile Thr Ala Glu Met Gln Thr Met Tyr
            740                 745                 750

Thr Ser Ser Leu Val Ala Ser Met Ala Leu Gly Gly Ile Thr Ala Ala
            755                 760                 765

Gly Ala Ile Pro Phe Ala Thr Gln Leu Gln Ala Arg Ile Asn His Leu
770                 775                 780

Gly Ile Thr Asn Ser Leu Leu Lys Asn Gln Glu Lys Ile Ala Ala
785                 790                 795                 800

Ser Phe Asn Lys Ala Ile Gly His Met Gln Glu Gly Phe Lys Ser Thr
                805                 810                 815

Ser Leu Ala Leu Gln Gln Ile Gln Asp Val Val Asn Lys Gln Ser Ser
            820                 825                 830

Ile Leu Thr Glu Thr Met Gln Ser Leu Asn Lys Asn Phe Gly Ala Ile
```

```
                835                 840                 845
Ser Ser Val Ile Gln Asp Ile Tyr Gln Gln Leu Asp Ala Ile Gln Ala
    850                 855                 860

Asp Ala Gln Val Asp Arg Leu Ile Thr Gly Arg Leu Ser Ser Leu Ser
865                 870                 875                 880

Val Leu Ala Ser Ala Lys Gln Ala Glu Tyr His Arg Val Ser Gln Gln
                885                 890                 895

Arg Glu Leu Ala Thr Gln Lys Ile Asn Glu Cys Val Lys Ser Gln Ser
            900                 905                 910

Asn Arg Tyr Ser Phe Cys Gly Asn Gly Arg His Val Leu Thr Ile Pro
        915                 920                 925

Gln Asn Ala Pro Asn Gly Ile Val Phe Ile His Phe Thr Tyr Thr Pro
    930                 935                 940

Glu Ser Phe Val Asn Val Thr Ala Ile Val Gly Phe Cys Val Asn Pro
945                 950                 955                 960

Ala Asn Ala Ser His Tyr Ala Ile Val Pro Val Asn Gly Arg Gly Val
                965                 970                 975

Phe Ile Glu Val Asn Gly Ser Tyr Tyr Ile Thr Ala Arg Asp Met Tyr
            980                 985                 990

Met Pro Arg Asp Ile Thr Ala Gly Asp Ile Val Thr Leu Thr Ser Cys
        995                 1000                1005

Gln Ala Asn Tyr Val Asn Val Asn Lys Thr Val Ile Asn Thr Phe
    1010                1015                1020

Val Glu Asp Asp Asp Phe Asp Phe Tyr Asp Glu Leu Ser Lys Trp
    1025                1030                1035

Trp Asn Asp Thr Lys His Glu Leu Pro Asp Phe Asp Glu Phe Asn
    1040                1045                1050

Tyr Thr Val Pro Val Leu Asn Ile Ser Asn Glu Ile Asp Arg Ile
    1055                1060                1065

Gln Gln Val Ile Gln Gly Leu Asn Asp Ser Leu Ile Asp Leu Glu
    1070                1075                1080

Thr Leu Ser Ile Leu Lys Thr Tyr Ile Lys Trp Pro Trp Tyr Val
    1085                1090                1095

Trp Leu Ala Ile Ala Phe Leu Thr Ile Ile Phe Ile Leu Val Leu
    1100                1105                1110

Cys Trp Ile Phe Phe Met Thr Gly Cys Cys Gly Cys Cys Cys Gly
    1115                1120                1125

Cys Phe Gly Ile Ile Pro Leu Met Ser Lys Cys Gly Lys Lys Ser
    1130                1135                1140

Ser Tyr Tyr Thr Thr Phe Asp Asn Asp Val Val Thr
    1145                1150                1155

<210> SEQ ID NO 6
<211> LENGTH: 1077
<212> TYPE: PRT
<213> ORGANISM: Avian infectious bronchitis virus

<400> SEQUENCE: 6

Leu Leu Tyr Asp Asn Asn Thr Tyr Val Tyr Tyr Tyr Gln Ser Ala Phe
1               5                   10                  15

Arg Pro Gly Pro Gly Trp His Leu Tyr Gly Gly Ala Tyr Ala Val Asp
            20                  25                  30

Arg Val Phe Asn Glu Thr Asn Asn Ala Gly Ser Ala Ser Asp Cys Thr
        35                  40                  45
```

```
Ala Gly Thr Phe Tyr Glu Ser His Asn Ile Ser Ala Ser Ser Val Ala
    50                  55                  60

Met Thr Val Pro His Asn Gly Met Ser Trp Ser Ala Ser Gln Phe Cys
65                  70                  75                  80

Thr Ala His Cys Asn Phe Ser Asp Phe Thr Val Phe Val Thr His Cys
                85                  90                  95

Phe Lys Asn Gln Leu Gly Ser Cys Pro Leu Thr Gly Met Ile Pro Gln
                100                 105                 110

Asn His Ile Arg Ile Ser Ala Met Arg Asp Gly Val Leu Phe Tyr Asn
                115                 120                 125

Leu Thr Val Ser Val Ser Lys Tyr Pro Arg Phe Lys Ser Leu Gln Cys
    130                 135                 140

Val Ser Asn Ser Thr Ser Val Tyr Val Asn Gly Asp Leu Val Phe Thr
145                 150                 155                 160

Ser Asn Glu Thr Ser Tyr Val Thr Gly Ala Gly Val Tyr Phe Lys Ser
                165                 170                 175

Gly Gly Pro Val Thr Tyr Lys Val Met Lys Glu Val Lys Ala Leu Ala
                180                 185                 190

Tyr Phe Ile Asn Gly Thr Ala Gln Glu Val Ile Leu Cys Asp Asn Ser
                195                 200                 205

Pro Arg Gly Leu Leu Ala Cys Gln Tyr Asn Thr Gly Asn Phe Ser Asp
            210                 215                 220

Gly Phe Tyr Pro Phe Thr Asn His Ser Leu Val Lys Asp Arg Phe Ile
225                 230                 235                 240

Val Tyr Arg Glu Ser Ser Thr Asn Thr Thr Leu Lys Leu Thr Asn Phe
                245                 250                 255

Ser Phe Thr Asn Val Ser Asn Ala Ser Pro Asn Ser Gly Gly Val Asp
            260                 265                 270

Thr Phe Gln Leu Tyr Gln Thr Ser Thr Ala Gln Asp Gly Tyr Tyr Asn
            275                 280                 285

Phe Asn Leu Ser Phe Leu Ser Ser Phe Val Tyr Lys Pro Ser Asp Phe
290                 295                 300

Met Tyr Gly Ser Tyr His Pro His Cys Lys Phe Arg Pro Glu Asn Ile
305                 310                 315                 320

Asn Asn Gly Leu Trp Phe Asn Ser Leu Ser Val Ser Leu Thr Tyr Gly
                325                 330                 335

Pro Ile Gln Gly Gly Cys Lys Gln Ser Val Phe Ser Asn Arg Ala Thr
                340                 345                 350

Cys Cys Tyr Ala Tyr Ser Tyr Gln Gly Pro Ser Arg Cys Lys Gly Val
            355                 360                 365

Tyr Arg Gly Glu Leu Thr Gln Tyr Phe Glu Cys Gly Leu Leu Val Tyr
    370                 375                 380

Val Thr Lys Ser Asp Gly Ser Arg Ile Gln Thr Arg Ser Glu Pro Leu
385                 390                 395                 400

Val Leu Thr Gln Tyr Asn Tyr Asn Asn Ile Thr Leu Asn Lys Cys Val
                405                 410                 415

Glu Tyr Asn Ile Tyr Gly Arg Val Gly Gln Gly Phe Ile Thr Asn Val
                420                 425                 430

Thr Glu Ala Thr Ala Asn Tyr Ser Tyr Leu Ala Asp Gly Gly Leu Ala
            435                 440                 445

Ile Leu Asp Thr Ser Gly Ala Ile Asp Ile Phe Val Val Gln Gly Ala
    450                 455                 460

Tyr Gly Leu Asn Tyr Tyr Lys Val Asn Pro Cys Glu Asp Val Asn Gln
```

```
            465                 470                 475                 480
        Gln Phe Val Val Ser Gly Gly Asn Leu Val Gly Ile Leu Thr Ser His
                            485                 490                 495

Asn Glu Thr Gly Ser Glu Ser Ile Glu Asn Gln Phe Tyr Ile Lys Leu
                        500                 505                 510

Thr Asn Gly Thr Arg Arg Ser Arg Arg Ser Val Thr Gly Asn Val Thr
                        515                 520                 525

Asn Cys Pro Tyr Val Ser Tyr Gly Lys Phe Cys Ile Lys Pro Asp Gly
                        530                 535                 540

Ser Leu Ser Ile Ile Val Pro Gln Glu Leu Glu Gln Phe Val Ala Pro
        545                 550                 555                 560

Leu Phe Asn Val Thr Glu His Val Leu Ile Pro Asp Ser Phe Asn Leu
                            565                 570                 575

Thr Val Thr Asp Glu Tyr Ile Gln Thr Arg Met Asp Lys Val Gln Ile
                        580                 585                 590

Ile Cys Leu Gln Tyr Val Cys Gly Asn Ser Ile Glu Cys Arg Lys Leu
                    595                 600                 605

Phe Gln Gln Tyr Gly Pro Val Cys Asp Asn Ile Leu Ser Val Val Asn
                610                 615                 620

Gly Val Gly Gln Arg Glu Asp Met Glu Leu Leu Ser Phe Tyr Ser Ser
        625                 630                 635                 640

Thr Lys Pro Ser Gly Tyr Asn Thr Pro Ile Phe Asn Asn Val Ser Thr
                        645                 650                 655

Gly Asp Phe Asn Ile Ser Leu Leu Leu Thr Pro Pro Asn Ser Pro Thr
                        660                 665                 670

Gly Arg Ser Phe Ile Glu Asp Leu Leu Phe Thr Ser Val Glu Ser Val
                    675                 680                 685

Gly Leu Pro Thr Asp Glu Glu Tyr Lys Lys Cys Thr Ala Gly Pro Leu
                690                 695                 700

Gly Phe Val Lys Asp Leu Val Cys Ala Arg Glu Tyr Asn Gly Leu Leu
        705                 710                 715                 720

Val Leu Pro Pro Ile Ile Thr Ala Glu Met Gln Thr Met Tyr Thr Ser
                            725                 730                 735

Ser Leu Val Ala Ser Met Ala Leu Gly Gly Ile Thr Ala Ala Gly Ala
                        740                 745                 750

Ile Pro Phe Ala Thr Gln Leu Gln Ala Arg Ile Asn His Leu Gly Ile
                        755                 760                 765

Thr Asn Ser Leu Leu Leu Lys Asn Gln Glu Lys Ile Ala Ala Ser Phe
        770                 775                 780

Asn Lys Ala Ile Gly His Met Gln Glu Gly Phe Lys Ser Thr Ser Leu
        785                 790                 795                 800

Ala Leu Gln Gln Ile Gln Asp Val Val Asn Lys Gln Ser Ser Ile Leu
                        805                 810                 815

Thr Glu Thr Met Gln Ser Leu Asn Lys Asn Phe Gly Ala Ile Ser Ser
                    820                 825                 830

Val Ile Gln Asp Ile Tyr Gln Gln Leu Asp Ala Ile Gln Ala Asp Ala
                    835                 840                 845

Gln Val Asp Arg Leu Ile Thr Gly Arg Leu Ser Ser Leu Ser Val Leu
                850                 855                 860

Ala Ser Ala Lys Gln Ala Glu Tyr His Arg Val Ser Gln Gln Arg Glu
        865                 870                 875                 880

Leu Ala Thr Gln Lys Ile Asn Glu Cys Val Lys Ser Gln Ser Asn Arg
                        885                 890                 895
```

-continued

Tyr Ser Phe Cys Gly Asn Gly Arg His Val Leu Thr Ile Pro Gln Asn
            900                 905                 910

Ala Pro Asn Gly Ile Val Phe Ile His Phe Thr Tyr Thr Pro Glu Ser
            915                 920                 925

Phe Val Asn Val Thr Ala Ile Val Gly Phe Cys Val Asn Pro Ala Asn
        930                 935                 940

Ala Ser His Tyr Ala Ile Val Pro Val Asn Gly Arg Gly Val Phe Ile
945                 950                 955                 960

Glu Val Asn Gly Ser Tyr Tyr Ile Thr Ala Arg Asp Met Tyr Met Pro
            965                 970                 975

Arg Asp Ile Thr Ala Gly Asp Ile Val Thr Leu Thr Ser Cys Gln Ala
            980                 985                 990

Asn Tyr Val Asn Val Asn Lys Thr Val Ile Asn Thr Phe Val Glu Asp
            995                 1000                1005

Asp Asp Phe Asp Phe Tyr Asp Glu Leu Ser Lys Trp Trp Asn Asp
            1010                1015                1020

Thr Lys His Glu Leu Pro Asp Phe Asp Glu Phe Asn Tyr Thr Val
            1025                1030                1035

Pro Val Leu Asn Ile Ser Asn Glu Ile Asp Arg Ile Gln Gln Val
            1040                1045                1050

Ile Gln Gly Leu Asn Asp Ser Leu Ile Asp Leu Glu Thr Leu Ser
            1055                1060                1065

Ile Leu Lys Thr Tyr Ile Lys Trp Pro
            1070                1075

<210> SEQ ID NO 7
<211> LENGTH: 1156
<212> TYPE: PRT
<213> ORGANISM: Avian infectious bronchitis virus

<400> SEQUENCE: 7

Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Ser Ser Thr Asn Tyr Thr Asn Asn Ala Gly Ser Ala His
50                  55                  60

Gly Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
        115                 120                 125

Ile Pro Arg Asp His Ile Arg Ile Ser Ala Met Lys Asn Gly Ser Leu
130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr

```
                180                 185                 190
Phe Lys Ala Gly Gly Pro Val Asn Tyr Ser Ile Met Lys Glu Phe Lys
            195                 200                 205
Val Leu Ala Tyr Phe Val Asn Gly Thr Ala Gln Asp Val Val Leu Cys
        210                 215                 220
Asp Asn Ser Pro Lys Gly Leu Leu Ala Cys Gln Tyr Asn Thr Gly Asn
225                 230                 235                 240
Phe Ser Asp Gly Phe Tyr Pro Phe Thr Asn Ser Thr Leu Val Arg Glu
                245                 250                 255
Lys Phe Ile Val Tyr Arg Glu Ser Ser Val Asn Thr Thr Leu Ala Leu
            260                 265                 270
Thr Asn Phe Thr Phe Ser Asn Val Ser Asn Ala Gln Pro Asn Ser Gly
        275                 280                 285
Gly Val Asn Thr Phe His Leu Tyr Gln Thr Gln Thr Ala Gln Ser Gly
        290                 295                 300
Tyr Tyr Asn Phe Asn Leu Ser Phe Leu Ser Gln Phe Val Tyr Lys Ala
305                 310                 315                 320
Ser Asp Phe Met Tyr Gly Ser Tyr His Pro Ser Cys Ser Phe Arg Pro
                325                 330                 335
Glu Thr Ile Asn Ser Gly Leu Trp Phe Asn Ser Leu Ser Val Ser Leu
            340                 345                 350
Thr Tyr Gly Pro Leu Gln Gly Gly Cys Lys Gln Ser Val Phe Ser Gly
        355                 360                 365
Lys Ala Thr Cys Cys Tyr Ala Tyr Ser Tyr Arg Gly Pro Met Ala Cys
370                 375                 380
Lys Gly Val Tyr Ser Gly Glu Leu Ser Thr Asn Phe Glu Cys Gly Leu
385                 390                 395                 400
Leu Val Tyr Val Thr Lys Ser Asp Gly Ser Arg Ile Gln Thr Arg Thr
                405                 410                 415
Glu Pro Leu Val Leu Thr Gln Tyr Asn Tyr Asn Asn Ile Thr Leu Asp
            420                 425                 430
Lys Cys Val Ala Tyr Asn Ile Tyr Gly Arg Val Gly Gln Gly Phe Ile
        435                 440                 445
Thr Asn Val Thr Asp Ser Ala Ala Asn Phe Ser Tyr Leu Ala Asp Gly
        450                 455                 460
Gly Leu Ala Ile Leu Asp Thr Ser Gly Ala Ile Asp Val Phe Val Val
465                 470                 475                 480
Gln Gly Ile Tyr Gly Leu Asn Tyr Tyr Lys Val Asn Pro Cys Glu Asp
                485                 490                 495
Val Asn Gln Gln Phe Val Val Ser Gly Gly Asn Ile Val Gly Ile Leu
            500                 505                 510
Thr Ser Arg Asn Glu Thr Gly Ser Glu Gln Val Glu Asn Gln Phe Tyr
        515                 520                 525
Val Lys Leu Thr Asn Ser Ser His Arg Arg Lys Arg Ser Ile Gly Gln
        530                 535                 540
Asn Val Thr Ser Cys Pro Tyr Val Ser Tyr Gly Arg Phe Cys Ile Glu
545                 550                 555                 560
Pro Asp Gly Ser Leu Lys Met Ile Val Pro Glu Glu Leu Lys Gln Phe
                565                 570                 575
Val Ala Pro Leu Leu Asn Ile Thr Glu Ser Val Leu Ile Pro Asn Ser
            580                 585                 590
Phe Asn Leu Thr Val Thr Asp Glu Tyr Ile Gln Thr Arg Met Asp Lys
        595                 600                 605
```

```
Val Gln Ile Asn Cys Leu Gln Tyr Val Cys Gly Asn Ser Leu Glu Cys
610                 615                 620
Arg Lys Leu Phe Gln Gln Tyr Gly Pro Val Cys Asp Asn Ile Leu Ser
625                 630                 635                 640
Val Val Asn Ser Val Ser Gln Lys Glu Asp Met Glu Leu Leu Ser Phe
                645                 650                 655
Tyr Ser Ser Thr Lys Pro Lys Gly Tyr Asp Thr Pro Val Leu Ser Asn
                660                 665                 670
Val Ser Thr Gly Glu Phe Asn Ile Ser Leu Leu Leu Lys Pro Pro Ser
            675                 680                 685
Ser Pro Ser Gly Arg Ser Phe Ile Glu Glu Leu Phe Thr Ser Val
690                 695                 700
Glu Thr Val Gly Leu Pro Thr Asp Ala Glu Tyr Lys Lys Cys Thr Ala
705                 710                 715                 720
Gly Pro Leu Gly Thr Leu Lys Asp Leu Ile Cys Ala Arg Glu Tyr Asn
                725                 730                 735
Gly Leu Leu Val Leu Pro Pro Ile Ile Thr Ala Asp Met Gln Thr Met
                740                 745                 750
Tyr Thr Ala Ser Leu Val Gly Ala Met Ala Phe Gly Gly Ile Thr Ser
                755                 760                 765
Ala Ala Ala Ile Pro Phe Ala Thr Gln Ile Gln Ala Arg Ile Asn His
770                 775                 780
Leu Gly Ile Thr Gln Ser Leu Leu Met Lys Asn Gln Glu Lys Ile Ala
785                 790                 795                 800
Ala Ser Phe Asn Lys Ala Ile Gly His Met Gln Glu Gly Phe Arg Ser
                805                 810                 815
Thr Ser Leu Ala Leu Gln Gln Ile Gln Asp Val Val Asn Lys Gln Ser
                820                 825                 830
Ala Ile Leu Thr Glu Thr Met Asn Ser Leu Asn Lys Asn Phe Gly Ala
            835                 840                 845
Ile Thr Ser Val Ile Gln Asp Ile Tyr Ala Gln Leu Asp Ala Ile Gln
            850                 855                 860
Ala Asp Ala Gln Val Asp Arg Leu Ile Thr Gly Arg Leu Ser Ser Leu
865                 870                 875                 880
Ser Val Leu Ala Ser Ala Lys Gln Ser Glu Tyr Ile Arg Val Ser Gln
                885                 890                 895
Gln Arg Glu Leu Ala Thr Gln Lys Ile Asn Glu Cys Val Lys Ser Gln
                900                 905                 910
Ser Asn Arg Tyr Gly Phe Cys Gly Ser Gly Arg His Val Leu Ser Ile
            915                 920                 925
Pro Gln Asn Ala Pro Asn Gly Ile Val Phe Ile His Phe Thr Tyr Thr
930                 935                 940
Pro Glu Ser Phe Val Asn Val Thr Ala Ile Val Gly Phe Cys Val Asn
945                 950                 955                 960
Pro Ala Asn Ala Ser Gln Tyr Ala Ile Val Pro Ala Asn Gly Arg Gly
                965                 970                 975
Ile Phe Ile Gln Val Asn Gly Thr Tyr Tyr Ile Thr Ala Arg Asp Met
            980                 985                 990
Tyr Met Pro Arg Asp Ile Thr Ala Gly Asp Ile Val Thr Leu Thr Ser
            995             1000            1005
Cys Gln Ala Asn Tyr Val Asn Val Asn Lys Thr Val Ile Thr Thr
    1010            1015            1020
```

```
Phe Val Glu Asp Asp Asp Phe Asp Phe Asp Asp Glu Leu Ser Lys
    1025                1030                1035

Trp Trp Asn Asp Thr Lys His Gln Leu Pro Asp Phe Asp Asp Phe
    1040                1045                1050

Asn Tyr Thr Val Pro Ile Leu Asn Ile Ser Gly Glu Ile Asp Tyr
    1055                1060                1065

Ile Gln Gly Val Ile Gln Gly Leu Asn Asp Ser Leu Ile Asp Leu
    1070                1075                1080

Glu Glu Leu Ser Ile Ile Lys Thr Tyr Ile Lys Trp Pro Trp Tyr
    1085                1090                1095

Val Trp Leu Ala Ile Phe Phe Ala Ile Ile Ile Phe Ile Leu Ile
    1100                1105                1110

Leu Gly Trp Val Phe Phe Met Thr Gly Cys Cys Gly Cys Cys Cys
    1115                1120                1125

Gly Cys Phe Gly Ile Ile Pro Leu Met Ser Lys Cys Gly Lys Lys
    1130                1135                1140

Ser Ser Tyr Tyr Thr Thr Phe Asp Asn Asp Val Val Thr
    1145                1150                1155

<210> SEQ ID NO 8
<211> LENGTH: 1078
<212> TYPE: PRT
<213> ORGANISM: Avian infectious bronchitis virus

<400> SEQUENCE: 8

Asn Leu Phe Asp Ser Asp Asn Asn Tyr Val Tyr Tyr Tyr Gln Ser Ala
1               5                   10                  15

Phe Arg Pro Pro Asn Gly Trp His Leu Gln Gly Gly Ala Tyr Ala Val
                20                  25                  30

Val Ser Ser Thr Asn Tyr Thr Asn Asn Ala Gly Ser Ala His Gly Cys
            35                  40                  45

Thr Val Gly Val Ile Lys Asp Val Tyr Asn Gln Ser Val Ala Ser Ile
        50                  55                  60

Ala Met Thr Ala Pro Leu Gln Gly Met Ala Trp Ser Lys Ser Gln Phe
65              70                  75                  80

Cys Ser Ala His Cys Asn Phe Ser Glu Ile Thr Val Phe Val Thr His
                85                  90                  95

Cys Tyr Ser Ser Gly Ser Gly Ser Cys Pro Ile Thr Gly Met Ile Pro
            100                 105                 110

Arg Asp His Ile Arg Ile Ser Ala Met Lys Asn Gly Ser Leu Phe Tyr
        115                 120                 125

Asn Leu Thr Val Ser Val Ser Lys Tyr Pro Asn Phe Lys Ser Phe Gln
    130                 135                 140

Cys Val Asn Asn Phe Thr Ser Val Tyr Leu Asn Gly Asp Leu Val Phe
145                 150                 155                 160

Thr Ser Asn Lys Thr Thr Asp Val Thr Ser Ala Gly Val Tyr Phe Lys
                165                 170                 175

Ala Gly Gly Pro Val Asn Tyr Ser Ile Met Lys Glu Phe Lys Val Leu
            180                 185                 190

Ala Tyr Phe Val Asn Gly Thr Ala Gln Asp Val Val Leu Cys Asp Asn
        195                 200                 205

Ser Pro Lys Gly Leu Leu Ala Cys Gln Tyr Asn Thr Gly Asn Phe Ser
    210                 215                 220

Asp Gly Phe Tyr Pro Phe Thr Asn Ser Thr Leu Val Arg Glu Lys Phe
225                 230                 235                 240
```

-continued

```
Ile Val Tyr Arg Glu Ser Ser Val Asn Thr Thr Leu Ala Leu Thr Asn
                245                 250                 255

Phe Thr Phe Ser Asn Val Ser Asn Ala Gln Pro Asn Ser Gly Gly Val
            260                 265                 270

Asn Thr Phe His Leu Tyr Gln Thr Gln Thr Ala Gln Ser Gly Tyr Tyr
        275                 280                 285

Asn Phe Asn Leu Ser Phe Leu Ser Gln Phe Val Tyr Lys Ala Ser Asp
    290                 295                 300

Phe Met Tyr Gly Ser Tyr His Pro Ser Cys Ser Phe Arg Pro Glu Thr
305                 310                 315                 320

Ile Asn Ser Gly Leu Trp Phe Asn Ser Leu Ser Val Ser Leu Thr Tyr
                325                 330                 335

Gly Pro Leu Gln Gly Gly Cys Lys Gln Ser Val Phe Ser Gly Lys Ala
            340                 345                 350

Thr Cys Cys Tyr Ala Tyr Ser Tyr Arg Gly Pro Met Ala Cys Lys Gly
        355                 360                 365

Val Tyr Ser Gly Glu Leu Ser Thr Asn Phe Glu Cys Gly Leu Leu Val
    370                 375                 380

Tyr Val Thr Lys Ser Asp Gly Ser Arg Ile Gln Thr Arg Thr Glu Pro
385                 390                 395                 400

Leu Val Leu Thr Gln Tyr Asn Tyr Asn Asn Ile Thr Leu Asp Lys Cys
                405                 410                 415

Val Ala Tyr Asn Ile Tyr Gly Arg Val Gly Gln Gly Phe Ile Thr Asn
            420                 425                 430

Val Thr Asp Ser Ala Ala Asn Phe Ser Tyr Leu Ala Asp Gly Gly Leu
        435                 440                 445

Ala Ile Leu Asp Thr Ser Gly Ala Ile Asp Val Phe Val Val Gln Gly
    450                 455                 460

Ile Tyr Gly Leu Asn Tyr Tyr Lys Val Asn Pro Cys Glu Asp Val Asn
465                 470                 475                 480

Gln Gln Phe Val Val Ser Gly Gly Asn Ile Val Gly Ile Leu Thr Ser
                485                 490                 495

Arg Asn Glu Thr Gly Ser Glu Gln Val Glu Asn Gln Phe Tyr Val Lys
            500                 505                 510

Leu Thr Asn Ser Ser His Arg Arg Lys Arg Ser Ile Gly Gln Asn Val
        515                 520                 525

Thr Ser Cys Pro Tyr Val Ser Tyr Gly Arg Phe Cys Ile Glu Pro Asp
    530                 535                 540

Gly Ser Leu Lys Met Ile Val Pro Glu Glu Leu Lys Gln Phe Val Ala
545                 550                 555                 560

Pro Leu Leu Asn Ile Thr Glu Ser Val Leu Ile Pro Asn Ser Phe Asn
                565                 570                 575

Leu Thr Val Thr Asp Glu Tyr Ile Gln Thr Arg Met Asp Lys Val Gln
            580                 585                 590

Ile Asn Cys Leu Gln Tyr Val Cys Gly Asn Ser Leu Glu Cys Arg Lys
        595                 600                 605

Leu Phe Gln Gln Tyr Gly Pro Val Cys Asp Asn Ile Leu Ser Val Val
    610                 615                 620

Asn Ser Val Ser Gln Lys Glu Asp Met Glu Leu Leu Ser Phe Tyr Ser
625                 630                 635                 640

Ser Thr Lys Pro Lys Gly Tyr Asp Thr Pro Val Leu Ser Asn Val Ser
                645                 650                 655
```

```
Thr Gly Glu Phe Asn Ile Ser Leu Leu Leu Lys Pro Pro Ser Ser Pro
            660                 665                 670

Ser Gly Arg Ser Phe Ile Glu Glu Leu Leu Phe Thr Ser Val Glu Thr
            675                 680                 685

Val Gly Leu Pro Thr Asp Ala Glu Tyr Lys Lys Cys Thr Ala Gly Pro
            690                 695                 700

Leu Gly Thr Leu Lys Asp Leu Ile Cys Ala Arg Glu Tyr Asn Gly Leu
705                 710                 715                 720

Leu Val Leu Pro Pro Ile Ile Thr Ala Asp Met Gln Thr Met Tyr Thr
                725                 730                 735

Ala Ser Leu Val Gly Ala Met Ala Phe Gly Gly Ile Thr Ser Ala Ala
            740                 745                 750

Ala Ile Pro Phe Ala Thr Gln Ile Gln Ala Arg Ile Asn His Leu Gly
            755                 760                 765

Ile Thr Gln Ser Leu Leu Met Lys Asn Gln Glu Lys Ile Ala Ala Ser
            770                 775                 780

Phe Asn Lys Ala Ile Gly His Met Gln Glu Gly Phe Arg Ser Thr Ser
785                 790                 795                 800

Leu Ala Leu Gln Gln Ile Gln Asp Val Val Asn Lys Gln Ser Ala Ile
            805                 810                 815

Leu Thr Glu Thr Met Asn Ser Leu Asn Lys Asn Phe Gly Ala Ile Thr
            820                 825                 830

Ser Val Ile Gln Asp Ile Tyr Ala Gln Leu Asp Ala Ile Gln Ala Asp
            835                 840                 845

Ala Gln Val Asp Arg Leu Ile Thr Gly Arg Leu Ser Ser Leu Ser Val
850                 855                 860

Leu Ala Ser Ala Lys Gln Ser Glu Tyr Ile Arg Val Ser Gln Gln Arg
865                 870                 875                 880

Glu Leu Ala Thr Gln Lys Ile Asn Glu Cys Val Lys Ser Gln Ser Asn
            885                 890                 895

Arg Tyr Gly Phe Cys Gly Ser Gly Arg His Val Leu Ser Ile Pro Gln
            900                 905                 910

Asn Ala Pro Asn Gly Ile Val Phe Ile His Phe Thr Tyr Thr Pro Glu
            915                 920                 925

Ser Phe Val Asn Val Thr Ala Ile Val Gly Phe Cys Val Asn Pro Ala
            930                 935                 940

Asn Ala Ser Gln Tyr Ala Ile Val Pro Ala Asn Gly Arg Gly Ile Phe
945                 950                 955                 960

Ile Gln Val Asn Gly Thr Tyr Tyr Ile Thr Ala Arg Asp Met Tyr Met
                965                 970                 975

Pro Arg Asp Ile Thr Ala Gly Asp Ile Val Thr Leu Thr Ser Cys Gln
            980                 985                 990

Ala Asn Tyr Val Asn Val Asn Lys Thr Val Ile Thr Thr Phe Val Glu
            995                 1000                1005

Asp Asp Asp Phe Asp Phe Asp Asp Glu Leu Ser Lys Trp Trp Asn
    1010                1015                1020

Asp Thr Lys His Gln Leu Pro Asp Phe Asp Asp Phe Asn Tyr Thr
    1025                1030                1035

Val Pro Ile Leu Asn Ile Ser Gly Glu Ile Asp Tyr Ile Gln Gly
    1040                1045                1050

Val Ile Gln Gly Leu Asn Asp Ser Leu Ile Asp Leu Glu Glu Leu
    1055                1060                1065

Ser Ile Ile Lys Thr Tyr Ile Lys Trp Pro
```

```
                                1070              1075

<210> SEQ ID NO 9
<211> LENGTH: 1166
<212> TYPE: PRT
<213> ORGANISM: Avian infectious bronchitis virus

<400> SEQUENCE: 9

Met Leu Gly Lys Ser Leu Phe Ile Val Thr Leu Phe Ala Leu Cys
1               5                   10                  15

Ser Ala Ala Leu Phe Asp Asn Asn Glu Thr Val Tyr Tyr Gln Ser
                20                  25                  30

Ala Phe Arg Pro Ala Asp Gly Trp His Leu His Gly Gly Ala Tyr Ala
            35                  40                  45

Val Val Asn Val Ser Leu Glu Thr Asn Asn Ala Gly Thr Ala Ser Gln
        50                  55                  60

Cys Ile Ala Gly Ala Ile Ser Trp Ser Lys Asn Phe Ser Ala Ser Ala
65                  70                  75                  80

Val Ala Met Thr Ala Pro Glu Leu Gly Met Thr Trp Ser Thr Gly Gln
                85                  90                  95

Phe Cys Thr Ala His Cys Asn Phe Ser Asp Phe Thr Val Phe Val Thr
            100                 105                 110

His Cys Phe Lys His Gly Asn Gly Leu Cys Pro Leu Thr Gly Leu Ile
        115                 120                 125

Pro Ser Gly Phe Ile Arg Val Ser Ala Met Arg Lys Gly Ser Asn Ser
130                 135                 140

Leu Phe Tyr Asn Leu Thr Val Ser Val Thr Lys Tyr Pro Arg Phe Lys
145                 150                 155                 160

Ser Leu Gln Cys Val Asn Asn Tyr Thr Ser Val Tyr Leu Asn Gly Asp
                165                 170                 175

Leu Val Phe Thr Ser Asn Glu Thr Lys Pro Val Ser Ala Ala Gly Val
            180                 185                 190

Ser Phe Lys Ala Gly Gly Pro Ile Thr Tyr Lys Thr Met Ser Glu Val
        195                 200                 205

Lys Val Leu Ala Tyr Phe Val Asn Gly Thr Ala Gln Thr Val Ile Pro
210                 215                 220

Cys Asp Gly Ser Pro Arg Gly Leu Leu Ala Cys Gln Tyr Asn Thr Gly
225                 230                 235                 240

Asn Phe Ser Asp Gly Phe Tyr Pro Tyr Thr Asn Ser Ser Leu Val Lys
                245                 250                 255

Glu Arg Phe Ile Val Tyr Arg Glu Ser Ser Val Asn Thr Thr Leu Val
            260                 265                 270

Leu Thr Asn Phe Thr Phe Ser Asn Val Ser Asn Ala Pro Pro Asn Thr
        275                 280                 285

Gly Gly Val His Ser Ile Val Leu His Gln Thr Gln Thr Ala Gln Ser
290                 295                 300

Gly Tyr Tyr Asn Phe Asn Phe Ser Phe Leu Ser Ser Phe Arg Tyr Val
305                 310                 315                 320

Glu Ser Asp Phe Met Tyr Gly Ser Tyr His Pro Lys Cys Ser Phe Arg
                325                 330                 335

Leu Glu Thr Ile Asn Asn Gly Leu Trp Phe Asn Ser Leu Ser Val Ser
            340                 345                 350

Leu Gly Tyr Gly Pro Leu Gln Gly Gly Cys Lys Gln Ser Val Phe Asn
        355                 360                 365
```

-continued

```
Asn Met Ala Thr Cys Cys Tyr Ala Tyr Ser Tyr Ser Gly Pro Thr Leu
    370                 375                 380
Cys Lys Gly Val Tyr Ser Gly Gln Leu Gln Lys Thr Phe Glu Cys Gly
385                 390                 395                 400
Leu Leu Val Phe Val Thr Lys Ser Asp Gly Ser Arg Ile Gln Thr Arg
                405                 410                 415
Asn Glu Pro Leu Val Leu Thr Gln His Asn Tyr Asn Asn Ile Thr Leu
            420                 425                 430
Asn Lys Cys Val Glu Tyr Asn Ile Tyr Gly Arg Val Gly Gln Gly Leu
        435                 440                 445
Ile Thr Asn Ile Thr Asp Ser Ala Ala Asn His Gly Tyr Leu Ala Asp
450                 455                 460
Gly Gly Leu Ala Val Leu Asp Thr Ser Gly Ala Ile Asp Val Phe Val
465                 470                 475                 480
Val Gln Gly Val Tyr Gly Leu Thr Tyr Tyr Lys Val Asn Pro Cys Glu
                485                 490                 495
Asp Val Asn Gln Gln Phe Val Val Ser Gly Gln Leu Val Gly Ile
            500                 505                 510
Leu Thr Ser Arg Asn Glu Thr Gly Ser Gln Pro Ile Glu Asn Arg Phe
        515                 520                 525
Tyr Val Lys Phe Pro Asn Ser Arg Arg Arg Thr Gly Arg Ser Thr Ile
530                 535                 540
Ala Asn Val Thr Asn Cys Pro Tyr Val Ser Tyr Gly Lys Phe Cys Ile
545                 550                 555                 560
Lys Pro Asp Gly Ser Val Ser Glu Ile Val Pro Gln Glu Ile Glu His
                565                 570                 575
Phe Val Ala Pro Leu Leu Asn Val Thr Glu His Val Leu Ile Pro Asn
            580                 585                 590
Ser Phe Asn Leu Thr Val Thr Asp Glu Tyr Ile Gln Thr Arg Met Asp
        595                 600                 605
Lys Ile Gln Ile Asn Cys Arg Gln Tyr Val Cys Gly Asn Ser Ile Glu
610                 615                 620
Cys Arg Lys Leu Phe Gln Gln Tyr Gly Pro Val Cys Asp Asn Ile Leu
625                 630                 635                 640
Ser Val Val Asn Thr Val Gly Gln Arg Glu Asp Met Glu Leu Leu Ser
                645                 650                 655
Phe Tyr Ser Ser Thr Lys Pro Lys Asp Tyr Asn Ile Pro Ile Phe Ser
            660                 665                 670
Asn Val Ser Thr Gly Asp Phe Asn Ile Ser Leu Leu Leu Thr Pro Pro
        675                 680                 685
Asn Ser Pro Thr Gly Arg Ser Phe Ile Glu Asp Ile Leu Phe Thr Ser
690                 695                 700
Val Glu Ser Val Gly Leu Pro Thr Asp Glu Glu Tyr Lys Lys Cys Thr
705                 710                 715                 720
Ala Gly Pro Leu Gly Phe Val Lys Asp Leu Val Cys Ala Arg Glu Tyr
                725                 730                 735
Asn Gly Leu Leu Val Leu Pro Pro Ile Ile Thr Ala Asp Met Gln Thr
            740                 745                 750
Met Tyr Thr Ser Thr Leu Val Ala Ser Met Ala Leu Gly Gly Ile Thr
        755                 760                 765
Ala Ala Gly Ala Ile Pro Phe Ala Thr Gln Leu Gln Ala Arg Ile Asn
770                 775                 780
His Leu Gly Ile Thr Gln Ser Leu Leu Leu Lys Asn Gln Glu Lys Ile
```

```
              785                 790                 795                 800
Ala Ala Ser Phe Asn Lys Ala Ile Gly His Met Gln Glu Gly Phe Arg
                805                 810                 815

Ser Thr Ser Leu Ala Leu Gln Gln Ile Gln Asp Val Val Asn Lys Gln
                820                 825                 830

Ser Ser Ile Leu Thr Glu Thr Met Ala Ser Leu Asn Lys Asn Phe Gly
                835                 840                 845

Ala Ile Ser Ser Val Leu Gln Asp Ile Tyr Gln Gln Leu Asp Ala Ile
            850                 855                 860

Gln Ala Asp Ala Gln Val Asp Arg Ile Ile Thr Gly Arg Leu Ser Ser
865                 870                 875                 880

Leu Ser Val Leu Ala Ser Ala Lys Gln Ser Glu Tyr Tyr Arg Val Ser
                885                 890                 895

Gln Gln Arg Glu Leu Ala Thr Gln Lys Ile Asn Glu Cys Val Lys Ser
                900                 905                 910

Gln Ser Thr Arg Tyr Ser Phe Cys Gly Asn Gly Arg His Val Leu Thr
                915                 920                 925

Ile Pro Gln Asn Ala Pro Asn Gly Ile Val Phe Ile His Phe Thr Tyr
            930                 935                 940

Thr Pro Glu Ser Phe Val Asn Val Thr Ala Ile Val Gly Phe Cys Val
945                 950                 955                 960

Asn Pro Pro Asn Ala Ser Gln Tyr Ala Leu Val Pro Ala Asn Gly Arg
                965                 970                 975

Gly Ile Phe Ile Gln Val Asn Gly Ser Tyr Tyr Ile Thr Ala Arg Asp
                980                 985                 990

Met Tyr Met Pro Arg Asp Ile Thr Ala Gly Asp Ile Val Thr Leu Thr
                995                 1000                1005

Ser Cys Gln Ala Asn Tyr Val Ser Val Asn Arg Thr Val Ile Thr
            1010                1015                1020

Thr Phe Val Asp Asn Asp Asp Phe Asp Phe Asp Asp Glu Leu Ser
            1025                1030                1035

Lys Trp Trp Asn Asp Thr Lys His Glu Leu Pro Asp Phe Asp Glu
            1040                1045                1050

Phe Asn Tyr Thr Ile Pro Val Leu Asn Ile Ser Asn Glu Ile Asp
            1055                1060                1065

Arg Ile Gln Glu Val Ile Gln Gly Leu Asn Asp Ser Leu Ile Asp
            1070                1075                1080

Leu Glu Ala Leu Ser Ile Leu Lys Thr Tyr Ile Lys Trp Pro Trp
            1085                1090                1095

Tyr Val Trp Leu Ala Ile Ala Phe Leu Thr Ile Ile Phe Ile Leu
            1100                1105                1110

Val Leu Cys Trp Ile Phe Phe Met Thr Gly Cys Cys Gly Cys Cys
            1115                1120                1125

Cys Gly Cys Phe Gly Ile Met Pro Leu Met Ser Lys Cys Gly Lys
            1130                1135                1140

Lys Ser Ser Tyr Tyr Thr Thr Phe Asp Asn Asp Val Val Thr Glu
            1145                1150                1155

Gln Tyr Arg Pro Lys Lys Ser Val
            1160                1165

<210> SEQ ID NO 10
<211> LENGTH: 1079
<212> TYPE: PRT
<213> ORGANISM: Avian infectious bronchitis virus
```

<400> SEQUENCE: 10

Ala Leu Phe Asp Asn Asn Glu Thr Val Tyr Tyr Gln Ser Ala Phe
1               5                   10                  15

Arg Pro Ala Asp Gly Trp His Leu His Gly Ala Tyr Ala Val Val
            20                  25                  30

Asn Val Ser Leu Glu Thr Asn Asn Ala Gly Thr Ala Ser Gln Cys Ile
            35                  40                  45

Ala Gly Ala Ile Ser Trp Ser Lys Asn Phe Ser Ala Ser Ala Val Ala
        50                  55                  60

Met Thr Ala Pro Glu Leu Gly Met Thr Trp Ser Thr Gly Gln Phe Cys
65                  70                  75                  80

Thr Ala His Cys Asn Phe Ser Asp Phe Thr Val Phe Val Thr His Cys
                85                  90                  95

Phe Lys His Gly Asn Gly Leu Cys Pro Leu Thr Gly Leu Ile Pro Ser
            100                 105                 110

Gly Phe Ile Arg Val Ser Ala Met Arg Lys Gly Ser Asn Ser Leu Phe
            115                 120                 125

Tyr Asn Leu Thr Val Ser Val Thr Lys Tyr Pro Arg Phe Lys Ser Leu
130                 135                 140

Gln Cys Val Asn Asn Tyr Thr Ser Val Tyr Leu Asn Gly Asp Leu Val
145                 150                 155                 160

Phe Thr Ser Asn Glu Thr Lys Pro Val Ser Ala Ala Gly Val Ser Phe
                165                 170                 175

Lys Ala Gly Gly Pro Ile Thr Tyr Lys Thr Met Ser Glu Val Lys Val
            180                 185                 190

Leu Ala Tyr Phe Val Asn Gly Thr Ala Gln Thr Val Ile Pro Cys Asp
            195                 200                 205

Gly Ser Pro Arg Gly Leu Leu Ala Cys Gln Tyr Asn Thr Gly Asn Phe
210                 215                 220

Ser Asp Gly Phe Tyr Pro Tyr Thr Asn Ser Ser Leu Val Lys Glu Arg
225                 230                 235                 240

Phe Ile Val Tyr Arg Glu Ser Ser Val Asn Thr Thr Leu Val Leu Thr
            245                 250                 255

Asn Phe Thr Phe Ser Asn Val Ser Asn Ala Pro Pro Asn Thr Gly Gly
            260                 265                 270

Val His Ser Ile Val Leu His Gln Thr Gln Thr Ala Gln Ser Gly Tyr
            275                 280                 285

Tyr Asn Phe Asn Phe Ser Phe Leu Ser Ser Phe Arg Tyr Val Glu Ser
            290                 295                 300

Asp Phe Met Tyr Gly Ser Tyr His Pro Lys Cys Ser Phe Arg Leu Glu
305                 310                 315                 320

Thr Ile Asn Asn Gly Leu Trp Phe Asn Ser Leu Ser Val Ser Leu Gly
            325                 330                 335

Tyr Gly Pro Leu Gln Gly Gly Cys Lys Gln Ser Val Phe Asn Asn Met
            340                 345                 350

Ala Thr Cys Cys Tyr Ala Tyr Ser Tyr Ser Gly Pro Thr Leu Cys Lys
            355                 360                 365

Gly Val Tyr Ser Gly Gln Leu Gln Lys Thr Phe Glu Cys Gly Leu Leu
            370                 375                 380

Val Phe Val Thr Lys Ser Asp Gly Ser Arg Ile Gln Thr Arg Asn Glu
385                 390                 395                 400

Pro Leu Val Leu Thr Gln His Asn Tyr Asn Asn Ile Thr Leu Asn Lys

-continued

```
                405                 410                 415
    Cys Val Glu Tyr Asn Ile Tyr Gly Arg Val Gly Gln Gly Leu Ile Thr
                    420                 425                 430

Asn Ile Thr Asp Ser Ala Ala Asn His Gly Tyr Leu Ala Asp Gly Gly
                435                 440                 445

Leu Ala Val Leu Asp Thr Ser Gly Ala Ile Asp Val Phe Val Val Gln
    450                 455                 460

Gly Val Tyr Gly Leu Thr Tyr Tyr Lys Val Asn Pro Cys Glu Asp Val
    465                 470                 475                 480

Asn Gln Gln Phe Val Val Ser Gly Gln Leu Val Gly Ile Leu Thr
                    485                 490                 495

Ser Arg Asn Glu Thr Gly Ser Gln Pro Ile Glu Asn Arg Phe Tyr Val
                    500                 505                 510

Lys Phe Pro Asn Ser Arg Arg Thr Gly Arg Ser Thr Ile Ala Asn
                515                 520                 525

Val Thr Asn Cys Pro Tyr Val Ser Tyr Gly Lys Phe Cys Ile Lys Pro
                530                 535                 540

Asp Gly Ser Val Ser Glu Ile Val Pro Gln Glu Ile Glu His Phe Val
    545                 550                 555                 560

Ala Pro Leu Leu Asn Val Thr Glu His Val Leu Ile Pro Asn Ser Phe
                    565                 570                 575

Asn Leu Thr Val Thr Asp Glu Tyr Ile Gln Thr Arg Met Asp Lys Ile
                    580                 585                 590

Gln Ile Asn Cys Arg Gln Tyr Val Cys Gly Asn Ser Ile Glu Cys Arg
                    595                 600                 605

Lys Leu Phe Gln Gln Tyr Gly Pro Val Cys Asp Asn Ile Leu Ser Val
                610                 615                 620

Val Asn Thr Val Gly Gln Arg Glu Asp Met Glu Leu Leu Ser Phe Tyr
    625                 630                 635                 640

Ser Ser Thr Lys Pro Lys Asp Tyr Asn Ile Pro Ile Phe Ser Asn Val
                    645                 650                 655

Ser Thr Gly Asp Phe Asn Ile Ser Leu Leu Leu Thr Pro Pro Asn Ser
                    660                 665                 670

Pro Thr Gly Arg Ser Phe Ile Glu Asp Ile Leu Phe Thr Ser Val Glu
                675                 680                 685

Ser Val Gly Leu Pro Thr Asp Glu Glu Tyr Lys Lys Cys Thr Ala Gly
                690                 695                 700

Pro Leu Gly Phe Val Lys Asp Leu Val Cys Ala Arg Glu Tyr Asn Gly
    705                 710                 715                 720

Leu Leu Val Leu Pro Pro Ile Ile Thr Ala Asp Met Gln Thr Met Tyr
                    725                 730                 735

Thr Ser Thr Leu Val Ala Ser Met Ala Leu Gly Gly Ile Thr Ala Ala
                    740                 745                 750

Gly Ala Ile Pro Phe Ala Thr Gln Leu Gln Ala Arg Ile Asn His Leu
                755                 760                 765

Gly Ile Thr Gln Ser Leu Leu Leu Lys Asn Gln Glu Lys Ile Ala Ala
    770                 775                 780

Ser Phe Asn Lys Ala Ile Gly His Met Gln Glu Gly Phe Arg Ser Thr
    785                 790                 795                 800

Ser Leu Ala Leu Gln Gln Ile Gln Asp Val Val Asn Lys Gln Ser Ser
                    805                 810                 815

Ile Leu Thr Glu Thr Met Ala Ser Leu Asn Lys Asn Phe Gly Ala Ile
                    820                 825                 830
```

```
Ser Ser Val Leu Gln Asp Ile Tyr Gln Gln Leu Asp Ala Ile Gln Ala
        835                 840                 845

Asp Ala Gln Val Asp Arg Ile Ile Thr Gly Arg Leu Ser Ser Leu Ser
850                 855                 860

Val Leu Ala Ser Ala Lys Gln Ser Glu Tyr Tyr Arg Val Ser Gln Gln
865                 870                 875                 880

Arg Glu Leu Ala Thr Gln Lys Ile Asn Glu Cys Val Lys Ser Gln Ser
                885                 890                 895

Thr Arg Tyr Ser Phe Cys Gly Asn Gly Arg His Val Leu Thr Ile Pro
            900                 905                 910

Gln Asn Ala Pro Asn Gly Ile Val Phe Ile His Phe Thr Tyr Thr Pro
        915                 920                 925

Glu Ser Phe Val Asn Val Thr Ala Ile Val Gly Phe Cys Val Asn Pro
930                 935                 940

Pro Asn Ala Ser Gln Tyr Ala Leu Val Pro Ala Asn Gly Arg Gly Ile
945                 950                 955                 960

Phe Ile Gln Val Asn Gly Ser Tyr Tyr Ile Thr Ala Arg Asp Met Tyr
                965                 970                 975

Met Pro Arg Asp Ile Thr Ala Gly Asp Ile Val Thr Leu Thr Ser Cys
            980                 985                 990

Gln Ala Asn Tyr Val Ser Val Asn Arg Thr Val Ile Thr Thr Phe Val
        995                 1000                1005

Asp Asn Asp Asp Phe Asp Phe Asp Asp Glu Leu Ser Lys Trp Trp
        1010                1015                1020

Asn Asp Thr Lys His Glu Leu Pro Asp Phe Asp Glu Phe Asn Tyr
        1025                1030                1035

Thr Ile Pro Val Leu Asn Ile Ser Asn Glu Ile Asp Arg Ile Gln
        1040                1045                1050

Glu Val Ile Gln Gly Leu Asn Asp Ser Leu Ile Asp Leu Glu Ala
        1055                1060                1065

Leu Ser Ile Leu Lys Thr Tyr Ile Lys Trp Pro
        1070                1075

<210> SEQ ID NO 11
<211> LENGTH: 1159
<212> TYPE: PRT
<213> ORGANISM: Avian infectious bronchitis virus

<400> SEQUENCE: 11

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Ala Gly Thr Ala Pro Ser
    50                  55                  60

Cys Thr Ala Gly Ala Ile Gly Tyr Ser Lys Asn Phe Ser Ala Ala Ser
65                  70                  75                  80

Val Ala Met Thr Ala Pro Leu Ser Gly Met Ser Trp Ser Ala Ser Ser
                85                  90                  95

Phe Cys Thr Ala His Cys Asn Phe Thr Ser Tyr Ile Val Phe Val Thr
            100                 105                 110

His Cys Phe Lys Ser Gly Ser Asn Ser Cys Pro Leu Thr Gly Leu Ile
```

```
            115                 120                 125
Pro Ser Gly Tyr Ile Arg Ile Ala Ala Met Lys His Gly Ser Arg Thr
            130                 135                 140
Pro Gly His Leu Phe Tyr Asn Leu Thr Val Ser Val Thr Lys Tyr Pro
145                 150                 155                 160
Lys Phe Arg Ser Leu Gln Cys Val Asn Asn His Thr Ser Val Tyr Leu
                165                 170                 175
Asn Gly Asp Leu Val Phe Thr Ser Gly Tyr Thr Glu Asp Val Val Ala
            180                 185                 190
Ala Gly Val His Phe Lys Ser Gly Pro Ile Thr Tyr Lys Val Met
            195                 200                 205
Arg Glu Val Lys Ala Leu Ala Tyr Phe Val Asn Gly Thr Ala His Asp
            210                 215                 220
Val Ile Leu Cys Asp Asp Thr Pro Arg Gly Leu Leu Ala Cys Gln Tyr
225                 230                 235                 240
Asn Thr Gly Asn Phe Ser Asp Gly Phe Tyr Pro Phe Thr Asn Thr Ser
                245                 250                 255
Ile Val Lys Asp Lys Phe Ile Val Tyr Arg Glu Ser Ser Val Asn Thr
            260                 265                 270
Thr Leu Thr Leu Thr Asn Phe Thr Phe Ser Asn Glu Ser Gly Ala Pro
            275                 280                 285
Pro Asn Thr Gly Gly Val Asp Ser Phe Ile Leu Tyr Gln Thr Gln Thr
290                 295                 300
Ala Gln Ser Gly Tyr Tyr Asn Phe Asn Phe Ser Phe Leu Ser Ser Phe
305                 310                 315                 320
Val Tyr Arg Glu Ser Asn Tyr Met Tyr Gly Ser Tyr His Pro Arg Cys
                325                 330                 335
Ser Phe Arg Pro Glu Thr Leu Asn Gly Leu Trp Phe Asn Ser Leu Ser
            340                 345                 350
Val Ser Leu Thr Tyr Gly Pro Ile Gln Gly Gly Cys Lys Gln Ser Val
            355                 360                 365
Phe Asn Gly Lys Ala Thr Cys Cys Tyr Ala Tyr Ser Tyr Gly Gly Pro
370                 375                 380
Arg Ala Cys Lys Gly Val Tyr Arg Gly Glu Leu Thr Gln His Phe Glu
385                 390                 395                 400
Cys Gly Leu Leu Val Tyr Val Thr Lys Ser Asp Gly Ser Arg Ile Gln
                405                 410                 415
Thr Ala Thr Gln Pro Pro Val Leu Thr Gln Asn Phe Tyr Asn Asn Ile
            420                 425                 430
Thr Leu Gly Lys Cys Val Asp Tyr Asn Val Tyr Gly Arg Thr Gly Gln
            435                 440                 445
Gly Phe Ile Thr Asn Val Thr Asp Leu Ala Thr Ser His Asn Tyr Leu
            450                 455                 460
Ala Asp Gly Gly Leu Ala Ile Leu Asp Thr Ser Gly Ala Ile Asp Ile
465                 470                 475                 480
Phe Val Val Gln Gly Glu Tyr Gly Pro Asn Tyr Tyr Lys Val Asn Leu
                485                 490                 495
Cys Glu Asp Val Asn Gln Gln Phe Val Val Ser Gly Gly Lys Leu Val
            500                 505                 510
Gly Ile Leu Thr Ser Arg Asn Glu Thr Gly Ser Gln Pro Leu Glu Asn
            515                 520                 525
Gln Phe Tyr Ile Lys Ile Thr Asn Gly Thr His Arg Ser Arg Arg Ser
            530                 535                 540
```

```
Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
                565                 570                 575

Glu Gln Phe Val Ala Pro Leu Leu Asn Val Thr Glu Asn Val Leu Ile
            580                 585                 590

Pro Asn Ser Phe Asn Leu Thr Val Thr Asp Glu Tyr Ile Gln Thr His
        595                 600                 605

Met Asp Lys Ile Gln Ile Asn Cys Leu Gln Tyr Val Cys Gly Asn Ser
    610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                645                 650                 655

Leu Ser Phe Tyr Ser Ser Thr Lys Pro Ser Gly Phe Asn Thr Pro Val
            660                 665                 670

Phe Ser Asn Leu Ser Thr Gly Glu Phe Asn Ile Ser Leu Leu Leu Thr
        675                 680                 685

Thr Pro Ser Ser Pro Arg Gly Arg Ser Phe Ile Glu Asp Leu Leu Phe
    690                 695                 700

Thr Ser Val Glu Ser Val Gly Leu Pro Thr Asp Glu Ala Tyr Lys Lys
705                 710                 715                 720

Cys Thr Ala Gly Pro Leu Gly Phe Leu Lys Asp Leu Ala Cys Ala Arg
                725                 730                 735

Glu Tyr Asn Gly Leu Leu Val Leu Pro Pro Ile Ile Thr Ala Glu Met
            740                 745                 750

Gln Thr Leu Tyr Thr Ser Ser Leu Val Val Ser Met Ala Phe Gly Gly
        755                 760                 765

Ile Thr Ser Ala Gly Ala Ile Pro Phe Ala Thr Gln Leu Gln Ala Arg
    770                 775                 780

Ile Asn His Leu Gly Ile Thr Gln Ser Leu Leu Leu Lys Asn Gln Glu
785                 790                 795                 800

Lys Ile Ala Ala Ser Phe Asn Lys Ala Ile Gly His Met Gln Glu Gly
                805                 810                 815

Phe Arg Ser Thr Ser Leu Ala Leu Gln Gln Ile Gln Asp Val Val Asn
            820                 825                 830

Lys Gln Ser Ala Ile Leu Thr Glu Thr Met Ala Ser Leu Asn Lys Asn
        835                 840                 845

Phe Gly Ala Ile Ser Ser Val Ile Gln Glu Ile Tyr Gln Gln Leu Asp
    850                 855                 860

Ala Ile Gln Ala Asn Ala Gln Val Asp Arg Leu Ile Thr Gly Arg Leu
865                 870                 875                 880

Ser Ser Leu Ser Val Leu Ala Ser Ala Lys Gln Ala Glu Tyr Ile Arg
                885                 890                 895

Val Ser Gln Gln Arg Glu Leu Ala Thr Gln Lys Ile Asn Glu Cys Val
            900                 905                 910

Lys Ser Gln Ser Ile Arg Tyr Ser Phe Cys Gly Asn Gly Arg His Val
        915                 920                 925

Leu Thr Ile Pro Gln Asn Ala Pro Asn Gly Ile Val Phe Ile His Phe
    930                 935                 940

Ser Tyr Thr Pro Asp Ser Phe Val Asn Val Thr Ala Ile Val Gly Phe
945                 950                 955                 960
```

```
Cys Val Lys Pro Ala Asn Ala Ser Gln Tyr Ala Ile Val Pro Ala Asn
                965                 970                 975

Gly Arg Gly Ile Phe Ile Gln Val Asn Gly Ser Tyr Tyr Ile Thr Ala
            980                 985                 990

Arg Asp Met Tyr Met Pro Arg Ala Ile Thr Ala Gly Asp Ile Val Thr
        995                 1000                1005

Leu Thr Ser Cys Gln Ala Asn Tyr Val Ser Val Asn Lys Thr Val
    1010                1015                1020

Ile Thr Thr Phe Val Asp Asn Asp Asp Phe Asp Phe Asn Asp Glu
    1025                1030                1035

Leu Ser Lys Trp Trp Asn Asp Thr Lys His Glu Leu Pro Asp Phe
    1040                1045                1050

Asp Lys Phe Asn Tyr Thr Val Pro Ile Leu Asp Ile Asp Ser Glu
    1055                1060                1065

Ile Asp Arg Ile Gln Gly Val Ile Gln Gly Leu Asn Asp Ser Leu
    1070                1075                1080

Ile Asp Leu Glu Lys Leu Ser Ile Leu Lys Thr Tyr Ile Lys Trp
    1085                1090                1095

Pro Trp Tyr Val Trp Leu Ala Ile Ala Phe Ala Thr Ile Ile Phe
    1100                1105                1110

Ile Leu Ile Leu Gly Trp Val Phe Phe Met Thr Gly Cys Cys Gly
    1115                1120                1125

Cys Cys Cys Gly Cys Phe Gly Ile Met Pro Leu Met Ser Lys Cys
    1130                1135                1140

Gly Lys Lys Ser Ser Tyr Tyr Thr Thr Phe Asp Asn Asp Val Val
    1145                1150                1155

Thr

<210> SEQ ID NO 12
<211> LENGTH: 1081
<212> TYPE: PRT
<213> ORGANISM: Avian infectious bronchitis virus

<400> SEQUENCE: 12

Asn Leu Tyr Asp Asn Glu Ser Phe Val Tyr Tyr Gln Ser Ala Phe
1               5                   10                  15

Arg Pro Gly His Gly Trp His Leu His Gly Gly Ala Tyr Ala Val Val
            20                  25                  30

Asn Val Ser Ser Glu Asn Asn Asn Ala Gly Thr Ala Pro Ser Cys Thr
        35                  40                  45

Ala Gly Ala Ile Gly Tyr Ser Lys Asn Phe Ser Ala Ala Ser Val Ala
    50                  55                  60

Met Thr Ala Pro Leu Ser Gly Met Ser Trp Ser Ala Ser Ser Phe Cys
65                  70                  75                  80

Thr Ala His Cys Asn Phe Thr Ser Tyr Ile Val Phe Val Thr His Cys
                85                  90                  95

Phe Lys Ser Gly Ser Asn Ser Cys Pro Leu Thr Gly Leu Ile Pro Ser
            100                 105                 110

Gly Tyr Ile Arg Ile Ala Ala Met Lys His Gly Ser Arg Thr Pro Gly
        115                 120                 125

His Leu Phe Tyr Asn Leu Thr Val Ser Val Thr Lys Tyr Pro Lys Phe
    130                 135                 140

Arg Ser Leu Gln Cys Val Asn Asn His Thr Ser Val Tyr Leu Asn Gly
145                 150                 155                 160
```

```
Asp Leu Val Phe Thr Ser Gly Tyr Thr Glu Asp Val Ala Ala Gly
            165                 170                 175

Val His Phe Lys Ser Gly Gly Pro Ile Thr Tyr Lys Val Met Arg Glu
        180                 185                 190

Val Lys Ala Leu Ala Tyr Phe Val Asn Gly Thr Ala His Asp Val Ile
            195                 200                 205

Leu Cys Asp Asp Thr Pro Arg Gly Leu Leu Ala Cys Gln Tyr Asn Thr
        210                 215                 220

Gly Asn Phe Ser Asp Gly Phe Tyr Pro Phe Thr Asn Thr Ser Ile Val
225                 230                 235                 240

Lys Asp Lys Phe Ile Val Tyr Arg Glu Ser Ser Val Asn Thr Thr Leu
            245                 250                 255

Thr Leu Thr Asn Phe Thr Phe Ser Asn Glu Ser Gly Ala Pro Pro Asn
        260                 265                 270

Thr Gly Gly Val Asp Ser Phe Ile Leu Tyr Gln Thr Gln Thr Ala Gln
            275                 280                 285

Ser Gly Tyr Tyr Asn Phe Asn Phe Ser Phe Leu Ser Ser Phe Val Tyr
        290                 295                 300

Arg Glu Ser Asn Tyr Met Tyr Gly Ser Tyr His Pro Arg Cys Ser Phe
305                 310                 315                 320

Arg Pro Glu Thr Leu Asn Gly Leu Trp Phe Asn Ser Leu Ser Val Ser
            325                 330                 335

Leu Thr Tyr Gly Pro Ile Gln Gly Gly Cys Lys Gln Ser Val Phe Asn
        340                 345                 350

Gly Lys Ala Thr Cys Cys Tyr Ala Tyr Ser Tyr Gly Gly Pro Arg Ala
            355                 360                 365

Cys Lys Gly Val Tyr Arg Gly Glu Leu Thr Gln His Phe Glu Cys Gly
370                 375                 380

Leu Leu Val Tyr Val Thr Lys Ser Asp Gly Ser Arg Ile Gln Thr Ala
            385                 390                 395                 400

Thr Gln Pro Pro Val Leu Thr Gln Asn Phe Tyr Asn Asn Ile Thr Leu
        405                 410                 415

Gly Lys Cys Val Asp Tyr Asn Val Tyr Gly Arg Thr Gly Gln Gly Phe
            420                 425                 430

Ile Thr Asn Val Thr Asp Leu Ala Thr Ser His Asn Tyr Leu Ala Asp
        435                 440                 445

Gly Gly Leu Ala Ile Leu Asp Thr Ser Gly Ala Ile Asp Ile Phe Val
450                 455                 460

Val Gln Gly Glu Tyr Gly Pro Asn Tyr Tyr Lys Val Asn Leu Cys Glu
465                 470                 475                 480

Asp Val Asn Gln Gln Phe Val Val Ser Gly Gly Lys Leu Val Gly Ile
            485                 490                 495

Leu Thr Ser Arg Asn Glu Thr Gly Ser Gln Pro Leu Glu Asn Gln Phe
        500                 505                 510

Tyr Ile Lys Ile Thr Asn Gly Thr His Arg Ser Arg Arg Ser Val Asn
            515                 520                 525

Glu Asn Val Thr Asn Cys Pro Tyr Val Ser Tyr Gly Lys Phe Cys Ile
        530                 535                 540

Lys Pro Asp Gly Ser Val Ser Pro Ile Val Pro Lys Glu Leu Glu Gln
545                 550                 555                 560

Phe Val Ala Pro Leu Leu Asn Val Thr Glu Asn Val Leu Ile Pro Asn
            565                 570                 575

Ser Phe Asn Leu Thr Val Thr Asp Glu Tyr Ile Gln Thr His Met Asp
```

```
                580                  585                  590
    Lys Ile Gln Ile Asn Cys Leu Gln Tyr Val Cys Gly Asn Ser Leu Ala
                    595                  600                  605
    Cys Arg Lys Leu Phe Gln Gln Tyr Gly Pro Val Cys Asp Asn Ile Leu
        610                  615                  620
    Ser Val Val Asn Ser Val Gly Gln Lys Glu Asp Met Glu Leu Leu Ser
    625                  630                  635                  640
    Phe Tyr Ser Ser Thr Lys Pro Ser Gly Phe Asn Thr Pro Val Phe Ser
                    645                  650                  655
    Asn Leu Ser Thr Gly Glu Phe Asn Ile Ser Leu Leu Leu Thr Thr Pro
                660                  665                  670
    Ser Ser Pro Arg Gly Arg Ser Phe Ile Glu Asp Leu Leu Phe Thr Ser
            675                  680                  685
    Val Glu Ser Val Gly Leu Pro Thr Asp Glu Ala Tyr Lys Lys Cys Thr
        690                  695                  700
    Ala Gly Pro Leu Gly Phe Leu Lys Asp Leu Ala Cys Ala Arg Glu Tyr
    705                  710                  715                  720
    Asn Gly Leu Leu Val Leu Pro Pro Ile Ile Thr Ala Glu Met Gln Thr
                    725                  730                  735
    Leu Tyr Thr Ser Ser Leu Val Val Ser Met Ala Phe Gly Gly Ile Thr
                740                  745                  750
    Ser Ala Gly Ala Ile Pro Phe Ala Thr Gln Leu Gln Ala Arg Ile Asn
            755                  760                  765
    His Leu Gly Ile Thr Gln Ser Leu Leu Leu Lys Asn Gln Glu Lys Ile
        770                  775                  780
    Ala Ala Ser Phe Asn Lys Ala Ile Gly His Met Gln Glu Gly Phe Arg
    785                  790                  795                  800
    Ser Thr Ser Leu Ala Leu Gln Gln Ile Gln Asp Val Val Asn Lys Gln
                    805                  810                  815
    Ser Ala Ile Leu Thr Glu Thr Met Ala Ser Leu Asn Lys Asn Phe Gly
                820                  825                  830
    Ala Ile Ser Ser Val Ile Gln Glu Ile Tyr Gln Gln Leu Asp Ala Ile
            835                  840                  845
    Gln Ala Asn Ala Gln Val Asp Arg Leu Ile Thr Gly Arg Leu Ser Ser
        850                  855                  860
    Leu Ser Val Leu Ala Ser Ala Lys Gln Ala Glu Tyr Ile Arg Val Ser
    865                  870                  875                  880
    Gln Gln Arg Glu Leu Ala Thr Gln Lys Ile Asn Glu Cys Val Lys Ser
                    885                  890                  895
    Gln Ser Ile Arg Tyr Ser Phe Cys Gly Asn Gly Arg His Val Leu Thr
                900                  905                  910
    Ile Pro Gln Asn Ala Pro Asn Gly Ile Val Phe Ile His Phe Ser Tyr
            915                  920                  925
    Thr Pro Asp Ser Phe Val Asn Val Thr Ala Ile Val Gly Phe Cys Val
        930                  935                  940
    Lys Pro Ala Asn Ala Ser Gln Tyr Ala Ile Val Pro Ala Asn Gly Arg
    945                  950                  955                  960
    Gly Ile Phe Ile Gln Val Asn Gly Ser Tyr Tyr Ile Thr Ala Arg Asp
                    965                  970                  975
    Met Tyr Met Pro Arg Ala Ile Thr Ala Gly Asp Ile Val Thr Leu Thr
                980                  985                  990
    Ser Cys Gln Ala Asn Tyr Val Ser Val Asn Lys Thr Val Ile Thr Thr
            995                  1000                 1005
```

```
Phe Val Asp Asn Asp Asp Phe Asp Phe Asn Asp Glu Leu Ser Lys
    1010                1015                1020

Trp Trp Asn Asp Thr Lys His Glu Leu Pro Asp Phe Asp Lys Phe
    1025                1030                1035

Asn Tyr Thr Val Pro Ile Leu Asp Ile Asp Ser Glu Ile Asp Arg
    1040                1045                1050

Ile Gln Gly Val Ile Gln Gly Leu Asn Asp Ser Leu Ile Asp Leu
    1055                1060                1065

Glu Lys Leu Ser Ile Leu Lys Thr Tyr Ile Lys Trp Pro
    1070                1075                1080

<210> SEQ ID NO 13
<211> LENGTH: 1156
<212> TYPE: PRT
<213> ORGANISM: Avian infectious bronchitis virus

<400> SEQUENCE: 13

Met Leu Val Lys Ser Leu Phe Ile Val Thr Leu Leu Phe Ala Leu Cys
1               5                   10                  15

Ser Ala Ala Leu Phe Asp Asn Asn Gln Ala Val Tyr Tyr Tyr Gln Ser
                20                  25                  30

Ala Phe Arg Pro Ser Ser Gly Trp His Lys His Gly Gly Ala Tyr Ala
            35                  40                  45

Val Ala Asn Val Ser Leu Glu Tyr Ala Asn Ala Gly Ser Ser Thr His
        50                  55                  60

Cys Thr Ala Gly Ala Ile Tyr Trp Ser Lys Asn Phe Thr Ala Ser Ser
65                  70                  75                  80

Val Ala Met Thr Ala Pro Gly Thr Gly Met Ser Trp Ser Thr Ala Gln
                85                  90                  95

Phe Cys Thr Ala His Cys Asn Phe Ser Asp Phe Thr Val Phe Val Thr
                100                 105                 110

His Cys Tyr Lys Ser Gly Asp Val Cys Pro Leu Thr Gly Leu Ile Pro
            115                 120                 125

Ser Gly Tyr Ile Arg Ile Ser Ala Met Thr Lys Gly Thr Thr Ser Leu
        130                 135                 140

Phe Tyr Asn Leu Thr Val Pro Val Thr Lys Tyr Pro Lys Phe Lys Ser
145                 150                 155                 160

Leu Gln Cys Val Asp Asn Phe Thr Ser Val Tyr Leu Asn Gly Asp Leu
                165                 170                 175

Val Phe Thr Ser Asn Glu Thr Lys Asp Val Ser Ala Ala Gly Val His
                180                 185                 190

Phe Lys Ala Gly Gly Pro Ile Thr Tyr Lys Val Met Glu Lys Val Asp
            195                 200                 205

Val Leu Ala Tyr Phe Val Asn Gly Thr Ala Gln Asp Val Ile Leu Cys
        210                 215                 220

Asp Asn Ser Pro Arg Gly Leu Leu Ala Cys Gln Tyr Asn Thr Gly Asn
225                 230                 235                 240

Phe Ser Asp Gly Phe Tyr Pro Phe Thr Asn Ile Ser Leu Val Lys Glu
                245                 250                 255

Lys Phe Ile Val Tyr Arg Glu Thr Ser Val Asn Thr Thr Leu Val Leu
                260                 265                 270

Thr Asn Phe Thr Phe Thr Asn Val Ser Asn Ala Leu Pro Asn Thr Gly
            275                 280                 285

Gly Val Asn Thr Ile Asn Ile Tyr Gln Thr Gln Thr Ala Gln Ser Gly
```

```
            290                 295                 300
Cys Tyr Asn Phe Asn Phe Ser Phe Leu Ser Ser Phe Val Tyr Lys Gln
305                 310                 315                 320

Ser Asp Phe Met Tyr Gly Ser Tyr His Pro Lys Cys Asp Phe Arg Pro
                325                 330                 335

Glu Thr Ile Asn Asn Gly Leu Trp Phe Asn Ser Leu Ser Val Ser Leu
                340                 345                 350

Ala Tyr Gly Pro Leu Gln Gly Gly Cys Lys Gln Ser Val Phe Ser Asn
                355                 360                 365

Arg Ala Thr Cys Cys Tyr Ala Tyr Ser Tyr Asn Gly Pro Arg Leu Cys
            370                 375                 380

Lys Gly Val Tyr Ile Gly Glu Leu Gln Gln Tyr Phe Glu Cys Gly Leu
385                 390                 395                 400

Leu Val Tyr Val Thr Lys Ser Asp Gly Ser Arg Ile Gln Thr Arg Asn
                405                 410                 415

Glu Pro Leu Val Leu Thr His His Asn Tyr Asn Asn Ile Thr Leu Asp
                420                 425                 430

Arg Cys Val Glu Tyr Asn Ile Tyr Gly Arg Ser Gly Gln Gly Phe Ile
            435                 440                 445

Thr Asn Val Thr Ala Ala Ala Asn Tyr Asn Tyr Leu Ala Asp Gly
            450                 455                 460

Gly Leu Ala Ile Leu Asp Thr Ser Gly Ala Ile Asp Ile Phe Val Val
465                 470                 475                 480

Gln Gly Glu Tyr Gly Pro Asn Tyr Tyr Lys Val Asn Pro Cys Glu Asp
                485                 490                 495

Val Asn Gln Gln Phe Val Val Ser Gly Gly Ile Val Gly Val Leu
                500                 505                 510

Thr Ser His Asn Glu Thr Gly Ser Gln Gln Leu Glu Asn Leu Phe Tyr
            515                 520                 525

Val Lys Leu Thr Asn Ser Thr Arg Arg Thr Arg Arg Ser Thr Ile Ala
530                 535                 540

Asn Val Thr Thr Cys Pro Tyr Val Ser Tyr Gly Arg Phe Cys Ile Lys
545                 550                 555                 560

Pro Asp Gly Leu Val Ser Glu Ile Val Pro Gln Glu Leu Asp Tyr Phe
                565                 570                 575

Val Ala Pro Leu Leu Asn Val Thr Glu His Val Leu Ile Pro Asn Ser
                580                 585                 590

Phe Asn Leu Thr Val Thr Asp Glu Tyr Ile Gln Thr Arg Met Glu Lys
                595                 600                 605

Val Gln Ile Asn Cys Leu Gln Tyr Val Cys Gly Asn Ser Ile Glu Cys
610                 615                 620

Arg Asn Leu Phe Gln Gln Tyr Gly Pro Val Cys Asp Asn Ile Leu Ser
625                 630                 635                 640

Ile Val Asn Ser Val Gly Gln Arg Glu Asp Met Glu Ser Leu Thr Phe
                645                 650                 655

Tyr Ser Ser Thr Lys Pro Lys Gly Tyr Asn Thr Pro Ile Phe Ser Asn
                660                 665                 670

Ile Ser Thr Gly Asp Phe Asn Ile Ser Leu Met Leu Thr Pro Pro Ser
                675                 680                 685

Ser Pro Ser Gly Arg Ser Phe Ile Glu Asp Leu Leu Phe Thr Ser Val
            690                 695                 700

Glu Thr Val Gly Leu Pro Thr Asp Ala Glu Tyr Lys Lys Cys Thr Ala
705                 710                 715                 720
```

-continued

Gly Pro Leu Gly Thr Leu Lys Asp Leu Ile Cys Ala Arg Glu Tyr Asn
            725                 730                 735

Gly Leu Leu Val Leu Pro Pro Ile Ile Thr Ala Asp Met Gln Thr Met
            740                 745                 750

Tyr Thr Ala Ser Leu Val Gly Ala Met Ala Phe Gly Gly Ile Thr Ser
            755                 760                 765

Ala Ala Ala Ile Pro Phe Ala Thr Gln Ile Gln Ala Arg Ile Asn His
770                 775                 780

Leu Gly Ile Thr Gln Ser Leu Leu Met Lys Asn Gln Glu Lys Ile Ala
785                 790                 795                 800

Ala Ser Phe Asn Lys Ala Ile Gly His Met Gln Glu Gly Phe Arg Ser
            805                 810                 815

Thr Ser Leu Ala Leu Gln Gln Ile Gln Asp Val Val Asn Lys Gln Ser
            820                 825                 830

Ala Ile Leu Thr Glu Thr Met Asn Ser Leu Asn Lys Asn Phe Gly Ala
            835                 840                 845

Ile Thr Ser Val Ile Gln Asp Ile Tyr Ala Gln Leu Asp Ala Ile Gln
            850                 855                 860

Ala Asp Ala Gln Val Asp Arg Leu Ile Thr Gly Arg Leu Ser Ser Leu
865                 870                 875                 880

Ser Val Leu Ala Ser Ala Lys Gln Ser Glu Tyr Ile Arg Val Ser Gln
            885                 890                 895

Gln Arg Glu Leu Ala Thr Gln Lys Ile Asn Glu Cys Val Lys Ser Gln
            900                 905                 910

Ser Asn Arg Tyr Gly Phe Cys Gly Ser Gly Arg His Val Leu Ser Ile
            915                 920                 925

Pro Gln Asn Ala Pro Asn Gly Ile Val Phe Ile His Phe Thr Tyr Thr
930                 935                 940

Pro Glu Ser Phe Val Asn Val Thr Ala Ile Val Gly Phe Cys Val Ser
945                 950                 955                 960

Pro Ala Asn Ala Ser Gln Tyr Ala Ile Val Pro Ala Asn Gly Arg Gly
            965                 970                 975

Ile Phe Ile Gln Val Asn Gly Thr Tyr Tyr Ile Thr Ala Arg Asp Met
            980                 985                 990

Tyr Met Pro Arg Asp Ile Thr Ala Gly Asp Ile Val Thr Leu Thr Ser
            995                 1000                1005

Cys Gln Ala Asn Tyr Val Asn Val Asn Lys Thr Val Ile Thr Thr
    1010                1015                1020

Phe Val Glu Asp Asp Asp Phe Asp Phe Asp Asp Glu Leu Ser Lys
    1025                1030                1035

Trp Trp Asn Glu Thr Lys His Glu Ile Pro Asp Phe Asp Glu Phe
    1040                1045                1050

Asn Tyr Thr Val Pro Ile Leu Asn Ile Ser Ser Glu Ile Asp Arg
    1055                1060                1065

Ile Gln Gly Val Ile Gln Gly Leu Asn Asp Ser Leu Ile Asn Leu
    1070                1075                1080

Glu Glu Leu Ser Ile Ile Lys Thr Tyr Ile Lys Trp Pro Trp Tyr
    1085                1090                1095

Val Trp Leu Ala Ile Gly Phe Ala Ile Ile Phe Ile Leu Ile
    1100                1105                1110

Leu Gly Trp Val Phe Phe Met Thr Gly Cys Cys Gly Cys Cys Cys
    1115                1120                1125

Gly Cys Phe Gly Ile Ile Pro Leu Met Ser Lys Cys Gly Lys Lys
1130                1135                1140

Ser Ser Tyr Tyr Thr Thr Phe Asp Asn Asp Val Val Thr
1145                1150                1155

<210> SEQ ID NO 14
<211> LENGTH: 1078
<212> TYPE: PRT
<213> ORGANISM: Avian infectious bronchitis virus

<400> SEQUENCE: 14

Ala Leu Phe Asp Asn Asn Gln Ala Val Tyr Tyr Gln Ser Ala Phe
1               5                   10                  15

Arg Pro Ser Ser Gly Trp His Lys His Gly Gly Ala Tyr Ala Val Ala
                20                  25                  30

Asn Val Ser Leu Glu Tyr Ala Asn Ala Gly Ser Ser His Cys Thr
            35                  40                  45

Ala Gly Ala Ile Tyr Trp Ser Lys Asn Phe Thr Ala Ser Ser Val Ala
        50                  55                  60

Met Thr Ala Pro Gly Thr Gly Met Ser Trp Ser Thr Ala Gln Phe Cys
65                  70                  75                  80

Thr Ala His Cys Asn Phe Ser Asp Phe Thr Val Phe Val Thr His Cys
                85                  90                  95

Tyr Lys Ser Gly Asp Val Cys Pro Leu Thr Gly Leu Ile Pro Ser Gly
                100                 105                 110

Tyr Ile Arg Ile Ser Ala Met Thr Lys Gly Thr Thr Ser Leu Phe Tyr
            115                 120                 125

Asn Leu Thr Val Pro Val Thr Lys Tyr Pro Lys Phe Lys Ser Leu Gln
130                 135                 140

Cys Val Asp Asn Phe Thr Ser Val Tyr Leu Asn Gly Asp Leu Val Phe
145                 150                 155                 160

Thr Ser Asn Glu Thr Lys Asp Val Ser Ala Ala Gly Val His Phe Lys
                165                 170                 175

Ala Gly Gly Pro Ile Thr Tyr Lys Val Met Glu Lys Val Asp Val Leu
            180                 185                 190

Ala Tyr Phe Val Asn Gly Thr Ala Gln Asp Val Ile Leu Cys Asp Asn
        195                 200                 205

Ser Pro Arg Gly Leu Leu Ala Cys Gln Tyr Asn Thr Gly Asn Phe Ser
210                 215                 220

Asp Gly Phe Tyr Pro Phe Thr Asn Ile Ser Leu Val Lys Glu Lys Phe
225                 230                 235                 240

Ile Val Tyr Arg Glu Thr Ser Val Asn Thr Thr Leu Val Leu Thr Asn
                245                 250                 255

Phe Thr Phe Thr Asn Val Ser Asn Ala Leu Pro Asn Thr Gly Gly Val
            260                 265                 270

Asn Thr Ile Asn Ile Tyr Gln Thr Gln Thr Ala Gln Ser Gly Cys Tyr
        275                 280                 285

Asn Phe Asn Phe Ser Phe Leu Ser Ser Phe Val Tyr Lys Gln Ser Asp
    290                 295                 300

Phe Met Tyr Gly Ser Tyr His Pro Lys Cys Asp Phe Arg Pro Glu Thr
305                 310                 315                 320

Ile Asn Asn Gly Leu Trp Phe Asn Ser Leu Ser Val Ser Leu Ala Tyr
                325                 330                 335

Gly Pro Leu Gln Gly Gly Cys Lys Gln Ser Val Phe Ser Asn Arg Ala
            340                 345                 350

```
Thr Cys Cys Tyr Ala Tyr Ser Tyr Asn Gly Pro Arg Leu Cys Lys Gly
        355                 360                 365

Val Tyr Ile Gly Glu Leu Gln Gln Tyr Phe Glu Cys Gly Leu Leu Val
    370                 375                 380

Tyr Val Thr Lys Ser Asp Gly Ser Arg Ile Gln Thr Arg Asn Glu Pro
385                 390                 395                 400

Leu Val Leu Thr His His Asn Tyr Asn Ile Thr Leu Asp Arg Cys
                405                 410                 415

Val Glu Tyr Asn Ile Tyr Gly Arg Ser Gly Gln Gly Phe Ile Thr Asn
            420                 425                 430

Val Thr Ala Ala Ala Asn Tyr Asn Tyr Leu Ala Asp Gly Gly Leu
            435                 440                 445

Ala Ile Leu Asp Thr Ser Gly Ala Ile Asp Ile Phe Val Val Gln Gly
        450                 455                 460

Glu Tyr Gly Pro Asn Tyr Tyr Lys Val Asn Pro Cys Glu Asp Val Asn
465                 470                 475                 480

Gln Gln Phe Val Val Ser Gly Gly Ile Val Gly Val Leu Thr Ser
                485                 490                 495

His Asn Glu Thr Gly Ser Gln Gln Leu Glu Asn Leu Phe Tyr Val Lys
            500                 505                 510

Leu Thr Asn Ser Thr Arg Arg Thr Arg Arg Ser Thr Ile Ala Asn Val
        515                 520                 525

Thr Thr Cys Pro Tyr Val Ser Tyr Gly Arg Phe Cys Ile Lys Pro Asp
        530                 535                 540

Gly Leu Val Ser Glu Ile Val Pro Gln Glu Leu Asp Tyr Phe Val Ala
545                 550                 555                 560

Pro Leu Leu Asn Val Thr Glu His Val Leu Ile Pro Asn Ser Phe Asn
                565                 570                 575

Leu Thr Val Thr Asp Glu Tyr Ile Gln Thr Arg Met Glu Lys Val Gln
            580                 585                 590

Ile Asn Cys Leu Gln Tyr Val Cys Gly Asn Ser Ile Glu Cys Arg Asn
        595                 600                 605

Leu Phe Gln Gln Tyr Gly Pro Val Cys Asp Asn Ile Leu Ser Ile Val
    610                 615                 620

Asn Ser Val Gly Gln Arg Glu Asp Met Glu Ser Leu Thr Phe Tyr Ser
625                 630                 635                 640

Ser Thr Lys Pro Lys Gly Tyr Asn Thr Pro Ile Phe Ser Asn Ile Ser
                645                 650                 655

Thr Gly Asp Phe Asn Ile Ser Leu Met Leu Thr Pro Pro Ser Ser Pro
            660                 665                 670

Ser Gly Arg Ser Phe Ile Glu Asp Leu Leu Phe Thr Ser Val Glu Thr
        675                 680                 685

Val Gly Leu Pro Thr Asp Ala Glu Tyr Lys Lys Cys Thr Ala Gly Pro
    690                 695                 700

Leu Gly Thr Leu Lys Asp Leu Ile Cys Ala Arg Glu Tyr Asn Gly Leu
705                 710                 715                 720

Leu Val Leu Pro Pro Ile Ile Thr Ala Asp Met Gln Thr Met Tyr Thr
                725                 730                 735

Ala Ser Leu Val Gly Ala Met Ala Phe Gly Gly Ile Thr Ser Ala Ala
            740                 745                 750

Ala Ile Pro Phe Ala Thr Gln Ile Gln Ala Arg Ile Asn His Leu Gly
        755                 760                 765
```

```
Ile Thr Gln Ser Leu Leu Met Lys Asn Gln Glu Lys Ile Ala Ala Ser
    770                 775                 780

Phe Asn Lys Ala Ile Gly His Met Gln Glu Gly Phe Arg Ser Thr Ser
785                 790                 795                 800

Leu Ala Leu Gln Gln Ile Gln Asp Val Val Asn Lys Gln Ser Ala Ile
                805                 810                 815

Leu Thr Glu Thr Met Asn Ser Leu Asn Lys Asn Phe Gly Ala Ile Thr
                820                 825                 830

Ser Val Ile Gln Asp Ile Tyr Ala Gln Leu Asp Ala Ile Gln Ala Asp
            835                 840                 845

Ala Gln Val Asp Arg Leu Ile Thr Gly Arg Leu Ser Ser Leu Ser Val
850                 855                 860

Leu Ala Ser Ala Lys Gln Ser Glu Tyr Ile Arg Val Ser Gln Gln Arg
865                 870                 875                 880

Glu Leu Ala Thr Gln Lys Ile Asn Glu Cys Val Lys Ser Gln Ser Asn
                885                 890                 895

Arg Tyr Gly Phe Cys Gly Ser Gly Arg His Val Leu Ser Ile Pro Gln
            900                 905                 910

Asn Ala Pro Asn Gly Ile Val Phe Ile His Phe Thr Tyr Thr Pro Glu
            915                 920                 925

Ser Phe Val Asn Val Thr Ala Ile Val Gly Phe Cys Val Ser Pro Ala
930                 935                 940

Asn Ala Ser Gln Tyr Ala Ile Val Pro Ala Asn Gly Arg Gly Ile Phe
945                 950                 955                 960

Ile Gln Val Asn Gly Thr Tyr Tyr Ile Thr Ala Arg Asp Met Tyr Met
                965                 970                 975

Pro Arg Asp Ile Thr Ala Gly Asp Ile Val Thr Leu Thr Ser Cys Gln
            980                 985                 990

Ala Asn Tyr Val Asn Val Asn Lys Thr Val Ile Thr Thr Phe Val Glu
            995                 1000                1005

Asp Asp Asp Phe Asp Phe Asp Asp Glu Leu Ser Lys Trp Trp Asn
    1010                1015                1020

Glu Thr Lys His Glu Ile Pro Asp Phe Asp Glu Phe Asn Tyr Thr
    1025                1030                1035

Val Pro Ile Leu Asn Ile Ser Ser Glu Ile Asp Arg Ile Gln Gly
    1040                1045                1050

Val Ile Gln Gly Leu Asn Asp Ser Leu Ile Asn Leu Glu Glu Leu
    1055                1060                1065

Ser Ile Ile Lys Thr Tyr Ile Lys Trp Pro
    1070                1075

<210> SEQ ID NO 15
<211> LENGTH: 1169
<212> TYPE: PRT
<213> ORGANISM: Avian infectious bronchitis virus

<400> SEQUENCE: 15

Met Leu Val Gln Pro Leu Leu Leu Val Thr Leu Leu Cys Ala Leu Cys
1               5                   10                  15

Ser Ala Ser Leu Tyr Asn Asn Asp Ser Tyr Val Tyr Tyr Tyr Gln Ser
            20                  25                  30

Ala Phe Arg Pro Phe Asn Gly Trp His Leu His Gly Gly Ala Tyr Ala
        35                  40                  45

Val Val Asn Val Ser Gln Glu Thr Ala Asn Ala Gly Ser Ser Pro Ser
    50                  55                  60
```

```
Cys Thr Ala Gly Ala Ile Tyr Trp Ser Lys Asn Phe Thr Ala Ser Ser
 65                  70                  75                  80

Val Ala Met Thr Ala Pro Leu Gln Gly Met Gln Trp Ser Thr Ile Gln
                 85                  90                  95

Phe Cys Thr Ala His Cys Asn Phe Thr Asn Ile Val Val Phe Val Thr
                100                 105                 110

His Cys Tyr Lys Ser Gly Ser Thr Val Cys Pro Leu Thr Gly Leu Ile
                115                 120                 125

Pro Gln Asn His Ile Arg Ile Ser Ala Met Lys Gln Gly Asn Asn Gly
            130                 135                 140

Pro Ser Gly Leu Phe Tyr Asn Leu Thr Val Pro Val Thr Lys Tyr Ser
145                 150                 155                 160

Lys Phe Lys Ser Leu Gln Cys Val Asn Asn Gln Thr Ser Val Tyr Leu
                165                 170                 175

Asn Gly Asp Leu Val Phe Thr Ser Asn Glu Thr Lys Asp Val Ser Gly
            180                 185                 190

Ala Gly Val Tyr Phe Lys Ala Gly Gly Pro Ile Thr Tyr Lys Val Met
            195                 200                 205

Arg Glu Val Lys Ala Leu Ala Tyr Phe Val Asn Gly Thr Ala His Asp
210                 215                 220

Val Ile Leu Cys Asp Gly Ser Pro Arg Gly Leu Leu Ala Cys Gln Tyr
225                 230                 235                 240

Asn Thr Gly Lys Phe Ser Asp Gly Phe Tyr Pro Phe Thr Asn Asp Thr
                245                 250                 255

Leu Val Lys Glu Lys Phe Ile Val Tyr Arg Glu Asn Ser Val Asn Thr
                260                 265                 270

Thr Leu Thr Leu Thr Asn Phe Thr Phe Tyr Asn Glu Ser Asn Ala Leu
            275                 280                 285

Pro Asn Asn Gly Gly Val Asp Thr Ile Gln Leu Tyr Gln Thr His Thr
290                 295                 300

Ala Gln Ser Gly Tyr Tyr Asn Phe Asn Phe Ser Phe Leu Ser Ser Phe
305                 310                 315                 320

Gln Tyr Val Glu Ser Asn Phe Met Tyr Gly Ser Tyr His Pro Lys Cys
                325                 330                 335

Gly Phe Arg Pro Glu Ser Ile Asn Asn Gly Leu Trp Phe Asn Ser Leu
                340                 345                 350

Ser Val Ser Leu Ala Tyr Gly Pro Leu Gln Gly Gly Cys Lys Gln Ser
            355                 360                 365

Val Phe His Gly Arg Ala Thr Cys Cys Tyr Ala Tyr Ser Tyr Asn Gly
            370                 375                 380

Pro Thr Leu Cys Lys Gly Val Tyr Ser Gly Glu Leu Thr Arg Ser Tyr
385                 390                 395                 400

Gln Cys Gly Leu Leu Val Phe Val Thr Lys Ser Asp Gly Ser Arg Ile
                405                 410                 415

Gln Thr Ser Thr Lys Pro Ile Val Leu Thr Gln His Asn Tyr Asn Asn
            420                 425                 430

Ile Thr Leu Asp Arg Cys Val Glu Tyr Asn Ile Tyr Gly Arg Val Gly
            435                 440                 445

Gln Gly Phe Ile Thr Asn Val Thr Glu Ser Ala Ala Ala Phe Asn Tyr
            450                 455                 460

Leu Glu Asp Gly Gly Leu Ala Ile Leu Asp Thr Ser Gly Ala Ile Asp
465                 470                 475                 480
```

```
Ile Phe Val Val Gln Gly Glu Tyr Gly Phe Asn Tyr Lys Val Asn
                485                 490                 495

Pro Cys Glu Asp Val Asn Gln Gln Phe Val Val Ser Gly Gly Asn Leu
        500                 505                 510

Val Gly Ile Leu Thr Ser Ile Asn Gln Thr Gly Ser Gln Ser Ile Glu
            515                 520                 525

Asn Gln Phe Tyr Val Lys Leu Thr Asn Gly Ser Arg Arg Ser Arg Arg
    530                 535                 540

Ser Val Ser Glu Asn Val Thr Ser Cys Pro Tyr Val Ser Tyr Gly Lys
545                 550                 555                 560

Phe Cys Ile Lys Pro Asp Gly Ser Leu Ser Thr Ile Val Pro Lys Glu
                565                 570                 575

Leu Glu Gln Phe Val Ala Pro Leu Leu Asn Val Thr Glu His Val Leu
            580                 585                 590

Ile Pro Asp Ser Phe Asn Leu Thr Val Thr Asp Glu Tyr Ile Gln Thr
        595                 600                 605

Arg Met Asp Lys Val Gln Ile Asn Cys Leu Gln Tyr Val Cys Gly Asn
    610                 615                 620

Ser Phe Glu Cys Arg Lys Leu Phe Gln Gln Tyr Gly Pro Val Cys Asp
625                 630                 635                 640

Asn Ile Leu Ser Val Val Asn Ser Val Gly Gln Lys Glu Asp Met Glu
                645                 650                 655

Leu Leu Ser Phe Tyr Ser Ser Thr Lys Pro Ser Gly Ile Ser Gln Pro
            660                 665                 670

Leu Phe Asn Asn Phe Ser Thr Gly Asp Phe Asn Ile Ser Leu Leu Leu
        675                 680                 685

Thr Ser Pro Ser Ser Pro Ser Gly Arg Ser Phe Ile Glu Asp Leu Leu
    690                 695                 700

Phe Thr Ser Val Glu Ser Val Gly Leu Pro Thr Asp Glu Ala Tyr Lys
705                 710                 715                 720

Lys Cys Thr Ser Gly Pro Leu Gly Phe Val Lys Asp Leu Val Cys Ala
                725                 730                 735

Arg Glu Tyr Asn Gly Leu Leu Val Leu Pro Pro Ile Ile Thr Ala Glu
            740                 745                 750

Met Gln Thr Met Tyr Thr Ser Ser Leu Val Ala Ser Met Ala Leu Gly
        755                 760                 765

Gly Ile Thr Ala Ala Gly Ala Ile Pro Phe Ala Thr Gln Leu Gln Ala
    770                 775                 780

Arg Ile Asn His Leu Gly Ile Thr Gln Ser Leu Leu Met Lys Asn Gln
785                 790                 795                 800

Glu Lys Ile Ala Ala Ser Phe Asn Arg Ala Ile Gly His Met Gln Glu
                805                 810                 815

Gly Phe Lys Ser Thr Ser Leu Ala Leu Gln Gln Ile Gln Asp Val Val
            820                 825                 830

Asn Lys Gln Ser Ala Ile Leu Thr Glu Thr Met Ala Ser Leu Asn Lys
        835                 840                 845

Asn Phe Gly Ala Ile Ser Ser Val Leu Gln Asp Ile Tyr Gln Gln Leu
    850                 855                 860

Asp Val Ile Gln Ala Asp Ala Gln Val Asp Arg Ile Ile Thr Gly Arg
865                 870                 875                 880

Leu Ser Ser Leu Ser Val Leu Ala Ser Ala Lys Gln Ser Glu Tyr Ile
                885                 890                 895

Ala Val Ser Gln Gln Arg Ala Leu Ala Thr Gln Lys Ile Asn Glu Cys
```

```
                        900                 905                 910
Val Lys Ser Gln Ser Thr Arg Tyr Ser Phe Cys Gly Asn Gly Arg His
            915                 920                 925

Val Leu Thr Ile Pro Gln Asn Ala Pro Asn Gly Ile Val Phe Ile His
        930                 935                 940

Phe Thr Tyr Thr Pro Glu Ser Phe Val Asn Val Thr Ala Ile Val Gly
945                 950                 955                 960

Phe Cys Val Lys Pro Pro Asn Ala Ser His Tyr Ala Ile Val Pro Val
                965                 970                 975

Asn Gly Arg Gly Ile Phe Ile Gln Val Asn Gly Thr Tyr Tyr Ile Thr
            980                 985                 990

Ser Arg Asp Met Tyr Met Pro Arg Asn Ile Thr Ala Gly Asp Ile Val
        995                 1000                1005

Thr Leu Thr Ser Cys Gln Ala Asn Tyr Val Ser Val Asn Lys Thr
    1010                1015                1020

Val Ile Ser Thr Phe Val Glu Asp Asp Phe Asp Phe Asp Asp
    1025                1030                1035

Glu Leu Ser Lys Trp Trp Asn Asp Thr Lys His Glu Leu Pro Asp
    1040                1045                1050

Phe Asp Glu Phe Asn Tyr Thr Ile Pro Val Leu Asn Ile Ser Asn
    1055                1060                1065

Glu Ile Asp Arg Ile Gln Gly Val Ile Gln Gly Leu Asn Asp Ser
    1070                1075                1080

Leu Ile Asp Leu Glu Thr Leu Ser Ile Leu Lys Thr Tyr Ile Lys
    1085                1090                1095

Trp Pro Trp Tyr Val Trp Leu Ala Ile Phe Phe Ala Ile Val Ile
    1100                1105                1110

Phe Ile Leu Ile Ile Gly Trp Val Phe Phe Met Thr Gly Cys Cys
    1115                1120                1125

Gly Cys Cys Cys Gly Cys Phe Gly Ile Ile Pro Leu Met Asn Lys
    1130                1135                1140

Cys Gly Lys Lys Ser Ser Tyr Tyr Thr Thr Phe Asp Asn Asp Val
    1145                1150                1155

Val Thr Glu Gln Tyr Arg Pro Lys Lys Ser Val
    1160                1165

<210> SEQ ID NO 16
<211> LENGTH: 1082
<212> TYPE: PRT
<213> ORGANISM: Avian infectious bronchitis virus

<400> SEQUENCE: 16

Ser Leu Tyr Asn Asn Asp Ser Tyr Val Tyr Tyr Gln Ser Ala Phe
1               5                   10                  15

Arg Pro Phe Asn Gly Trp His Leu His Gly Gly Ala Tyr Ala Val Val
            20                  25                  30

Asn Val Ser Gln Glu Thr Ala Asn Ala Gly Ser Ser Pro Ser Cys Thr
        35                  40                  45

Ala Gly Ala Ile Tyr Trp Ser Lys Asn Phe Thr Ala Ser Ser Val Ala
    50                  55                  60

Met Thr Ala Pro Leu Gln Gly Met Gln Trp Ser Thr Ile Gln Phe Cys
65                  70                  75                  80

Thr Ala His Cys Asn Phe Thr Asn Ile Val Val Phe Val Thr His Cys
                85                  90                  95
```

-continued

```
Tyr Lys Ser Gly Ser Thr Val Cys Pro Leu Thr Gly Leu Ile Pro Gln
                100                 105                 110

Asn His Ile Arg Ile Ser Ala Met Lys Gln Gly Asn Asn Gly Pro Ser
            115                 120                 125

Gly Leu Phe Tyr Asn Leu Thr Val Pro Val Thr Lys Tyr Ser Lys Phe
        130                 135                 140

Lys Ser Leu Gln Cys Val Asn Asn Gln Thr Ser Val Tyr Leu Asn Gly
145                 150                 155                 160

Asp Leu Val Phe Thr Ser Asn Glu Thr Lys Asp Val Ser Gly Ala Gly
                165                 170                 175

Val Tyr Phe Lys Ala Gly Gly Pro Ile Thr Tyr Lys Val Met Arg Glu
            180                 185                 190

Val Lys Ala Leu Ala Tyr Phe Val Asn Gly Thr Ala His Asp Val Ile
        195                 200                 205

Leu Cys Asp Gly Ser Pro Arg Gly Leu Leu Ala Cys Gln Tyr Asn Thr
210                 215                 220

Gly Lys Phe Ser Asp Gly Phe Tyr Pro Phe Thr Asn Asp Thr Leu Val
225                 230                 235                 240

Lys Glu Lys Phe Ile Val Tyr Arg Glu Asn Ser Val Asn Thr Thr Leu
                245                 250                 255

Thr Leu Thr Asn Phe Thr Phe Tyr Asn Glu Ser Asn Ala Leu Pro Asn
            260                 265                 270

Asn Gly Gly Val Asp Thr Ile Gln Leu Tyr Gln Thr His Thr Ala Gln
        275                 280                 285

Ser Gly Tyr Tyr Asn Phe Asn Phe Ser Phe Leu Ser Ser Phe Gln Tyr
290                 295                 300

Val Glu Ser Asn Phe Met Tyr Gly Ser Tyr His Pro Lys Cys Gly Phe
305                 310                 315                 320

Arg Pro Glu Ser Ile Asn Asn Gly Leu Trp Phe Asn Ser Leu Ser Val
                325                 330                 335

Ser Leu Ala Tyr Gly Pro Leu Gln Gly Gly Cys Lys Gln Ser Val Phe
            340                 345                 350

His Gly Arg Ala Thr Cys Cys Tyr Ala Tyr Ser Tyr Asn Gly Pro Thr
        355                 360                 365

Leu Cys Lys Gly Val Tyr Ser Gly Glu Leu Thr Arg Ser Tyr Gln Cys
370                 375                 380

Gly Leu Leu Val Phe Val Thr Lys Ser Asp Gly Ser Arg Ile Gln Thr
385                 390                 395                 400

Ser Thr Lys Pro Ile Val Leu Thr Gln His Asn Tyr Asn Asn Ile Thr
                405                 410                 415

Leu Asp Arg Cys Val Glu Tyr Asn Ile Tyr Gly Arg Val Gly Gln Gly
            420                 425                 430

Phe Ile Thr Asn Val Thr Glu Ser Ala Ala Ala Phe Asn Tyr Leu Glu
        435                 440                 445

Asp Gly Gly Leu Ala Ile Leu Asp Thr Ser Gly Ala Ile Asp Ile Phe
450                 455                 460

Val Val Gln Gly Glu Tyr Gly Phe Asn Tyr Tyr Lys Val Asn Pro Cys
465                 470                 475                 480

Glu Asp Val Asn Gln Gln Phe Val Val Ser Gly Gly Asn Leu Val Gly
                485                 490                 495

Ile Leu Thr Ser Ile Asn Gln Thr Gly Ser Gln Ser Ile Glu Asn Gln
            500                 505                 510

Phe Tyr Val Lys Leu Thr Asn Gly Ser Arg Arg Ser Arg Arg Ser Val
```

-continued

```
            515                 520                 525
Ser Glu Asn Val Thr Ser Cys Pro Tyr Val Ser Tyr Gly Lys Phe Cys
            530                 535                 540
Ile Lys Pro Asp Gly Ser Leu Ser Thr Ile Val Pro Lys Glu Leu Glu
545                 550                 555                 560
Gln Phe Val Ala Pro Leu Leu Asn Val Thr Glu His Val Leu Ile Pro
                    565                 570                 575
Asp Ser Phe Asn Leu Thr Val Thr Asp Glu Tyr Ile Gln Thr Arg Met
                580                 585                 590
Asp Lys Val Gln Ile Asn Cys Leu Gln Tyr Val Cys Gly Asn Ser Phe
            595                 600                 605
Glu Cys Arg Lys Leu Phe Gln Gln Tyr Gly Pro Val Cys Asp Asn Ile
        610                 615                 620
Leu Ser Val Val Asn Ser Val Gly Gln Lys Glu Asp Met Glu Leu Leu
625                 630                 635                 640
Ser Phe Tyr Ser Ser Thr Lys Pro Ser Gly Ile Ser Gln Pro Leu Phe
                    645                 650                 655
Asn Asn Phe Ser Thr Gly Asp Phe Asn Ile Ser Leu Leu Leu Thr Ser
                660                 665                 670
Pro Ser Ser Pro Ser Gly Arg Ser Phe Ile Glu Asp Leu Leu Phe Thr
            675                 680                 685
Ser Val Glu Ser Val Gly Leu Pro Thr Asp Glu Ala Tyr Lys Lys Cys
        690                 695                 700
Thr Ser Gly Pro Leu Gly Phe Val Lys Asp Leu Val Cys Ala Arg Glu
705                 710                 715                 720
Tyr Asn Gly Leu Leu Val Leu Pro Pro Ile Ile Thr Ala Glu Met Gln
                    725                 730                 735
Thr Met Tyr Thr Ser Ser Leu Val Ala Ser Met Ala Leu Gly Gly Ile
                740                 745                 750
Thr Ala Ala Gly Ala Ile Pro Phe Ala Thr Gln Leu Gln Ala Arg Ile
            755                 760                 765
Asn His Leu Gly Ile Thr Gln Ser Leu Leu Met Lys Asn Gln Glu Lys
        770                 775                 780
Ile Ala Ala Ser Phe Asn Arg Ala Ile Gly His Met Gln Glu Gly Phe
785                 790                 795                 800
Lys Ser Thr Ser Leu Ala Leu Gln Gln Ile Gln Asp Val Val Asn Lys
                    805                 810                 815
Gln Ser Ala Ile Leu Thr Glu Thr Met Ala Ser Leu Asn Lys Asn Phe
                820                 825                 830
Gly Ala Ile Ser Ser Val Leu Gln Asp Ile Tyr Gln Gln Leu Asp Val
            835                 840                 845
Ile Gln Ala Asp Ala Gln Val Asp Arg Ile Ile Thr Gly Arg Leu Ser
        850                 855                 860
Ser Leu Ser Val Leu Ala Ser Ala Lys Gln Ser Glu Tyr Ile Ala Val
865                 870                 875                 880
Ser Gln Gln Arg Ala Leu Ala Thr Gln Lys Ile Asn Glu Cys Val Lys
                    885                 890                 895
Ser Gln Ser Thr Arg Tyr Ser Phe Cys Gly Asn Gly Arg His Val Leu
                900                 905                 910
Thr Ile Pro Gln Asn Ala Pro Asn Gly Ile Val Phe Ile His Phe Thr
            915                 920                 925
Tyr Thr Pro Glu Ser Phe Val Asn Val Thr Ala Ile Val Gly Phe Cys
        930                 935                 940
```

```
Val Lys Pro Pro Asn Ala Ser His Tyr Ala Ile Val Pro Val Asn Gly
945                 950                 955                 960

Arg Gly Ile Phe Ile Gln Val Asn Gly Thr Tyr Tyr Ile Thr Ser Arg
            965                 970                 975

Asp Met Tyr Met Pro Arg Asn Ile Thr Ala Gly Asp Ile Val Thr Leu
        980                 985                 990

Thr Ser Cys Gln Ala Asn Tyr Val  Ser Val Asn Lys Thr  Val Ile Ser
            995                 1000                 1005

Thr Phe  Val Glu Asp Asp Asp  Phe Asp Phe Asp  Glu Leu Ser
    1010                 1015                 1020

Lys Trp  Trp Asn Asp Thr Lys  His Glu Leu Pro Asp  Phe Asp Glu
    1025                 1030                 1035

Phe Asn Tyr Thr Ile Pro Val  Leu Asn Ile Ser Asn  Glu Ile Asp
        1040                 1045                 1050

Arg Ile Gln Gly Val Ile Gln  Gly Leu Asn Asp Ser  Leu Ile Asp
        1055                 1060                 1065

Leu Glu  Thr Leu Ser Ile Leu  Lys Thr Tyr Ile Lys  Trp Pro
    1070                 1075                 1080

<210> SEQ ID NO 17
<211> LENGTH: 3495
<212> TYPE: DNA
<213> ORGANISM: Avian infectious bronchitis virus

<400> SEQUENCE: 17
atgttggaca aaccgctttt actagtgact ctttggtatg cactatgtag tgctttgctc     60
tatgataata atacttacgt ttactactac caaagtgcct ttaggcctgg tccaggttgg    120
cacctatatg ggggtgctta tgcagtagat agggttttta tgaaaccaa caatgcaggc    180 agtgcatctg attgcactgc tggtactttt tatgaaagcc ataatatttc tgcttcttct    240
gtagccatga cagtaccaca taatggtatg tcttggtcag cttcacaatt ttgtacagct    300
cattgtaact tctcagactt tacagtgttc gttacgcatt gttttaaaaa tcaactcggt    360
agttgtccct tgacaggtat gattcctcag aatcatattc gtatttctgc tatgagagat    420
ggagttttgt tttataactt aacagttagc gtatctaaat accctagatt taaatcgctt    480
caatgtgtta gcaattctac atctgtctat gtaaatggtg accttgtttt cacttctaat    540
gaaacttctt acgttacggg tgcaggcgtt tattttaaaa gtggtgggcc tgtaacttat    600
aaagttatga aagaagttaa agccctagcc tactttatta tggtaccgc acaagaggtt    660 attttatgtg ataactcacc tagaggtttg cttgcatgtc agtataacac tggtaatttt    720
tcagatggat tctacccttt tactaatcat tctttagtta aggatggagtt tattgtatat    780 cgagaaagta gcactaacac tactttaaag ttaactaatt tcagttttac taatgtaagt    840
aatgcttctc ctaattcagg tggcgttgat acttccaat tatatcaaac aagtactgct    900
caggatggtt attataattt taattattca tttctgagta gttttgtgta taaaccatct    960
gattttatgt atgggtcata ccacccacat tgtaagttta gaccagagaa tattaataat    1020
ggcttatggt ttaattcatt atctgtgtca cttacttacg gacccattca aggtggttgt    1080
aagcaatctg tttttagtaa tagagcaact tgttgctatg cttattctta tcaagggcct    1140
agtagatgta aagggtgttta tagaggggag ctaacgcaat actttgaatg tggacttcta    1200
gtttacgtaa ctaagagtga tggctctcgt atacaaacta gaagtgaacc actggtgtta    1260
actcaatata attataacaa cattacttta aataagtgtg ttgagtataa tatatatggt    1320
```

```
agggttggtc aaggtttat tactaatgta actgaagcaa ctgctaatta tagttatcta    1380
gcagatggtg gtttagctat tttagatacc tcaggagcca tagacatatt tgttgttcaa    1440
ggtgcatatg gtcttaatta ttataaggtt aatccctgtg aagatgttaa ccaacagttt    1500
gtagtgtctg gtggcaactt agttggcatt cttacatctc ataatgaaac aggttctgaa    1560
tctattgaga accagtttta catcaaactc actaacggaa cacgtcgctc tagacgttct    1620
gttactggga atgttacaaa ttgcccttat gttagttatg gcaagttttg tataaaacca    1680
gatggttctt tatctataat agtaccacaa gaattagaac agtttgtggc gcctttattc    1740
aatgttactg agcatgtgct catacctgat agttttaatt taactgtcac agatgagtac    1800
atacaaactc gtatggataa ggttcaaatt atttgccttc agtatgtttg tggtaattct    1860
attgaatgca gaaagttgtt tcagcagtat ggacctgttt tgataatat attgtctgtt    1920
gtaaatggtg taggtcaaag agaggatatg gaacttttaa gtttctattc ttctactaaa    1980
cctagtggtt acaatacacc aatttttaat aatgttagca ctggtgactt taatatttcg    2040
ctcctactaa caccacctaa tagtcctact gggcgctctt ttattgaaga tcttctcttt    2100
acaagtgtag aatctgttgg attaccaact gatgaagagt ataaaaagtg tacagcagga    2160
cctttaggtt ttgttaaaga ccttgtttgt gctagagagt ataatggttt gctcgttctg    2220
cctcctatta ttactgcgga aatgcaaacc atgtatacta gttctttagt agcctctatg    2280
gctttaggtg gcattactgc agctggtgct ataccttttg ctacacaact gcaggccaga    2340
attaaccatt tgggtattac taattctctt ttgttgaaaa accaagaaaa aattgctgct    2400
tcctttaata aggccatcgg tcatatgcag gaagggttta aaagtacttc tctagcatta    2460
caacagattc aagatgttgt taataaacag agttctattc ttacagagac tatgcaatca    2520
cttaataaaa attttggtgc tatttcctct gtaattcaag acatttacca gcaactagat    2580
gctattcagg cagatgctca ggttgatcgt cttattacag gtagactctc ttcactatct    2640
gttttagctt ctgctaaaca ggcagagtat catagagtgt cacaacagcg tgagttggcc    2700
actcagaaaa ttaatgagtg tgttaagtct cagtctaata ggtattcatt ttgtggtaat    2760
ggtagacatg ttctaaccat accacagaat gcacccaatg gcatagtgtt tatacacttt    2820
acatacactc cagagagttt tgttaatgtt acggcaatag tagggttttg cgtaaaccca    2880
gctaatgcta gtcattatgc aatagtgcct gttaatggca ggggtgtttt tatagaagtt    2940
aatggtagtt actatatcac tgctcgtgat atgtatatgc caagagatat tactgcagga    3000
gacatagtca ctttgacttc ttgtcaagca aactatgtta atgtaaataa aaccgtcatt    3060
aacactttg tggaagatga cgattttgat ttttatgatg aattgtcaaa atggtggaat    3120
gatactaagc atgagctacc agattttgat gaattcaatt ataccgttcc agttttaaat    3180
attagtaatg aaattgacag aattcaacag gttattcagg gattaaatga ttccctaata    3240
gaccttgaaa cactctcaat tctcaaaact tatattaaat ggcttggta tgtgtggctt    3300
gccattgcat tccttaccat tatttttatt ctggtacttt gttggatatt tttcatgacc    3360
ggttgttgcg gttgttgttg tggatgcttt ggtatcatac cgttaatgag taagtgtggt    3420
aagaaatctt cttactacac gactttgat aatgatgtgg taacttaaca atacagacct    3480
aaaaagtctg tttaa                                                     3495
```

<210> SEQ ID NO 18
<211> LENGTH: 3225
<212> TYPE: DNA

<213> ORGANISM: Avian infectious bronchitis virus

<400> SEQUENCE: 18

```
gctttgtatg actcgagttc ttacgtgtac tactaccaaa gtgccttcag accacctgat      60
ggttggcatt tacatggggg tgcgtatgcg gttgttaata tttctagtga atctaataat     120
gcaggctctt catctgggtg tactgttggt attattcatg gtggtcgtgt tgttaatgct     180
tcttctatag ctatgacggc accgtcatca ggtatggctt ggtctagcag tcagttttgt     240
actgcatact gtaactttc agatactaca gtgtttgtta cacattgtta taaacatggt      300
gggtgtccta taactggcat gcttcaacag cattctatac gtgtttctgc tatgaaaaat     360
ggccagcttt tctataattt aacagttagt gtagctaagt accctacttt taaatcattt     420
cagtgtgtta ataatttaac atccgtatat ttaaatggtg atcttgttta cacctctaat     480
gagaccacag atgttacatc tgcaggtgtt tattttaaag ctggtggacc tataacttat     540
aaagttatga gagaagttag agccctggct tattttgtta atggtactgc acaagatgtt     600
attttgtgtg atgggtcacc tagaggcttg ttagcatgcc agtataatac tggcaatttt     660
tcagatggct tttatccttt tactaatagt agtttagtta agcagaagtt tattgtctat     720
cgtgaaaata tgttaatac tacttttacg ttacacaatt tcactttca taatgagact       780
ggcgccaacc caaatcctag tggtgtccag aatattcaaa cttaccaaac acaaacagct     840
cagagtggtt attataattt taattttttcc tttctgagta gttttgttta aaggagtct     900
aattttatgt atggatctta tcacccaagt tgtaatttta gactagaaac tattaataat     960
ggtttgtggt taattcact ttcagttagt attgcttacg tcctcttca aggtggttgc     1020
aagcaatctg tctttagtgg tagagcaacc tgttgttatg cttactcata tggaggtcct     1080
ttgctgtgta aggtgttta ttcaggtgag ttagatcata atttttgaatg tggactgtta     1140
gtttatgtta ctaagagcgg tggctctcgt atacaaacag ccactgaacc gccagttata     1200
actcaacaca attataataa tattactttta aatacttgtg ttgattataa tatatatggc     1260
agaactggcc agggttttat tactaatgta accgactcag ctgttagtta aattatcta     1320
gcagacgcag gtttggctat tttagataca tctggttcca tagacatctt tgtcgtacaa     1380
agtgaatatg gtcttaatta ttataaggtt aacccttgcg aagatgtcaa ccagcagttt     1440
gtagtttctg gtggtaaatt agtaggtatt cttacttcac gtaatgagac tggttcccag     1500
cttcttgaga atcagtttta catcaaaatc actaatggaa cacgtcgttt tagacgttct     1560
attactgaaa gtgttgaaaa ttgccccttat gttagttatg gtaagttttg tataaaacct     1620
gatggcagta ttgccacaat agtaccaaaa cagttagaac agtttgtggc acctttactt     1680
aatgttactg aaaatgtgct cataccctaac agttttaatt taactgttac agatgagtac     1740
atacaaactc ggatggataa ggtccaaatt aattgcctgc agtatatttg tggcaattct     1800
ctggagtgca gaaatttgtt tcaacaatat ggtcctgttt cgacaacat attgtctgta     1860
gtaaatagtg ttggtcaaaa agaagatatg gaacttttga atttctattc ttctactaag     1920
ccggctggtt ttaatacacc agttcttagt aatgttagca ctggtgagtt taatattact     1980
ctttttttaa caacgcctag tagtcctaga aggcgttctt ttattgaaga ccttctattt     2040
acaagtgttg aatctgttgg attaccaaca gatgacgcat acaaaaattg cactgcaggt     2100
cctttaggct ttcgtgaaaga ccttgcatgt gctcgtgaat ataatggttt gcttgtgttg     2160
cctccattaa taacagcaga aatgcaaact tgtatacaa gctctctagt agcttctatg     2220
gcttttggtg gtattactgc agctggtgct ataccttttg ccacacaact gcaggctaga     2280
```

```
attaatcact tgggtattac ccagtcactt cttttgaaga atcaagaaaa aattgctgct   2340
tcctttaata aggccatcgg tcatatgcag gaaggtttta gaagtacatc tttagcatta   2400
caacaaattc aagatgttgt taataagcag agtgctattc ttactgagac tatggcatca   2460
cttaataaaa attttggtgc catttcttct gtgattcaag aaatctacca gcaacttgac   2520
gccatacaag caaatgctca agtggatcgt cttataactg gtagattgtc atcactttct   2580
gttttagcat ctgctaagca ggcggagtat attagagtgt cacaacagcg tgagttagct   2640
actcagaaga ttaatgagtg tgttaagtca cagtccatta ggtactcctt ttgtggtaat   2700
ggacgacatg ttttaaccat accgcaaaat gcacctaatg gtatagtgtt tatacacttt   2760
tcttacactc cagatagttt tgttaatgtt actgcaatag tgggtttttg tgtaaagcca   2820
gctaatgcta gtcagtatgc aatagtaccc gctaatggta ggggtatttt tatacaagtt   2880
aatggtagtt actacatcac tgcacgagat atgtatatgc caagagctat tactgcagga   2940
gatatagtta cgcttacttc ttgtcaagca aattatgtaa gtgtaaataa gaccgtcatt   3000
actacattcg tagacaatga tgattttgat tttaatgacg aattgtcaaa atggtggaat   3060
gatactaagc atgagctacc agactttgac aaattcaatt acacagtacc tatacttgac   3120
attgatagtg aaattgatcg tattcaaggc gttatacagg gtcttaatga ctctctaata   3180
gaccttgaaa aactttcaat actcaaaact tatattaagt ggcct                   3225
```

<210> SEQ ID NO 19
<211> LENGTH: 11398
<212> TYPE: DNA
<213> ORGANISM: Artificial Sequence
<220> FEATURE:
<223> OTHER INFORMATION: Plasmid sequence with IBV

<400> SEQUENCE: 19

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tcggccgccc gggtaatacg actcactata gggacttaag atagatatta    480
atatatatct attgcactag ccttgcgcta gatttcaaac ttaacaaaac ggacttaaat    540
acctacagct ggtccccata ggtgttccat tgcagtgcac tttagtgccc tggatggcac    600
ctggccacct gtcaggtttt tgttgttaaa atatcattgt tgctggtatc actgcttgtt    660
ttgccgtgtc tcactttata catccgttgc ttgggctacc tagtatccag cgtcctacgg    720
gcgccgtggt cggttcgagt gcgaaggacc tctggttcat ctagcggtag gcgggtgtgt    780
ggaagtagcg cttcagacgt actggttctg ttgcgtgaaa cgcggggtca cctcccccca    840
catacctcta agggcttttg agcctagcgt tgggctacgt tctcgcacaa ggtcggctat    900
acgacgtttg taggggggtag tgccaaacaa cccctgaggt gacaggttct ggtggtgttt    960
cgaaaacaac aatgtgtgtg ccgcataata tgcgcgttat gcattttgga gcaggtagtg   1020
ataaaggagt ggcgcctggt agtactgttc ttaaacagtg gctccccgaa ggaacactcc   1080
```

-continued

```
ttgtcgataa tgatattgta gattatgttt ctgacgcaca cgtttctgtg ctttcagatt    1140
gcaataaata taagacagag cacaagtttg atcttgtgat atctgatatg tatacagaca    1200
atgattcaaa aagaaagcat gaaggcgtga tagccaataa tggcaatgat gacgtcttca    1260
tatacctttc aagttttcta cgcaataatt tggctctggg aggcagtttt gctgtaaaat    1320
taacagagac aagttggcat gagagtttat atgacattgc acaggattgt gcatggtgga    1380
caatgttttg tacagcagtg aatgcatctt cttcagaagc attcctgatt ggtgttaatt    1440
acttgggtgc aagtgcaaag gttaaagtta gtggaaaaac actgcacgca aattatatat    1500
tttggaggaa ttgtaattat ttacaaacct ctgcttatag tatatttgat gttgctaagt    1560
ttgatttgag attgaaagca acgccagttg ttaatcttaa gactgaacaa aagacagact    1620
tagtctttaa tttgataaag tgtggtaagt tactggtaag agatgttggt aacacctctt    1680
ttactagtga ctcttttgtg tgcactatgt agtgctgctt tgtatgactc gagttcttac    1740
gtgtactact accaaagtgc cttcagacca cctgatggtt ggcatttaca tgggggtgcg    1800
tatgcggttg ttaatatttc tagtgaatct aataatgcag gctcttcatc tggtgtgtact    1860 gttggtatta ttcatggtgg tcgtgttgtt aatgcttctt ctatagctat gacggcaccg    1920
tcatcaggta tggcttggtc tagcagtcag ttttgtactg catactgtaa cttttcagat    1980
actacagtgt tgttacaca ttgttataaa catggtgggt gtcctataac tggcatgctt    2040
caacagcatt ctatacgtgt ttctgctatg aaaaatggcc agcttttcta aatttaaca    2100 gttagtgtag ctaagtaccc tacttttaaa tcatttcagt gtgttaataa tttaacatcc    2160
gtatatttaa atggtgatct tgtttacacc tctaatgaga ccacagatgt tacatctgca    2220
ggtgtttatt ttaaagctgg tggacctata acttataaag ttatgagaga agttagagcc    2280
ctggcttatt ttgttaatgg tactgcacaa atgttatttt tgtgtgatgg gtcacctaga    2340
ggcttgttag catgccagta taatactggc aattttttcag atggctttta tccttttact    2400
aatagtagtt tagttaagca gaagtttatt gtctatcgtg aaaatagtgt taatactact    2460
tttacgttac acaatttcac ttttcataat gagactggcg ccaacccaaa tcctagtggt    2520
gtccagaata ttcaaactta ccaaacacaa acagctcaga gtggttatta aattttaat    2580 ttttcctttc tgagtagttt tgtttataag gagtctaatt ttatgtatgg atcttatcac    2640
ccaagttgta attttagact agaaactatt aataatggtt tgtggtttaa ttcactttca    2700
gttagtattg cttacggtcc tcttcaaggt ggttgcaagc aatctgtctt tagtggtaga    2760
gcaacctgtt gttatgctta ctcatatgga ggtcctttgc tgtgtaaagg tgttttattca    2820 ggtgagttag atcataattt tgaatgtgga ctgttagttt atgttactaa gagcggtggc    2880
tctcgtatac aaacagccac tgaaccgcca gttataactc aacacaatta taataatatt    2940
actttaaata cttgtgttga ttataatata tatggcagaa ctggccaggg ttttattact    3000
aatgtaaccg actcagctgt tagttataat tatctagcag acgcaggttt ggctatttta    3060
gatacatctg gttccataga catctttgtc gtacaaagtg aatatggtct taattattat    3120
aaggttaacc cttgcgaaga tgtcaaccag cagtttgtag tttctggtgg taaattagta    3180
ggtattctta cttcacgtaa tgagactggt tcccagcttc ttgagaatca gttttacatc    3240
aaaatcacta atggaacacg tcgttttaga cgttctatta ctgaaagtgt tgaaaattgc    3300
ccttatgtta gttatggtaa gttttgtata aaacctgatg gcagtattgc cacaatagta    3360
ccaaaacagt tagaacagtt tgtggcacct ttacttaatg ttactgaaaa tgtgctcata    3420
cctaacagtt ttaatttaac tgttacagat gagtacatac aaactcggat ggataaggtc    3480
```

```
caaattaatt gcctgcagta tatttgtggc aattctctgg agtgcagaaa tttgtttcaa    3540
caatatggtc ctgtttgcga caacatattg tctgtagtaa atagtgttgg tcaaaaagaa    3600
gatatggaac ttttgaattt ctattcttct actaagccgg ctggttttaa tacaccagtt    3660
cttagtaatg ttagcactgg tgagtttaat attactcttt ttttaacaac gcctagtagt    3720
cctagaaggc gttcttttat tgaagacctt ctatttacaa gtgttgaatc tgttggatta    3780
ccaacagatg acgcatacaa aaattgcact gcaggtcctt taggctttct gaaagacctt    3840
gcatgtgctc gtgaatataa tggttttgctt gtgttgcctc ctattataac agcagaaatg    3900
caaactttgt atacaagctc tctagtagct tctatggctt ttggtggtat tactgcagct    3960
ggtgctatac cttttgccac acaactgcag gctagaatta atcacttggg tattacccag    4020
tcacttcttt tgaagaatca agaaaaaatt gctgcttcct ttaataaggc catcggtcat    4080
atgcaggaag gttttagaag tacatcttta gcattacaac aaattcaaga tgttgttaat    4140
aagcagagtg ctattcttac tgagactatg gcatcactta taaaaattt tggtgccatt    4200 tcttctgtga ttcaagaaat ctaccagcaa cttgacgcca tacaagcaaa tgctcaagtg    4260
gatcgtctta taactggtag attgtcatca cttctgttt tagcatctgc taagcaggcg    4320
gagtatatta gagtgtcaca acagcgtgag ttagctactc agaagattaa tgagtgtgtt    4380
aagtcacagt ccattaggta ctccttttgt ggtaatggac gacatgtttt aaccataccg    4440
caaaatgcac ctaatggtat agtgtttata cacttttctt acactccaga tagttttgtt    4500
aatgttactg caatagtggg ttttgtgta aagccagcta atgctagtca gtatgcaata    4560
gtacccgcta atggtagggg tattttttata caagttaatg gtagttacta catcactgca    4620
cgagatatgt atatgccaag agctattact gcaggagata tagttacgct tacttcttgt    4680
caagcaaatt atgtaagtgt aaataagacc gtcattacta cattcgtaga caatgatgat    4740 tttgattta atgacgaatt gtcaaaatgg tggaatgata ctaagcatga gctaccagac    4800
tttgacaaat tcaattacac agtacctata cttgacattg atagtgaaat tgatcgtatt    4860
caaggcgtta tacagggtct taatgactct ctaatagacc ttgaaaaact ttcaatactc    4920
aaaacttata ttaagtggcc ttggtatgtg tggctagcca tagcttttgc cactattatc    4980
ttcatcttaa tattaggatg gttttctcttc atgactgggt gttgtggttg ttgttgtgga    5040
tgctttggca ttatgcctct aatgagtaag tgtggtaaga atcttctta ttacgact    5100 tttgataacg atgtggtaac tgaacaatac agacctaaaa agtctgttta atgatccaaa    5160
gtcccactag tttcttaata gtattaattt tgctttggtg taaacttgta ctaagttgtt    5220
ttagagagtt tattattgcc cttcaacaac taacacaagt tttactccaa attatcgata    5280
gtaatttaca gtctagactg acccttggc acagtctaga ctaatgttaa acttagaagc    5340
aattattgaa accggtgatc aagtgattca aaaaatcagt ttcaatttac agcatatttc    5400
aagtgtatta aacacagaag tatttgaccc ctttgactat tgttattaca gaggaggtaa    5460 ttttttgggaa atagagtcag ctgaagattg ttcaggtgat gatgaattta ttgaataagt    5520
cgctagagga gaatggaagt tttctaacgg cactttacat atttgtagga ttttагcat    5580 tttatcttct aggtagagca cttcaagcat ttgtacaggc tgctgatgct tgttgtttat    5640
tttggtacac gtggttagta attccaggag ttaagggtac agcctttgta tacaagtata    5700
catatggtag aaaacttaac aattcggaat tagaagcagt tgttgttaac gagtttccta    5760
agaacggttg gaataataaa aatccagcaa attttcaaga tgtccaacga aacaaattgt    5820
```

-continued

```
actcttgact ttgaacagtc agttgagctt tttaaagagt ataatttatt tataactgca    5880
ttcttgttgt tcttaaccat aatacttcag tatggttatg caacgcgtag taagtttatt    5940
tatatactta aaatgatagt gttatggtgc ttttggcccc ttaacattgc agtaggtgta    6000
atttcatgta tacccacc aaacacagga ggtcttgtcg cagcgataat acttactgtg      6060
tttgcgtgtc tttcttttgt aggttattgg atccagagta ttagactctt taagcggtgt    6120
agatcttggt ggtcatttaa cccagaatct aacgccgtag gttcaatact cctaactaat    6180
ggtcaacaat gtaattttgc tatagagagt gtgccgatgg tgctttctcc tattataaag    6240
aatggtgttc tttattgtga gggtcagtgg cttgctaaat gtgaaccaga ccacttgcct    6300
aaagacatat ttgtatgcac accagataga cgtaatatct atcgtatggt gcagaaatac    6360
actggtgacc aaagcggaaa taagaaaagg tttgctacat ttgtctatgc aaagcagtca    6420
gtagacactg gcgagctaga aagtgtagca acaggtggaa gtagccttta cacataaatg    6480
tgtgtgtgta gagagtattt aaaattattc ttcaatagtg cctctatttt aagagcgcgg    6540
aagagtattt gttttgagga tattaatata atcctctttt gttttgtact ctctttacaa    6600
gagttattat ttaagcaaca gttttttcctt tcctttgttt ggaagaaagt tgttgttaat    6660
ggtgtagaat tccaagtaga aaatggaaaa gtccactacg aaggaaaccc cattttccaa    6720
aaaggttgtt gtaggttgtg gtcccattat aagaaggatt aaatggatta aaccacctac    6780
actacttact tgtaataagg gcgtttggac ttacaagcgc ttaacaaata cagacgatga    6840
aatggctgac tagttttgga agagcagtta tttcttgtta taaagcccta ctattaactc    6900
agttaagagt attagatagg ttaatttag atcacggacc aaagcgagtc ttaacgtgtg     6960
gtaggcgagt gcttttatct caattagatt tagtttatag gttggcatat acgcccaccc    7020
aatcgctggt atgaataata gtaaagataa tccttttcgc ggagcaatag caagaaaagc    7080
gcgaatttat ctgagagaag gattagagtg tgtttacttt cttaacaaag caggacaagc    7140
agagccttgt cccgcgtgta cctccctagt atttcagggg aaaacttgtg aggaacacac    7200
agataataat aatctttgt catggcgagc ggtaagacaa ctgggaagac agacgcccca    7260
gcgccagtca tcaaactagg agggccaaaa ccacctaaag ttggttcttc tggaaatgct    7320
agctggtttc aagcactaaa agccaagaag ttaaattcac ctcctcctaa gtttgaaggt    7380
agcggcgttc ctgataatga aaatcttaaa ttaagccagc aacatgggta ctggagacgt    7440
caagccaggt acaagccagg taaaggcgga agaaaatcag tcccagatgc ttggtacttc    7500
tattacactg gaacaggacc agccgctgac ctgaattggg gtgatagcca agatggtata    7560
gtgtgggttt ctgcaaaggg tgctgatact aaatctagat ctaaccaggg tacaagggat    7620
cctgataagt ttgaccaata cccgctacga ttctcagatg gaggacctga tggtaatttc    7680
cgttgggact tcattccaat aaatcgtggt aggagtggaa gatcaacagc ggcttcatca    7740
gcagcatcta gtagagcacc gtcgcgtgat ggctcgcgtg gacgtagaag cggagctgaa    7800
gatgatctta tagctcgtgc agcaaagatc attcaggatc agcagaagaa gggttctcgc    7860
attactaaag ctaaggccga tgaaatggct catcgccggt attgtaagcg tactatccca    7920
cctggttata ggttgatca agtatttggt ccccgtacta aggtaaagga gggaaatttt    7980
ggtgatgaca agatgaatga ggagggtatt aaggatgggc gcgttacagc aatgctcaac    8040
ctagtcccta gcagccatgc ttgtcttttt ggaagtagag tgacgcccaa acttcaacca    8100
gatgggctgc acttgagatt tgaatttact actgtggttt ctaggatga tccgcagttt    8160
gataattatg tgaaaatttg tgatcagtgt gtcgatggtg tagggactcg gccaaaagac    8220
```

```
gatgaaccga gaccaaagtc acgcccaaat tcaagacctg ctacaagaac aagttctcca    8280
gcgccaagac aacagcgtca aaagaaggag aagaagtcaa agaagcagga tgatgaagta    8340
gataaggcat tgacctcaga tgaggagagg aacaatgcac agctggaatt tgatgatgaa    8400
ccgaaagtga ttaactgggg ggattcagca cttggagaga atgagttgta aagctagatt    8460
tccaacttaa catcatggac gtgcgtatgc tgttttttccc tactatagac ttttttagcat   8520 attatttttt gctatttgta tggtttatta caggtgaaga ttgtatgtat ttgttgtaca    8580
ctcgtatgtt ctatattatg ttttctgtag ttgttattag tgttgttctt gttcttactc    8640
tactgttctc ttttctttat tttagagtat caataagaat caaggaagat aggcatgtag    8700
tttgattacc tacatgtcta tcgccaggga aatgtctaat ctgtctactt agtagcctgg    8760
aaacgaacgg tagacccctta gattttaatt tagtttaatt tttagtttag tttaagttag    8820
tttagagtag gtataaagaa gccagtgccg gggccacgcg gagtacgatc gagggtacag    8880
cactaggacg cccactaggg gaagagctaa atttttagttt aagttaagtt taattggcta    8940
agtatagtta aaatttatag gctagtatag agttagagca aaaaaaaaa aaaaaaaaa     9000 aaaaaaaaa aaaaaaaaa aaaaaaaaa aaaaaaaaa aaaaaaaaa aaaaaaaaa          9060 aaaaaaaaa aaaaaaaag tttaaactta attaagaatt cccttggctc gagttcgaaa      9120
tcggatgccg ggaccgacga gtgcagaggc gtgcaagcga gcttggcgta atcatggtca    9180
tagctgtttc ctgtgtgaaa ttgttatccg ctcacaattc cacacaacat acgagccgga    9240
agcataaagt gtaaagcctg gggtgcctaa tgagtgagct aactcacatt aattgcgttg    9300
cgctcactgc ccgctttcca gtcgggaaac ctgtcgtgcc agctgcatta atgaatcggc    9360
caacgcgcgg ggagaggcgg tttgcgtatt gggcgctctt ccgcttcctc gctcactgac    9420
tcgctgcgct cggtcgttcg gctgcggcga gcggtatcag ctcactcaaa ggcggtaata    9480
cggttatcca cagaatcagg ggataacgca ggaaagaaca tgtgagcaaa aggccagcaa    9540
aaggccagga accgtaaaaa ggccgcgttg ctggcgtttt tccataggct ccgcccccct    9600
gacgagcatc acaaaaatcg acgctcaagt cagaggtggc gaaacccgac aggactataa    9660
agataccagg cgtttccccc tggaagctcc ctcgtgcgct ctcctgttcc gaccctgccg    9720
cttaccggat acctgtccgc ctttctccct tcgggaagcg tggcgctttc tcatagctca    9780
cgctgtaggt atctcagttc ggtgtaggtc gttcgctcca agctgggctg tgtgcacgaa    9840
ccccccgttc agcccgaccg ctgcgcctta tccggtaact atcgtcttga gtccaacccg    9900
gtaagacacg acttatcgcc actggcagca gccactggta acaggattag cagagcgagg    9960
tatgtaggcg gtgctacaga gttcttgaag tggtggccta actacggcta cactagaaga   10020
acagtatttg gtatctgcgc tctgctgaag ccagttacct tcggaaaaag agttggtagc   10080
tcttgatccg gcaaacaaac caccgctggt agcggtggtt ttttgtttg caagcagcag    10140 attacgcgca gaaaaaagg atctcaagaa gatcctttga tcttttctac ggggtctgac    10200
gctcagtgga acgaaaactc acgttaaggg attttggtca tgagattatc aaaaaggatc   10260
ttcacctaga tccttttaaa ttaaaaatga agttttaaat caatctaaag tatatatgag   10320
taaacttggt ctgacagtta ccaatgctta atcagtgagg cacctatctc agcgatctgt   10380
ctatttcgtt catccatagt tgcctgactc cccgtcgtgt agataactac gatacgggag   10440
ggcttaccat ctggccccag tgctgcaatg ataccgcgag acccacgctc accggctcca   10500
gatttatcag caataaacca gccagccgga agggccgagc gcagaagtgg tcctgcaact   10560
```

| | |
|---|---|
| ttatccgcct ccatccagtc tattaattgt tgccgggaag ctagagtaag tagttcgcca | 10620 |
| gttaatagtt tgcgcaacgt tgttgccatt gctacaggca tcgtggtgtc acgctcgtcg | 10680 |
| tttggtatgg cttcattcag ctccggttcc caacgatcaa ggcgagttac atgatccccc | 10740 |
| atgttgtgca aaaaagcggt tagctccttc ggtcctccga tcgttgtcag aagtaagttg | 10800 |
| gccgcagtgt tatcactcat ggttatggca gcactgcata attctcttac tgtcatgcca | 10860 |
| tccgtaagat gcttttctgt gactggtgag tactcaacca agtcattctg agaatagtgt | 10920 |
| atgcggcgac cgagttgctc ttgcccggcg tcaatacggg ataataccgc gccacatagc | 10980 |
| agaactttaa aagtgctcat cattggaaaa cgttcttcgg ggcgaaaact ctcaaggatc | 11040 |
| ttaccgctgt tgagatccag ttcgatgtaa cccactcgtg cacccaactg atcttcagca | 11100 |
| tcttttactt tcaccagcgt ttctgggtga gcaaaaacag gaaggcaaaa tgccgcaaaa | 11160 |
| aagggaataa gggcgacacg gaaatgttga atactcatac tcttcctttt tcaatattat | 11220 |
| tgaagcattt atcagggtta ttgtctcatg agcggataca tatttgaatg tatttagaaa | 11280 |
| aataaacaaa taggggttcc gcgcacattt ccccgaaaag tgccacctga cgtctaagaa | 11340 |
| accattatta tcatgacatt aacctataaa aataggcgta tcacgaggcc ctttcgtc | 11398 |

<210> SEQ ID NO 20
<211> LENGTH: 3231
<212> TYPE: DNA
<213> ORGANISM: Avian infectious bronchitis virus

<400> SEQUENCE: 20

| | |
|---|---|
| ttgctctatg ataataatac ttacgtttac tactaccaaa gtgcctttag gcctggtcca | 60 |
| ggttggcacc tatatggggg tgcttatgca gtagataggg ttttttaatga aaccaacaat | 120 |
| gcaggcagtg catctgattg cactgctggt acttttttatg aaagccataa tatttctgct | 180 |
| tcttctgtag ccatgacagt accacataat ggtatgtctt ggtcagcttc acaattttgt | 240 |
| acagctcatt gtaacttctc agactttaca gtgttcgtta cgcattgttt taaaaatcaa | 300 |
| ctcggtagtt gtccttgac aggtatgatt cctcagaatc atattcgtat ttctgctatg | 360 |
| agagatggag ttttgttta aacttaaca gttagcgtat ctaaatacc tagatttaaa | 420 |
| tcgcttcaat gtgttagcaa ttctacatct gtctatgtaa atggtgaccct tgttttcact | 480 |
| tctaatgaaa cttcttacgt tacgggtgca ggcgtttatt ttaaaagtgg tgggcctgta | 540 |
| acttataaag ttatgaaaga agttaaagcc ctagcctact ttattaatgg taccgcacaa | 600 |
| gaggttattt tatgtgataa ctcacctaga ggtttgcttg catgtcagta taacactggt | 660 |
| aatttttcag atggattcta cccttttact aatcattctt tagttaagga taggtttatt | 720 |
| gtatatcgag aaagtagcac taacactact ttaaagttaa ctaatttcag ttttactaat | 780 |
| gtaagtaatg cttctcctaa ttcaggtggc gttgatactt tccaattata tcaaacaagt | 840 |
| actgctcagg atggttatta taattttaat ttatcatttc tgagtagttt tgtgtataaa | 900 |
| ccatctgatt ttatgtatgg gtcataccac ccacattgta agtttagacc agagaatatt | 960 |
| aataatggct tatggtttaa ttcattatct gtgtcactta cttacggacc cattcaaggt | 1020 |
| ggttgtaagc aatctgtttt tagtaataga gcaacttgtt gctatgctta ttcttatcaa | 1080 |
| gggcctagta gatgtaaggg tgtttataga ggggagctaa cgcaatactt tgaatgtgga | 1140 |
| cttctagttt acgtaactaa gagtgatggc tctcgtatac aaactagaag tgaaccactg | 1200 |
| gtgttaactc aatataatta taacaacatt actttaaata gtgtgttga gtataatata | 1260 |
| tatggtaggg ttggtcaagg ttttattact aatgtaactg aagcaactgc taattatagt | 1320 |

```
tatctagcag atggtggttt agctatttta gatacctcag gagccataga catatttgtt   1380
gttcaaggtg catatggtct taattattat aaggttaatc cctgtgaaga tgttaaccaa   1440
cagtttgtag tgtctggtgg caacttagtt ggcattctta catctcataa tgaaacaggt   1500
tctgaatcta ttgagaacca gttttacatc aaactcacta acggaacacg tcgctctaga   1560
cgttctgtta ctgggaatgt tacaaattgc ccttatgtta gttatggcaa gttttgtata   1620
aaaccagatg gttctttatc tataatagta ccacaagaat tagaacagtt tgtggcgcct   1680
ttattcaatg ttactgagca tgtgctcata cctgatagtt ttaatttaac tgtcacagat   1740
gagtacatac aaactcgtat ggataaggtt caaattattt gccttcagta tgtttgtggt   1800
aattctattg aatgcagaaa gttgtttcag cagtatggac ctgtttgtga taatatattg   1860
tctgttgtaa atggtgtagg tcaaagagag gatatggaac ttttaagttt ctattcttct   1920
actaaaccta gtggttacaa tacaccaatt tttaataatg ttagcactgg tgactttaat   1980
atttcgctcc tactaacacc acctaatagt cctactgggc gctcttttat tgaagatctt   2040
ctctttacaa gtgtagaatc tgttggatta ccaactgatg aagagtataa aaagtgtaca   2100
gcaggacctt taggttttgt taaagacctt gtttgtgcta gagagtataa tggtttgctc   2160
gttctgcctc ctattattac tgcggaaatg caaaccatgt atactagttc tttagtagcc   2220
tctatggctt taggtggcat tactgcagct ggtgctatac cttttgctac acaactgcag   2280
gccagaatta accatttggg tattactaat tctcttttgt tgaaaaacca agaaaaaatt   2340
gctgcttcct ttaataaggc catcggtcat atgcaggaag ggtttaaaag tacttctcta   2400
gcattacaac agattcaaga tgttgttaat aaacagagtt ctattcttac agagactatg   2460
caatcactta ataaaaattt tggtgctatt tcctctgtaa ttcaagacat ttaccagcaa   2520
ctagatgcta ttcaggcaga tgctcaggtt gatcgtctta ttacaggtag actctcttca   2580
ctatctgttt tagcttctgc taaacaggca gagtatcata gagtgtcaca acagcgtgag   2640
ttggccactc agaaaattaa tgagtgtgtt aagtctcagt ctaataggta ttcattttgt   2700
ggtaatggta gacatgttct aaccatacca cagaatgcac ccaatggcat agtgtttata   2760
cactttacat acactccaga gagttttgtt aatgttacgg caatagtagg gttttgcgta   2820
aacccagcta atgctagtca ttatgcaata gtgcctgtta atggcagggg tgtttttata   2880
gaagttaatg gtagttacta tatcactgct cgtgatatgt atatgccaag agatattact   2940
gcaggagaca tagtcacttt gacttcttgt caagcaaact atgttaatgt aaataaaacc   3000
gtcattaaca cttttgtgga agatgacgat tttgattttt atgatgaatt gtcaaaatgg   3060
tggaatgata ctaagcatga gctaccagat tttgatgaat tcaattatac cgttccagtt   3120
ttaaatatta gtaatgaaat tgacagaatt caacaggtta ttcagggatt aaatgattcc   3180
ctaatagacc ttgaaacact ctcaattctc aaaacttata ttaaatggcc t            3231
```

<210> SEQ ID NO 21
<211> LENGTH: 11404
<212> TYPE: DNA
<213> ORGANISM: Artificial Sequence
<220> FEATURE:
<223> OTHER INFORMATION: Plasmid with IBV

<400> SEQUENCE: 21

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
```

-continued

| | |
|---|---|
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt ggagatcggt acttcgcgaa | 420 |
| tgcgtcgaga tcgccgccc gggtaatacg actcactata gggacttaag atagatatta | 480 |
| atatatatct attgcactag ccttgcgcta gatttcaaac ttaacaaaac ggacttaaat | 540 |
| acctacagct ggtccccata ggtgttccat tgcagtgcac tttagtgccc tggatggcac | 600 |
| ctggccacct gtcaggtttt tgttgttaaa atatcattgt tgctggtatc actgcttgtt | 660 |
| ttgccgtgtc tcactttata catccgttgc ttgggctacc tagtatccag cgtcctacgg | 720 |
| gcgccgtggt cggttcgagt gcgaaggacc tctggttcat ctagcggtag gcgggtgtgt | 780 |
| ggaagtagcg cttcagacgt actggttctg ttgcgtgaaa cgcggggtca cctccccca | 840 |
| catacctcta agggcttttg agcctagcgt tgggctacgt tctcgcacaa ggtcggctat | 900 |
| acgacgtttg taggggtag tgccaaacaa cccctgaggt gacaggttct ggtggtgttt | 960 |
| cgaaaacaac aatgtgtgtg ccgcataata tgcgcgttat gcattttgga gcaggtagtg | 1020 |
| ataaaggagt ggcgcctggt agtactgttc ttaaacagtg gctccccgaa ggaacactcc | 1080 |
| ttgtcgataa tgatattgta gattatgttt ctgacgcaca cgtttctgtg ctttcagatt | 1140 |
| gcaataaata aagacagag cacaagtttg atcttgtgat atctgatatg tatacagaca | 1200 |
| atgattcaaa aagaaagcat gaaggcgtga tagccaataa tggcaatgat gacgtcttca | 1260 |
| tataccttc aagttttcta cgcaataatt tggctctggg aggcagtttt gctgtaaaat | 1320 |
| taacagagac aagttggcat gagagtttat atgacattgc acaggattgt gcatggtgga | 1380 |
| caatgttttg tacagcagtg aatgcatctt cttcagaagc attcctgatt ggtgttaatt | 1440 |
| acttgggtgc aagtgcaaag gttaaagtta gtggaaaaac actgcacgca aattatatat | 1500 |
| tttggaggaa ttgtaattat ttacaaacct ctgcttatag tatatttgat gttgctaagt | 1560 |
| ttgatttgag attgaaagca acgccagttg ttaatcttaa gactgaacaa aagacagact | 1620 |
| tagtctttaa tttgataaag tgtggtaagt tactggtaag agatgttggt aacacctctt | 1680 |
| ttactagtga ctcttttgtg tgcactatgt agtgctttgc tctatgataa taatacttac | 1740 |
| gtttactact accaaagtgc ctttaggcct ggtccaggtt ggcacctata tgggggtgct | 1800 |
| tatgcagtag atagggtttt taatgaaacc aacaatgcag gcagtgcatc tgattgcact | 1860 |
| gctggtactt tttatgaaag ccataatatt tctgcttctt ctgtagccat gacagtacca | 1920 |
| cataatggta tgtcttggtc agcttcacaa ttttgtacag ctcattgtaa cttctcagac | 1980 |
| tttacagtgt tcgttacgca ttgttttaaa aatcaactcg gtagttgtcc cttgacaggt | 2040 |
| atgattcctc agaatcatat tcgtatttct gctatgagag atggagtttt gttttataac | 2100 |
| ttaacagtta gcgtatctaa atacccctaga tttaaatcgc ttcaatgtgt tagcaattct | 2160 |
| acatctgtct atgtaaatgg tgaccttgtt ttcacttcta tgaaacttc ttacgttacg | 2220 |
| ggtgcaggcg tttattttaa aagtggtggg cctgtaactt ataaagttat gaagaagtt | 2280 |
| aaagccctag cctactttat taatggtacc gcacaagagg ttattttatg tgataactca | 2340 |
| cctagaggtt tgcttgcatg tcagtataac actggtaatt tttcagatgg attctaccct | 2400 |
| tttactaatc attctttagt taaggatagg tttattgtat atcgagaaag tagcactaac | 2460 |
| actactttaa agttaactaa tttcagtttt actaatgtaa gtaatgcttc tcctaattca | 2520 |

```
ggtggcgttg atactttcca attatatcaa acaagtactg ctcaggatgg ttattataat      2580
tttaatttat catttctgag tagttttgtg tataaaccat ctgattttat gtatgggtca      2640
taccacccac attgtaagtt tagaccagag aatattaata atggcttatg gtttaattca      2700
ttatctgtgt cacttactta cggacccatt caaggtggtt gtaagcaatc tgttttagt       2760 aatagagcaa cttgttgcta tgcttattct tatcaagggc ctagtagatg taagggtgtt      2820
tatagagggg agctaacgca atactttgaa tgtggacttc tagtttacgt aactaagagt      2880
gatggctctc gtatacaaac tagaagtgaa ccactggtgt taactcaata taattataac      2940
aacattactt taaataagtg tgttgagtat aatatatatg gtagggttgg tcaaggtttt      3000
attactaatg taactgaagc aactgctaat tatagttatc tagcagatgg tggtttagct      3060
attttagata cctcaggagc catagacata tttgttgttc aaggtgcata tggtcttaat      3120
tattataagg ttaatccctg tgaagatgtt aaccaacagt ttgtagtgtc tggtggcaac      3180
ttagttggca ttcttacatc tcataatgaa acaggttctg aatctattga gaaccagttt      3240
tacatcaaac tcactaacgg aacacgtcgc tctagacgtt ctgttactgg gaatgttaca      3300
aattgcccct tatgttagtta tggcaagttt tgtataaaac cagatggttc tttatctata      3360
atagtaccac aagaattaga acagtttgtg gcgcctttat tcaatgttac tgagcatgtg      3420
ctcatacctg atagttttaa tttaactgtc acagatgagt acatacaaac tcgtatggat      3480
aaggttcaaa ttatttgcct tcagtatgtt tgtggtaatt ctattgaatg cagaaagttg      3540
tttcagcagt atgaccctgt ttgtgataat atattgtctg ttgtaaatgg tgtaggtcaa      3600
agagaggata tggaactttt aagtttctat tcttctacta aacctagtgg ttacaataca      3660 ccaatttta ataatgttag cactggtgac tttaatattt cgctcctact aacaccacct      3720
aatagtccta ctgggcgctc ttttattgaa gatcttctct ttacaagtgt agaatctgtt      3780
ggattaccaa ctgatgaaga gtataaaaag tgtacagcag gaccttagg ttttgttaaa       3840 gaccttgttt gtgctagaga gtataatggt ttgctcgttc tgcctcctat tattactgcg      3900
gaaatgcaaa ccatgtatac tagttcttta gtagcctcta tggctttagg tggcattact      3960
gcagctggtg ctataccttt tgctacacaa ctgcaggcca gaattaacca tttgggtatt      4020
actaattctc ttttgttgaa aaaccaagaa aaaattgctg cttccttaa taaggccatc       4080 ggtcatatgc aggaagggtt taaaagtact tctctagcat acaacagat tcaagatgtt       4140 gttaataaac agagttctat tcttacagag actatgcaat cacttaataa aaattttggt      4200
gctatttcct ctgtaattca agacatttac cagcaactag atgctattca ggcagatgct      4260
caggttgatc gtcttattac aggtagactc tcttcactat ctgttttagc ttctgctaaa      4320
caggcagagt atcatagagt gtcacaacag cgtgagttgg ccactcagaa aattaatgag      4380
tgtgttaagt ctcagtctaa taggtattca ttttgtggta atggtagaca tgttctaacc      4440
ataccacaga atgcacccaa tggcatagtg tttatacact ttacatacac tccagagagt      4500
tttgttaatg ttacggcaat agtagggttt tgcgtaaacc cagctaatgc tagtcattat      4560
gcaatagtgc ctgttaatgg cagggtgtt tttatagaag ttaatggtag ttactatatc       4620
actgctcgtg atatgtatat gccaagagat attactgcag gagacatagt cactttgact      4680
tcttgtcaag caaactatgt taatgtaaat aaaaccgtca ttaacacttt tgtggaagat      4740
gacgattttg attttatga tgaattgtca aaatggtgga atgatactaa gcatgagcta       4800
ccagattttg atgaattcaa ttataccgtt ccagttttaa atattagtaa tgaaattgac      4860
```

```
agaattcaac aggttattca gggattaaat gattccctaa tagaccttga aacactctca   4920
attctcaaaa cttatattaa atggccttgg tatgtgtggc tagccatagc ttttgccact   4980
attatcttca tcttaatatt aggatgggtt ttcttcatga ctgggtgttg tggttgttgt   5040
tgtggatgct ttggcattat gcctctaatg agtaagtgtg gtaagaaatc ttcttattac   5100 acgactttg ataacgatgt ggtaactgaa caatacagac ctaaaaagtc tgtttaatga    5160
tccaaagtcc cactagtttc ttaatagtat taattttgct ttggtgtaaa cttgtactaa   5220
gttgttttag agagtttatt attgcccttc aacaactaac acaagtttta ctccaaatta   5280
tcgatagtaa tttacagtct agactgaccc tttggcacag tctagactaa tgttaaactt   5340
agaagcaatt attgaaaccg gtgatcaagt gattcaaaaa atcagtttca atttacagca   5400
tatttcaagt gtattaaaca cagaagtatt tgacccctt gactattgtt attacagagg    5460
aggtaatttt tgggaaatag agtcagctga agattgttca ggtgatgatg aatttattga   5520
ataagtcgct agaggagaat ggaagttttc taacggcact ttacatattt gtaggatttt   5580
tagcatttta tcttctaggt agagcacttc aagcatttgt acaggctgct gatgcttgtt   5640
gtttattttg gtacacgtgg ttagtaattc caggagttaa gggtacagcc tttgtataca   5700
agtatacata tggtagaaaa cttaacaatt cggaattaga agcagttgtt gttaacgagt   5760
ttcctaagaa cggttggaat aataaaaatc cagcaaattt tcaagatgtc caacgaaaca   5820
aattgtactc ttgactttga acagtcagtt gagcttttta aagagtataa tttatttata   5880
actgcattct tgttgttctt aaccataata cttcagtatg ttatgcaac gcgtagtaag    5940 tttatttata tacttaaaat gatagtgtta tggtgctttt ggccccttaa cattgcagta   6000
ggtgtaattt catgtatata cccaccaaac acaggaggtc ttgtcgcagc gataatactt   6060
actgtgtttg cgtgtctttc ttttgtaggt tattggatcc agagtattag actcttaag    6120 cggtgtagat cttggtggtc atttaaccca gaatctaacg ccgtaggttc aatactccta   6180
actaatggtc aacaatgtaa ttttgctata gagagtgtgc cgatggtgct ttctcctatt   6240
ataaagaatg gtgttcttta ttgtgagggt cagtggcttg ctaaatgtga accagaccac   6300
ttgcctaaag acatatttgt atgcacacca gatagacgta atatctatcg tatggtgcag   6360
aaatacactg gtgaccaaag cggaaataag aaaaggtttg ctacatttgt ctatgcaaag   6420
cagtcagtag acactggcga gctagaaagt gtagcaacag gtggaagtag cctttacaca   6480
taaatgtgtg tgtgtagaga gtatttaaaa ttattcttca atagtgcctc tatttaaga    6540 gcgcggaaga gtatttgttt tgaggatatt aatataaatc ctctttgttt tgtactctct   6600
ttacaagagt tattatttaa gcaacagttt ttccttcct ttgtttggaa gaaagttgtt    6660
gttaatggtg tagaattcca agtagaaaat ggaaagtcc actacgaagg aaaccccatt    6720
ttccaaaaag gttgttgtag gttgtggtcc cattataaga aggattaaat ggattaaacc   6780
acctacacta cttacttgta ataagggcgt ttggacttac aagcgcttaa caaatacaga   6840
cgatgaaatg gctgactagt tttggaagag cagttatttc ttgttataaa gccctactat   6900
taactcagtt aagagtatta gataggttaa ttttagatca cggaccaaag cgagtcttaa   6960
cgtgtggtag gcgagtgctt ttatctcaat tagatttagt ttataggttg gcatatacgc   7020
ccacccaatc gctggtatga ataatagtaa agataatcct tttcgcggag caatagcaag   7080
aaaagcgcga atttatctga gagaaggatt agagtgtgtt tactttctta acaaagcagg   7140
acaagcagag ccttgtcccg cgtgtacctc cctagtattt cagggaaaaa cttgtgagga   7200
acacacagat aataataatc ttttgtcatg gcgagcggta agacaactgg gaagacagac   7260
```

```
gccccagcgc cagtcatcaa actaggaggg ccaaaaccac ctaaagttgg ttcttctgga    7320
aatgctagct ggtttcaagc actaaaagcc aagaagttaa attcacctcc tcctaagttt    7380
gaaggtagcg gcgttcctga taatgaaaat cttaaattaa gccagcaaca tgggtactgg    7440
agacgtcaag ccaggtacaa gccagtgtaa ggcggaagaa aatcagtccc agatgcttgg    7500
tacttctatt acactggaac aggaccagcc gctgacctga attggggtga tagccaagat    7560
ggtatagtgt gggtttctgc aaagggtgct gatactaaat ctagatctaa ccagggtaca    7620
agggatcctg ataagtttga ccaatacccg ctacgattct cagatggagg acctgatggt    7680
aatttccgtt gggacttcat tccaataaat cgtggtagga gtggaagatc aacagcggct    7740
tcatcagcag catctagtag agcaccgtcg cgtgatggct cgcgtggacg tagaagcgga    7800
gctgaagatg atcttatagc tcgtgcagca aagatcattc aggatcagca gaagaagggt    7860
tctcgcatta ctaaagctaa ggccgatgaa atggctcatc gccggtattg taagcgtact    7920
atcccacctg gttataaggt tgatcaagta tttggtcccc gtactaaagg taaggaggga    7980
aattttggtg atgacaagat gaatgaggag ggtattaagg atgggcgcgt tacagcaatg    8040
ctcaacctag tccctagcag ccatgcttgt ctttttggaa gtagagtgac gcccaaactt    8100
caaccagatg ggctgcactt gagatttgaa tttactactg tggtttctag ggatgatccg    8160
cagtttgata attatgtgaa aatttgtgat cagtgtgtcg atggtgtagg gactcggcca    8220
aaagacgatg aaccgagacc aaagtcacgc ccaaattcaa gacctgctac aagaacaagt    8280
tctccagcgc caagacaaca gcgtcaaaag aaggagaaga agtcaaagaa gcaggatgat    8340
gaagtagata aggcattgac ctcagatgag gagaggaaca atgcacagct ggaatttgat    8400
gatgaaccga aagtgattaa ctgggggggat tcagcacttg gagagaatga gttgtaaagc    8460
tagatttcca acttaacatc atggacgtgc gtatgctgtt tttccctact atagacttt     8520
tagcatatta ttttttgcta tttgtatggt ttattacagg tgaagattgt atgtatttgt    8580
tgtacactcg tatgttctat attatgtttt ctgtagttgt tattagtgtt gttcttgttc    8640
ttactctact gttctctttt ctttatttta gagtatcaat aagaatcaag gaagataggc    8700
atgtagtttg attacctaca tgtctatcgc cagggaaatg tctaatctgt ctacttagta    8760
gcctggaaac gaacggtaga cccttagatt ttaatttagt ttaattttta gtttagttta    8820
agttagttta gagtaggtat aaagaagcca gtgccgggc cacgcggagt acgatcgagg     8880
gtacagcact aggacgccca ctaggggaag agctaaattt tagtttaagt taagtttaat    8940
tggctaagta tagttaaaat ttataggcta gtatagagtt agagcaaaaa aaaaaaaaaa    9000
aaaaaaaaaa aaaaaaaaaa aaaaaaaaaa aaaaaaaaaa aaaaaaaaaa aaaaaaaaaa    9060
aaaaaaaaaa aaaaaaaaaa aaaaagttta aacttaatta agaattccct tggctcgagt    9120
tcgaaatcgg atgccgggac cgacgagtgc agaggcgtgc aagcgagctt ggcgtaatca    9180
tggtcatagc tgtttcctgt gtgaaattgt tatccgctca caattccaca acatacga     9240
gccggaagca taaagtgtaa agcctggggt gcctaatgag tgagctaact cacattaatt    9300
gcgttgcgct cactgcccgc tttccagtcg ggaaacctgt cgtgccagct gcattaatga    9360
atcggccaac gcgcggggag aggcggtttg cgtattgggc gctcttccgc ttcctcgctc    9420
actgactcgc tgcgctcggt cgttcggctg cggcgagcgg tatcagctca ctcaaaggcg    9480
gtaatacggt tatccacaga atcagggat aacgcaggaa agaacatgtg agcaaaaggc     9540
cagcaaaagg ccaggaaccg taaaaaggcc gcgttgctgg cgttttccca taggctccgc    9600
```

```
cccctgacg agcatcacaa aaatcgacgc tcaagtcaga ggtggcgaaa cccgacagga    9660
ctataaagat accaggcgtt tccccctgga agctccctcg tgcgctctcc tgttccgacc    9720
ctgccgctta ccggatacct gtccgccttt ctcccttcgg gaagcgtggc gctttctcat    9780
agctcacgct gtaggtatct cagttcggtg taggtcgttc gctccaagct gggctgtgtg    9840
cacgaacccc ccgttcagcc cgaccgctgc gccttatccg gtaactatcg tcttgagtcc    9900
aacccggtaa gacacgactt atcgccactg gcagcagcca ctggtaacag gattagcaga    9960
gcgaggtatg taggcggtgc tacagagttc ttgaagtggt ggcctaacta cggctacact   10020
agaagaacag tatttggtat ctgcgctctg ctgaagccag ttaccttcgg aaaaagagtt   10080
ggtagctctt gatccggcaa acaaaccacc gctggtagcg gtggtttttt tgtttgcaag   10140
cagcagatta cgcgcagaaa aaaggatct caagaagatc ctttgatctt ttctacgggg   10200
tctgacgctc agtggaacga aaactcacgt taagggattt tggtcatgag attatcaaaa   10260
aggatcttca cctagatcct tttaaattaa aaatgaagtt ttaaatcaat ctaaagtata   10320
tatgagtaaa cttggtctga cagttaccaa tgcttaatca gtgaggcacc tatctcagcg   10380
atctgtctat ttcgttcatc catagttgcc tgactccccg tcgtgtagat aactacgata   10440
cgggagggct taccatctgg ccccagtgct gcaatgatac cgcgagaccc acgctcaccg   10500
gctccagatt tatcagcaat aaaccagcca gccggaaggg ccgagcgcag aagtggtcct   10560
gcaactttat ccgcctccat ccagtctatt aattgttgcc gggaagctag agtaagtagt   10620
tcgccagtta atagtttgcg caacgttgtt gccattgcta caggcatcgt ggtgtcacgc   10680
tcgtcgtttg gtatggcttc attcagctcc ggttcccaac gatcaaggcg agttacatga   10740
tcccccatgt tgtgcaaaaa agcggttagc tccttcggtc ctccgatcgt tgtcagaagt   10800
aagttggccg cagtgttatc actcatggtt atggcagcac tgcataattc tcttactgtc   10860
atgccatccg taagatgctt ttctgtgact ggtgagtact caaccaagtc attctgagaa   10920
tagtgtatgc ggcgaccgag ttgctcttgc ccggcgtcaa tacgggataa taccgcgcca   10980
catagcagaa ctttaaaagt gctcatcatt ggaaaacgtt cttcggggcg aaaactctca   11040
aggatcttac cgctgttgag atccagttcg atgtaaccca ctcgtgcacc caactgatct   11100
tcagcatctt ttactttcac cagcgtttct gggtgagcaa aaacaggaag gcaaaatgcc   11160
gcaaaaaagg gaataagggc gacacggaaa tgttgaatac tcatactctt ccttttcaa    11220
tattattgaa gcatttatca gggttattgt ctcatgagcg gatacatatt tgaatgtatt   11280
tagaaaaata aacaaatagg ggttccgcgc acatttcccc gaaaagtgcc acctgacgtc   11340
taagaaacca ttattatcat gacattaacc tataaaaata ggcgtatcac gaggcccttt   11400
cgtc                                                                11404
```

<210> SEQ ID NO 22
<211> LENGTH: 52
<212> TYPE: DNA
<213> ORGANISM: Artificial Sequence
<220> FEATURE:
<223> OTHER INFORMATION: Primer
<400> SEQUENCE: 22
cagagcacaa gtttgatctt gtgatatctg atatgtatac agacaatgat tc            52

<210> SEQ ID NO 23
<211> LENGTH: 32
<212> TYPE: DNA
<213> ORGANISM: Artificial Sequence

```
<220> FEATURE:
<223> OTHER INFORMATION: Primer

<400> SEQUENCE: 23
tatcatagag caaagcacta catagtgcac ac                                    32

<210> SEQ ID NO 24
<211> LENGTH: 38
<212> TYPE: DNA
<213> ORGANISM: Artificial Sequence
<220> FEATURE:
<223> OTHER INFORMATION: Primer

<400> SEQUENCE: 24
actatgtagt gctttgctct atgataataa tacttacg                              38

<210> SEQ ID NO 25
<211> LENGTH: 40
<212> TYPE: DNA
<213> ORGANISM: Artificial Sequence
<220> FEATURE:
<223> OTHER INFORMATION: Primer

<400> SEQUENCE: 25
cataccaagg ccatttaata taagttttga gaattgagag                            40

<210> SEQ ID NO 26
<211> LENGTH: 31
<212> TYPE: DNA
<213> ORGANISM: Artificial Sequence
<220> FEATURE:
<223> OTHER INFORMATION: Primer

<400> SEQUENCE: 26
aacttatatt aaatggcctt ggtatgtgtg g                                     31

<210> SEQ ID NO 27
<211> LENGTH: 48
<212> TYPE: DNA
<213> ORGANISM: Artificial Sequence
<220> FEATURE:
<223> OTHER INFORMATION: Primer

<400> SEQUENCE: 27
cttaactcct ggaattacta accacgtgta ccaaataaa caacaagc                    48

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
tcagcatgga cgtgtggtta                                                  20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
aggttggcac ctatatgggg                                                  20
```

```
<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tgacttggtt tgaagatggc                                                   20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
aagagatgtt ggtaacacct                                                   20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
gacagagcac aagtttgatc                                                   20

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ggagtgaaaa caagatcacc                                                   20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
aatttaacag ttagcgtatc                                                   20

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tttgtatacg agagccatca                                                   20

<210> SEQ ID NO 36
<211> LENGTH: 20
<212> TYPE: DNA
<213> ORGANISM: Artificial Sequence
<220> FEATURE:
<223> OTHER INFORMATION: Primer
```

```
<400> SEQUENCE: 36
ggtcctacta gatgtaaggg                                              20

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
ctctctttga cctacaccat                                              20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
ttgccttcag tatgtttgtg                                              20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
agtgaagaaa gtctacctgt                                              20

<210> SEQ ID NO 40
<211> LENGTH: 20
<212> TYPE: DNA
<213> ORGANISM: Artificial Sequence
<220> FEATURE:
<223> OTHER INFORMATION: Primer

<400> SEQUENCE: 40
atttcctccg tacttcaaga                                              20

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
tgaagataat aatggcaaaa gc                                           22

<210> SEQ ID NO 42
<211> LENGTH: 21
<212> TYPE: DNA
<213> ORGANISM: Artificial Sequence
<220> FEATURE:
<223> OTHER INFORMATION: Primer

<400> SEQUENCE: 42
tcttgaaaca ctctcaattc t                                            21

<210> SEQ ID NO 43
```

```
<211> LENGTH: 20
<212> TYPE: DNA
<213> ORGANISM: Artificial Sequence
<220> FEATURE:
<223> OTHER INFORMATION: Primer

<400> SEQUENCE: 43
ggtcaccagt atatttctgc                                              20

<210> SEQ ID NO 44
<211> LENGTH: 21
<212> TYPE: DNA
<213> ORGANISM: Artificial Sequence
<220> FEATURE:
<223> OTHER INFORMATION: Primer

<400> SEQUENCE: 44
ggtcaacaat gtaattttgc t                                            21

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
cttgtcctgc tttgttaaga                                              20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
ttataggttg gcttgtacgc                                              20

<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
gcccatcctt aataccttcc                                              20

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ctcgcattac aaaggctaag                                              20

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
```

-continued gctctaactc tatactagcc t                                          21

<210> SEQ ID NO 50
<211> LENGTH: 32
<212> TYPE: DNA
<213> ORGANISM: Artificial Sequence
<220> FEATURE:
<223> OTHER INFORMATION: Primer

<400> SEQUENCE: 50
gtttgtccaa catctcttac cagtaactta cc                              32

<210> SEQ ID NO 51
<211> LENGTH: 35
<212> TYPE: DNA
<213> ORGANISM: Artificial Sequence
<220> FEATURE:
<223> OTHER INFORMATION: Primer

<400> SEQUENCE: 51
ttactggtaa gagatgttgg acaaaccgct tttac                           35

<210> SEQ ID NO 52
<211> LENGTH: 40
<212> TYPE: DNA
<213> ORGANISM: Artificial Sequence
<220> FEATURE:
<223> OTHER INFORMATION: Primer

<400> SEQUENCE: 52
ggactttgga tcattaaaca gacttttag gtctgtattg                       40

<210> SEQ ID NO 53
<211> LENGTH: 32
<212> TYPE: DNA
<213> ORGANISM: Artificial Sequence
<220> FEATURE:
<223> OTHER INFORMATION: Primer

<400> SEQUENCE: 53
aaagtctgtt taatgatcca aagtcccact ag                              32

<210> SEQ ID NO 54
<211> LENGTH: 32
<212> TYPE: DNA
<213> ORGANISM: Artificial Sequence
<220> FEATURE:
<223> OTHER INFORMATION: Primer

<400> SEQUENCE: 54
acttcaccaa catctcttac cagtaactta cc                              32

<210> SEQ ID NO 55
<211> LENGTH: 31
<212> TYPE: DNA
<213> ORGANISM: Artificial Sequence
<220> FEATURE:
<223> OTHER INFORMATION: Primer

<400> SEQUENCE: 55
ttactggtaa gagatgttgg tgaagtcact g                               31

<210> SEQ ID NO 56
<211> LENGTH: 32
<212> TYPE: DNA

<213> ORGANISM: Artificial Sequence
<220> FEATURE:
<223> OTHER INFORMATION: Primer

<400> SEQUENCE: 56
aatcaaacaa attagcacta catagtgcac ac                                32

<210> SEQ ID NO 57
<211> LENGTH: 41
<212> TYPE: DNA
<213> ORGANISM: Artificial Sequence
<220> FEATURE:
<223> OTHER INFORMATION: Primer

<400> SEQUENCE: 57
actatgtagt gctaatttgt ttgattctga taataattat g                      41

<210> SEQ ID NO 58
<211> LENGTH: 46
<212> TYPE: DNA
<213> ORGANISM: Artificial Sequence
<220> FEATURE:
<223> OTHER INFORMATION: Primer

<400> SEQUENCE: 58
cataccaagg ccacttaata taagttttaa ttattgaaag ttcttc                 46

<210> SEQ ID NO 59
<211> LENGTH: 31
<212> TYPE: DNA
<213> ORGANISM: Artificial Sequence
<220> FEATURE:
<223> OTHER INFORMATION: Primer

<400> SEQUENCE: 59
aacttatatt aagtggcctt ggtatgtgtg g                                 31

<210> SEQ ID NO 60
<211> LENGTH: 48
<212> TYPE: DNA
<213> ORGANISM: Artificial Sequence
<220> FEATURE:
<223> OTHER INFORMATION: Primer

<400> SEQUENCE: 60
cagagcacaa gtttgatctt gtgatatctg atatgtatac agacaatg               48

<210> SEQ ID NO 61
<211> LENGTH: 32
<212> TYPE: DNA
<213> ORGANISM: Artificial Sequence
<220> FEATURE:
<223> OTHER INFORMATION: Primer

<400> SEQUENCE: 61
acttccccaa catctcttac cagtaactta cc                                32

<210> SEQ ID NO 62
<211> LENGTH: 31
<212> TYPE: DNA
<213> ORGANISM: Artificial Sequence
<220> FEATURE:
<223> OTHER INFORMATION: Primer

<400> SEQUENCE: 62
ttactggtaa gagatgttgg ggaagtcact g                                 31

<210> SEQ ID NO 63
<211> LENGTH: 47
<212> TYPE: DNA
<213> ORGANISM: Artificial Sequence
<220> FEATURE:
<223> OTHER INFORMATION: Primer

<400> SEQUENCE: 63
cttaactcct ggaattacta accacgtgta ccaaataaa caacaag             47

<210> SEQ ID NO 64
<211> LENGTH: 32
<212> TYPE: DNA
<213> ORGANISM: Artificial Sequence
<220> FEATURE:
<223> OTHER INFORMATION: Primer

<400> SEQUENCE: 64
tatcaaacaa agcagcacta catagtgcac ac                            32

<210> SEQ ID NO 65
<211> LENGTH: 36
<212> TYPE: DNA
<213> ORGANISM: Artificial Sequence
<220> FEATURE:
<223> OTHER INFORMATION: Primer

<400> SEQUENCE: 65
actatgtagt gctgctttgt ttgataataa tgaaac                        36

<210> SEQ ID NO 66
<211> LENGTH: 40
<212> TYPE: DNA
<213> ORGANISM: Artificial Sequence
<220> FEATURE:
<223> OTHER INFORMATION: Primer

<400> SEQUENCE: 66
cataccaagg ccatttaata taagtcttga gtattgaaag                    40

<210> SEQ ID NO 67
<211> LENGTH: 31
<212> TYPE: DNA
<213> ORGANISM: Artificial Sequence
<220> FEATURE:
<223> OTHER INFORMATION: Primer

<400> SEQUENCE: 67
gacttatatt aaatggcctt ggtatgtgtg g                             31

<210> SEQ ID NO 68
<211> LENGTH: 32
<212> TYPE: DNA
<213> ORGANISM: Artificial Sequence
<220> FEATURE:
<223> OTHER INFORMATION: Primer

<400> SEQUENCE: 68
tgtcatataa attagcacta catagtgcac ac                            32

<210> SEQ ID NO 69
<211> LENGTH: 38
<212> TYPE: DNA
<213> ORGANISM: Artificial Sequence
<220> FEATURE:

<223> OTHER INFORMATION: Primer

<400> SEQUENCE: 69
actatgtagt gctaatttat atgacaacga atcttttg                               38

<210> SEQ ID NO 70
<211> LENGTH: 40
<212> TYPE: DNA
<213> ORGANISM: Artificial Sequence
<220> FEATURE:
<223> OTHER INFORMATION: Primer

<400> SEQUENCE: 70
cataccaagg ccacttaata taagttttga gtattgaaag                             40

<210> SEQ ID NO 71
<211> LENGTH: 32
<212> TYPE: DNA
<213> ORGANISM: Artificial Sequence
<220> FEATURE:
<223> OTHER INFORMATION: Primer

<400> SEQUENCE: 71
tatcaaacag agcagcacta catagtgcac ac                                     32

<210> SEQ ID NO 72
<211> LENGTH: 34
<212> TYPE: DNA
<213> ORGANISM: Artificial Sequence
<220> FEATURE:
<223> OTHER INFORMATION: Primer

<400> SEQUENCE: 72
actatgtagt gctgctctgt ttgataataa tcag                                   34

<210> SEQ ID NO 73
<211> LENGTH: 32
<212> TYPE: DNA
<213> ORGANISM: Artificial Sequence
<220> FEATURE:
<223> OTHER INFORMATION: Primer

<400> SEQUENCE: 73
gttgaaccaa catctcttac cagtaactta cc                                     32

<210> SEQ ID NO 74
<211> LENGTH: 35
<212> TYPE: DNA
<213> ORGANISM: Artificial Sequence
<220> FEATURE:
<223> OTHER INFORMATION: Primer

<400> SEQUENCE: 74
ttactggtaa gagatgttgg ttcaacctct tttac                                  35

<210> SEQ ID NO 75
<211> LENGTH: 32
<212> TYPE: DNA
<213> ORGANISM: Artificial Sequence
<220> FEATURE:
<223> OTHER INFORMATION: Primer

<400> SEQUENCE: 75
tattgtacaa agaagcacta catagtgcac ac                                     32

-continued

```
<210> SEQ ID NO 76
<211> LENGTH: 38
<212> TYPE: DNA
<213> ORGANISM: Artificial Sequence
<220> FEATURE:
<223> OTHER INFORMATION: Primer

<400> SEQUENCE: 76
actatgtagt gcttctttgt acaataatga tagctatg                              38

<210> SEQ ID NO 77
<211> LENGTH: 46
<212> TYPE: DNA
<213> ORGANISM: Artificial Sequence
<220> FEATURE:
<223> OTHER INFORMATION: Primer

<400> SEQUENCE: 77
cataccaagg ccatttaata taagttttta aaatagaaag tgtttc                     46

<210> SEQ ID NO 78
<211> LENGTH: 27646
<212> TYPE: DNA
<213> ORGANISM: Avian infectious bronchitis virus

<400> SEQUENCE: 78
actaaaaata gatattaata tatatctatt acactagcct tgcgctagat ttccaactta      60
acaaaacgga cttaaatacc tacagctggt cctcataggt gttccattgc agtgcacttt     120
agtgccctgg atggcacctg ccacctgtc aggttttgt tattaaaatc ttattgttgc       180
tggtatcact gcttgttttg ccgtgtctca ctttatacat ccgttgcttg ggctacctag    240
tatccagcgt cctacgggcg ccgtggctgg ttcgagtgcg aagaacctct ggttcatcta    300
gcggtaggcg ggtgtgtgga agtagcgctt cagacgtact ggttctgttg cgtgaaacgc    360
ggggtcacct cccccacat acctctaagg gcttttgagc ctagcgttgg gctacgttct     420
cgcacaaggt cggctatacg acgtttgtag ggggtagtgc caaacaaccc ctgaggtgac    480
aggttctggt ggtgtttagt gagcagacat acaatagaca gtgacaacat ggcttcaagc    540
ctaaaacagg gagtatctcc caaaccaagg gatgtcattc ttgtttccaa agacattccc    600
gaacaactct gtgacgcttt atttttctac acgtcacaca accctaagga ttacgctgat    660
gcttttgcat ttaggcaaaa gtttgaccgt aatctgcaga ctgggaagca gttcaaattt    720
gaaactgttt gtggtctctt cctattgaag ggagttgaca aataacacc tggcgtccca     780 gcaaagttt taaagccac ttctaagttg gcagatttag aagacatctt tggtgtctct      840
ccttttgcac ggaagtaccg tgaattgttg aaaacagcat gccagtggtc tcttactgta    900
gaaacactgg atgctcgtgc acaaacgctt gacgaaattt ttgactctac tgaaatactt    960
tggcttcagg tggctgcaaa aattcaagtt tcagctatgg caatgcgcag gcttgttgga   1020
gaagtaactg caaagtcat ggaagctctt ggctcaaatt tgagtgttct ctttcaaatt    1080
gttaaacaac aaatagccag aatctttcaa aaggcactgg ctattttga aaatgtgagt    1140 gaattaccac agcgtattgc agcacttaag atggccttg ccaagtgtgc caagtcaatt    1200 actgttgtg ttgtggaaag aactctagtt gttagagagt cgcaggaac ttgtcttgca    1260 agcatcaatg gtgctgttgc aaaattcttt gaagaacttc caatggctt tatgggttct   1320 aaaatcttca caacattggc cttctttaaa aagcagctg tgaaaattgt ggaaaatata   1380
ccaaatgcac caagaggtac tagaggtttt gaagtcgttg gtaacgccaa gggaacgcaa   1440
```

```
gttgttgtgc gtggcatgcg aaatgattta actctgctcg accaaaaagc tgacattcct   1500
gttgagaaag aaggttggtc tgcaattctt gaaggacatc tgtgttatgt ctttaagagt   1560
ggtgatcgtt tttatgcggc acctctttca gggaattttg cattgcatga tgtgcattgt   1620
tgtgagcgtg ttgtctgtct gtctgatggt gtaacaccag agataaatga tggactcatt   1680
ctagcagcaa tctattcatc ttttagtgtc tcagaactcg tggcagcact taaaaagggt   1740
gaaccattca agttcttggg tcataaattt gtgtatgcga aggatgcagc agtctctttc   1800
actcttgcaa aagcagccac tattgcagat gtactgaagc tgtttcaatc agctcgtgtg   1860
caaacagaag atgtgtggtc tgcatttact gaaaagtctt ttaatttctg gaaactcgca   1920
tatggaaaag tgcgtaatct tgaagaagtt gtgaagactc atttttgtaa agctcaaatg   1980
tcaattatca ttctagcagc agtgcttggc gaaggcattt ggcatcttgt ttcacaggtc   2040
atctataaag taggtggtct ttttactaga gtcgttgact tttgtgaaaa acactggaag   2100
ggtttctgtg cacaacttaa aaaggctaag ctcgttgtca cagaaactct ttgtgttctt   2160
aagggagtgg cacagcattg ttttcaacta ttgctggatg caatacattc tttgtatatg   2220
agttttaaga gtgtgcact tggtagaatt catggagact tactcttctg gaaaggggt    2280 gtacacaaaa ttgttcaaga tggcgatgaa gtttggtttg acgccattga tagtattgat   2340
gttgaagatc tgggtgttgt ccaagaaaaa cccatagatt ttgaggtttg tgaagacgta   2400
acacttccag aaaatcaacc tggtcatatg gttcaaatcg aggatgacgg aaagaactat   2460
atgttcttcc gcttcaaaag ggatgagaac atctactata caccaatgtc tcaacttggt   2520
gcaattaatg tagtttgcaa agcaggcggt aaaaccgtta cctttggaga caccattgtg   2580
aaagaaatac cgccacctga tgttgtgcct attaaggtta gcatagagtg ttgtggtgaa   2640
ccatggaata caatcttcaa gaaagcttat aaagagccca ttgaagttga aactgacctc   2700
acagtagaac aattgctctc tgtgatctat gagaaaatgt gcgacgacct caaattgttt   2760
ccagaggcac cagagccacc gccatttgag aatgtcgcac ttgttgataa aaacggtaaa   2820
gacttggatt gcataaaatc atgccatctt atctaccgtg attatgagag tgatgatgac   2880
atcgaggaag aagatgctga ggagtgtgat actgatttag aatgtgaaga agaggatgag   2940
gatactaaag tgttggctct tatacaagac cctgcaagta ataaatacc tcttcctctt    3000 gatgatgatt atagcgtctt taatggatgt attgtacata aggacgctct tgacgtcgta   3060
aatctaccat ctggtgaaga aacctttgtt gtcaacaact gctttgaggg agctgtaaaa   3120
ccactgcctc agaaagttgt tgatgttcta ggtgactggg gtgaggctgt tgatgcgcaa   3180
gagcaaattg cacaaactac ttcagaggaa acccctatca gtagtttgga ggcaactatt   3240
gagcaagttg ttgttgagga acagaaaata atttctgttg ttgaagaaga acagcaggtg   3300
gcggtctaca cacctgcaga cctacaagtt gttgaagaaa caccagatga gtttattctt   3360
attgctgatg tttccacaga agaaattgtg cctcatgaag aaaggagtc acagattgaa    3420 caggagccta ttcaagttgt taaatcacaa cgtgaaaaga aggctaaaaa gttcaaggtt   3480
aaatctacta catgtgagaa acccaaattt ttggagtaca acatgtgt gggtgaccta     3540 acggtagtga ttgccaaagc attggatgag tttaaagagt tctgcattgt aaatgctgct   3600
aatgagcata tgtctcacgg tggcggcgtt gcaaaggcaa ttgcagactt tgtggaccg    3660 gactttgttg aatattgcgc ggactatgtt aagaaacatg gtccacagca aaacttgtc    3720 acaccttcat ttgttaaagg cattcaatgt gtgaataatg ttgtaggacc tcgccatgga   3780
gacagcaact tgcgtgagaa gcttgttgct gcttacaaga gtgttcttgt aggtggagtg   3840
```

```
gttaactatg ttgtgccagt tctctcatca gggattttg gtgtagattt taaaatgtca    3900
atagatgcta tgcgcgaagc ttttaaaggt tgtgccatac gcgttctttt attttctctg    3960
agtcaagaac acatcgatta tttcgatgca acttgtaagc agaagacaat ttatcttacg    4020
gaggatggtg ttaaataccg ctctgttgtt ttaaaacctg gtgattcttt gggtcaattt    4080
ggacaggttt ttgcaagaaa taaggtagtc ttttcggctg atgatgttga ggataaagaa    4140
atcctcttta tacccacaac tgacaagact attcttgaat attatggttt agatgcgcaa    4200
aagtatgtaa tatatttgca aacgcttgcg cagaaatggg atgttcaata tagagacaat    4260
tttgttatat tagagtggcg tgacggaaat tgctggatta gttcagcaat agtgctcctt    4320
caagctgcta agattaggtt taaaggtttt cttgcagaag catgggcaca acttttgggt    4380
ggagacccaa ctgattttgt agcctggtgc tatgcaagtt gcaatgctaa tgttggtgag    4440
ttttcagatg ctaattggct tcttgctaat ttggcagaat actttgatgc tgattacacg    4500
aatgcattcc ttaagaggcg tgtgtcatgt aactgtgggg ttaagaattg tgaagttaga    4560
ggccttgaag cttgtattca accagtaaag gcacccaatc ttcttcattt caagactcag    4620
tacacaaatt gtacagtgtg tgatgcaaat agtgtggatg aggtggtaga ggcctcacta    4680
ccatatctgt tgctccttgc tactgatggt cctactacag tggattgtga tgaaaatgct    4740
gtagggaatg ttgttttcat tggctctact aatagtggcc attgttacac gcaagccatt    4800
ggtaaggctt ttgataatct tgctaaggat agaaaatttt caaagaattc gccatacatt    4860
acagcaatgt atacgcgctt ctctcttaag agtgaaagct ctctgtctgt tgttaaacag    4920
agtaagagta aaactaaagt agtaaaagaa gatgttgcca accttgttac tagttctaaa    4980
gccagttttg atgatcttac tgactttgaa cattggtatg atagtaacat ctatgaaagt    5040
cttaaagttc aggaaatacc tgtgaatttg gatgagtatg tgtcatttac aacgaaagaa    5100
gatactaagt tgccactgac acttaaagtt agaggtatca aatcagttgt tgactttatt    5160
tcaagagacg gtttctctta taagttaaca cctgacattg aagaaaattc aaaagcgcca    5220
gtctactacc cagtcttaga ctctattagt cttaaggcaa tatgggtaga cggcagtgct    5280
aattttgttg ttggtcatcc aaactactat agtaagtctc ttcgcattcc tactttttgg    5340
gaaaatgcag agagctttgt taagataggt gacaaagttg atggtgtaac tatgggcctt    5400
tggcgtgcag aacagcttaa caaacctaat cttgaaagaa ttttcaacat tgctaagaaa    5460
gctattgttg gatccagtgt tgttactaca caatgtagta aattaattag taaagcagct    5520
acattcattg ctgataaagt aggtgggggt gtagttcgta atattacaga tagaattaag    5580
ggtctttgtg gatttacacg tgggcatttt gaaagaaaat tgtctccaca attcataaaa    5640
acacttatat tcttcttctt ttactttgta aaggctagtg ctaagagtgt tgccactagt    5700
tataagcgtg tgttatgtaa ggtggttttt accacgctat ttatattatg gtttatgtac    5760
acaagcaaac cagtaacttt tactggaaca cgtgtgctag acttcttatt tgagggttct    5820
ttatgtggtc cctataatga ctatggtaaa gactcatttg acgtactacg ctattgtgga    5880
gatgatttta cttgtcgtgt atgtttacat gataaagatt cacttcattt gtataagcat    5940
gcttatagcg tagaacaggt ttataaagat gcagcttctg gcattagttt taattggaat    6000
tggctttatt tggtctttct aatattattt gttaaaccag tagcaggttt cgttattatt    6060
tgctattgtg ttaagtactt ggtattgagt tcaactgtgt tgcaaactgg tgtaggtttt    6120
atggactggt ttattcaaac agttttttact cactttaatt ttatgggtgc aggtttctat    6180
```

```
ttctggctct tttataaatt gtacatacag gttcatcata tactgtattg taaggatata    6240
acatgtgaag tgtgtaagag agttgcacgc agtaacaggc atgaggttag tgttgttgtt    6300
ggtggacgca agcaaattgt gcatgtgtac actaactctg gttacaactt tgtaagaga     6360 cataattggt attgtaggaa ttgtgatgta tatggtcacc aaaacacatt tatgtctcct    6420
gaagttgctg gcgagctttc tgaaaagctt aaacgccatg ttaaacctac agcacatgct    6480
taccacgttg tggatgaggc ttgcgtagtt gatgattttg ttaacttaaa atacaaagct    6540
gcaactcctg gtaaggatgg tgcacctcct gcagttaaat gtttcagtgt tacagatttc    6600
ttgaagaaag ctgttttttct taaggatgca ctgaaatgtg aacaaatatc taatgatggt    6660
tttatagtgt gtaatacgca gagtgcgcat gctttagagg aagcaaagaa tgcagccatc    6720
tattatgcgc aatacctgtg taaacctata cttatactcg accaggcact ctaccagaat    6780
ttaatagtgg aacctgtatc gaagagcgtt gtcaacaaag tgtgtgacat tttgtctagg    6840
ataatttctg tagatactgc atctttggat tataaagcag gtacaattcg tgatgccttg    6900
ctgtctgtta ctaaagatga agaagctgta gatatggcta tcttctgtca taatcatgaa    6960
gttgaatata caggtgatgg ttttactaat gttataccgt catatggtat agacactgat    7020
aaattaacac ctcgtgatag aggggttttg ataaatgcag atgcttctgt tgctaactta    7080
agagttaaaa atgctccgcc ggtagtatgg aagttctctg atcttattaa gttgtctgac    7140
agttgtctta aatattttaat ctcagcaact gtcaagtcag ggtctcgttt ctttataaca    7200
agatctggtg ctaaacaaat tttttcttgt agtactcaga aattgttggt agagaaaaag    7260
gctggtggtg tcattagtgg tacctttaat tggtttaaga gttgttgtaa atggctcttg    7320
atcttctatg tgcttttttac attgtgttgt ttgggttgtt atcatatgga gacgaataaa    7380
agttttgttc atcctatgta tgatgttaac tctacaatgc atgttgaagg ctttaaggtt    7440
atagataaag gtgttattag agacattgta ccagaggatg cttgtttctc taataagttt    7500
gctaactttg atgcattttg gggtaaacca tatgtgaata gtagagactg tccaattgtt    7560
acagcagtca tagatggcgc tggaacaata gcagctggtg ttcctggttt tgtagactgg    7620
gttcttgatg tgttatgtt tgtacacatg acacaaacag aaagaaaacc ctggtacatt    7680
cccacgtggt ttaacagaga aattgttggt tacactcagg attcaattat tactgaaggt    7740 agttttttata catctatagc tttgttttca gctaggtgtt tatatttaac agccagcaat    7800
acaccacaat tgtattgttt taatggtcat aatgatgctc ctggagcctt accatttagc    7860
agtatcactc cacacagggt ctacttccaa ccaaatggtg ttaggcttat aattcctcaa    7920
cagataatgc acacaccta cgtagtaaag ttttttatcag acagctattg tagaggtagt    7980
gtatgtgagt atactaaacc gggttattgt gtctcactaa attcccaatg gttttattt     8040 aatgacgaat acacaagtaa accaggagta ttctgtggtt ctactgttag agaacttatg    8100
tttaatatgg ttagtacatt tttactggt gtcaaccta atatttatat gcagctggcg     8160
actatgttct taatactagt tgttgttgtg ttaattttttg caatggttat aaagtttcaa    8220
ggtgttttta agcttatgc aaccattgtg tttacaataa tgctagttttg ggttgttaat    8280 gcatttattt tgtgtgtaca tagttataat agtgttgtgg ctgttatact actagtaatc    8340
tattgttatg catcattggt tacaagtcgt aatactgcta ataataatgca ttgttggctt    8400 gtgttttacct ttggtttaat tgtacccata tggttggcgt gttgctacct ggcatttgtt    8460
ttatatatgt acacaccatt gttttttctgg tgttacggta ctactaaaaa cactcgtaaa    8520
ttgtatgatg gcaacgagtt tgttggtact tatgatcttg ctgcgaagag caccctttgtt    8580
```

```
attcgcggtc ctgaatttgt taagcttacg aacgagatag gtgataagtt tgaacactat   8640
ctctcagcgt atgctagact taaatactac tcaggcactg gcagtgaaca agattatctg   8700
caagcttgtc gtgcatggtt agcttatgct ttggaccaat atagaaatag tggtgtggaa   8760
attgtgtata ctccaccacg ttactctatt ggtgttagta gattacaggc cggttttaag   8820
aaactagttt ctcctagtag tgttgttgaa aagtgcattg ttagtgtctc ttatagaggt   8880
aataatctta atggactgtg gctaggtggt actatctact gtccgcgaca tgttctaggc   8940
aagttctcag gtgaccaatg gaatgatgta cttaaccttg ctaataatca tgagtttgaa   9000
gttgtaactc aaaataatgt tactttgaat gttgtcagta ggaggctaaa aggtgcagtt   9060
ttgattttac aaactgctgt tgctaatgct gaaactccaa agtataagtt tgttaaagcc   9120
aattgtggag atagttttac gattgcttgt tcctatggtg gtacagttgt tggactctac   9180
cctgttacta tgcgctctaa tggtactatt agggcgtctt tcttagcagg agcgtgtggt   9240
tctccaggtt ttaatataga aaagggtgta gttaactttt attatatgca ccatcttgag   9300
ttgcctaatg cattacacac aggaactgac ctaatgggag agttctatgg tggttatgtg   9360
gacgaagagg ttgcacaaag ggtgccacca gataatttag ttactaacaa tattgtagca   9420 tggcttatg ccgcaattat tagtgttaag gagagtagtt tctcactgcc taaatggttg   9480
gatagtacta ctgtcagtgt tgaagactgc aataagtggg ctggtgataa tggttttaca   9540 ccatttttcta ctagtactgc tattactaaa ttaagtgcta taacaggagt agatgtttgt   9600
aaactccttc gcactattat ggtaaaaagt agtcaatggg gtagtgatcc cattttagga   9660
caatataatt ttgaagatga attgacacca gagtccgttt ttaatcagat aggtggtgtt   9720
agattacagt cttcttttgt aagaagagcc acatcctggt tttggagtag atgtgtgtta   9780
gcttgcttct tatttgtgtt gtgtgctatt gtcttgttta cggcagtgcc acttaaatat   9840
tatgtacatg cagccgttat tttgttaaca gctgtgctct tcatttcttt tactgttaaa   9900
catgttatgg catatatgga tacttttcta ctgccaacat tgcttacagt cattattgga   9960
gtttgtgctg aagtaccttt catctacaat actctaatta gtaggatagt tgtctttgtt  10020
agtcaatggt atgatcctgt agtctttgat actatggtac catggatgtt cttgccacta  10080
gtgttgtaca cagcatttaa gtgtgtgcag ggttgctata gtgtgaattc tttcaatact  10140
tctttgctag tactgtacca gttcttgaag ttaggctttg ttatttatgc ctcttctagc  10200
acgctggcag catacacaga aggtaattgg gatttatttt ttgaattagt tcacactact  10260
gtgttggcta atgttagtag taattcctta ataggtttgt ttgtgttcaa gttagctaag  10320
tggatgttgt attattgtaa tgctacatac tttaataatt atgtgctaat ggctgtcatt  10380
attaatggct ttggttggct cttcacttgt tactttggag tttattggtg gattaataag  10440
gtttttggtt taaccttagg taaatatgaa ttcaaagttt cagtagacca atataggtat  10500
atgtgtcttc ataagataaa ttcgcctaaa actgtgtggg aagttttttc gacaaatata  10560
cttatacaag gaattggtgg tgatcgtgtg ttgcctatag ctacagtgca atctaaattg  10620
agtgatgtaa agtgtacaac tgttgttttta atgcagcttt tgactaagct taatgttgaa  10680
gcaaattcaa aaatgcatgc ttatcttgtt gagttacaca taaaatcct cgcatctgat  10740 gatgttggag agtgcatgga taatttattg ggtatgctta taacactatt ttgtatagat  10800
tctactattg atttgggtga gtattgtgat gatatactta agaggtcaac tgtattacaa  10860
tcggttactc aagagttttc gcacatacccc tcgtatgctg aatatgaaag agctaagagt  10920
```

```
atttatgaaa aggttttagc cgattctaaa aatggtggtg taacacagca agagcttgct  10980
gcatatcgta aagctgccaa tattgcaaag tcagttttg atagagactt ggctgttcaa   11040
aagaagttag atagcatggc agaacgtgct atgacaacaa tgtataaaga ggcgcgtgta  11100
actgatagaa gagcaaaatt agtttcatca ttacatgcac tactttttc aatgcttaag   11160
aaaatagatt ctgagaagct taatgtctta tttgaccagg cgaatagtgg tgttgtaccc  11220
ctagcaactg ttccaattgt ctgtagtaat aagcttaccc tcgttatacc agacccagag  11280
acgtgggtca agtgtgtgga gggtgtgcat gttacatatt caacagttgt ttggaatata  11340
gactgtgtta ctgatgccga tggcacagag ttacacccca cttctacagg tagtggattg  11400
acttactgta aagtggtga taatatagca tggcctttaa aggttaactt gactaggaat   11460
gggcataata aggttgatgt tgccttgcaa aataatgagc ttatgcctca cggtgtaaag  11520
acaaaggctt gcgtagcagg tgtagatcaa gcacattgta gcgttgagtc taaatgttat  11580
tatacaagta ttagtggcag ttcagttgta gctgctatta cctcttcaaa tccaaatctg  11640
aaagtagcct ctttttgaa tgaggcaggt aatcagattt atgtagactt agacccacca   11700
tgtaaatttg gtatgaaagt gggtgataag gttgaagttg tttacctgta ttttataaaa   11760
aatacgaggt ctattgtaag aggtatggta cttggtgcta tatctaatgt tgttgtgtta   11820
caatctaaag gtcatgagac agaggaagtg gatgctgtag gcattctctc actttgttct   11880
tttgcagtag atcctgcgga tacatattgt aaatatgtgg cagcaggtaa tcaacctta    11940
ggtaactgtg ttaaaatgtt gacagtacat aatggtagtg gttttgcaat aacatcaaag  12000
ccaagtccaa ctccggatca ggattcttat ggaggagctt ctgtgtgtct ttattgtaga  12060
gcacatatag cacaccctgg cggagcagga aatttagatg gacgctgtca atttaaaggt  12120
tcttttgtgc aaatacctac tacggagaaa gatcctgttg gattctgtct acgtaacaag  12180
gtttgcactg tttgtcagtg ttggattggt tatggatgtc agtgtgattc acttagacaa  12240
cctaaacctt ctgttcagtc agttgctgtt gcatctggtt ttgataagaa ttatttaaac  12300
gggtacgggg tagcagtgag gctcggctga tacccttgc taatggatgt gaccccgatg    12360
ttgtaaagcg agccttttgat gtttgtaata aggaatcagc cggtatgttt caaaatttga   12420
agcgtaactg tgcacgattc caagaagtac gtgatactga agatggaaat cttgagtatt  12480
gtgattctta tttgtggtt aaacaaacca ctcctagtaa ttatgaacat gagaaagctt    12540
gttatgaaga cttaaagtca gaagtaacag ctgatcatga tttcttgtg ttcaataaga   12600
acatttataa tattagtagg cagaggctta ctaagtatac tatgatggat ttttgctatg  12660
ctttgcggca ctttgaccca aaggattgcg aagttcttaa agaaatactt gtcacttatg  12720
gttgtataga agattatcac cctaagtggt ttgaagagaa taaggattgg tacgacccaa  12780
tagaaaaccc taaatattat gccatgttgg ctaaaatggg acctattgta cgacgtgctt   12840
tattgaatgc tattgagttc ggaaacctca tggttgaaaa aggttatgtt ggtgttatta   12900
cacttgataa ccaagatctt aatggcaaat tttatgattt tggtgatttt cagaagacag  12960
cgcctggtgc tggtgttcct gtttttgata cgtattattc ttacatgatg cccatcatag   13020
ccatgactga tgccgttggca cctgagaggt attttgaata tgatgtgcat aagggttata  13080
aatcttatga tctcctcaag tatgattata ctgaggagaa acaagagttg tttcagaagt  13140
actttaagta ttgggatcaa gagtatcacc ctaactgtcg cgactgtagt gatgacaggt  13200
gtttgataca ttgtgcaaac ttcaacatct tgttttctac acttgtaccg cagacttctt   13260
tcggtaatt gtgtagaaag gttttttgttg atggtgtacc atttatagct acttgtggct  13320
```

```
atcattctaa ggaacttggt gttattatga atcaagataa caccatgtca ttttcaaaaa  13380
tgggtttgag tcaactcatg cagtttgttg gagatcctgc cttgttagtg gggacatcca  13440
ataaattagt ggatcttaga acgtcttgtt ttagtgtttg tgctttagcg tctggtatta  13500
ctcatcaaac ggtaaaacca ggtcacttta acaaggattt ctacgatttt gcagagaagg  13560
ctggtatgtt taaggaaggt tcttctatac cacttaaaca tttcttctac ccacagactg  13620
gtaatgctgc tataaacgat tatgattatt atcgttataa caggcctacc atgtttgata  13680
tacgtcaact tctattttgt ttagaagtga cttctaaata ttttgaatgt tatgaaggcg  13740
gctgtatacc agcaagccaa gttgtagtta acaatttaga taagagtgca ggttatccgt  13800
tcaataagtt tggaaaggcc cgtctctatt atgaaatgag tctagaggag caggaccaac  13860
tctttgagag tacaaagaag aacgtcctgc ctactataac tcagatgaat ttaaaatatg  13920
ccatatccgc gaaaaataga gcgcgtacag tggcaggtgt gtctatcctt tctactatga  13980
ctaataggca gttcatcag aagattctta agtctatagt caacactaga aacgctcctg  14040
tagttattgg aacaaccaag ttttatggcg gttgggataa catgttgaga aaccttattc  14100
agggtgttga agacccgatt cttatgggtt gggattatcc aaagtgtgat agagcaatgc  14160
ctaatttgtt gcgtatagca gcatctttag tactcgctcg taaacacact aattgttgta  14220
cttggtctga acgcgtttat aggttgtata atgaatgcgc tcaggtttta tctgaaactg  14280
tcttagctac aggtggtata tatgtgaaac ctggtggtac tagcagtgga gatgctacta  14340
ctgcttatgc aaacagtgtt ttcaacataa tacaagccac atctgctaat gttgcgcgtc  14400
ttttgagtgt tataacgcgt gatattgtat atgatgacat taagagcttg cagtatgaat  14460
tgtaccagca ggtttatagg cgagtcaatt ttgacccagc atttgttgaa agttttatt  14520 cttatttgtg taagaatttc tcattgatga tcttgtctga cgacggtgtt gtttgttata  14580
acaacacatt agccaaacaa ggtcttgtag cagatatttc tggttttaga gaagttctct  14640
actatcagaa caatgttttt atggctgatt ctaaatgttg ggttgaacca gatttagaaa  14700
aaggcccaca tgaattttgt tcacagcaca caatgttagt ggaggttgat ggtgagccta  14760
gatacttgcc atatccagac ccatcacgta ttttgtgtgc atgtgttttt gtagatgatt  14820
tggataagac agaatctgtg gctgttatgg agcgttatat cgctcttgcc atagatgcgt  14880
acccactagt acatcatgaa aatgaggagt acaagaaggt attctttgtg cttctttcat  14940
acatcagaaa actctatcaa gagctttctc agaatatgct tatggactac tcttttgtaa  15000
tggatataga caagggtagt aaattttggg agcaggagtc tatgaaaat atgtatagag  15060 cccctacaac attacagtct tgtggcgttt gtgtagtgtg taatagtcaa actatattgc  15120
gctgtggtaa ttgtattcgc aaaccatttt tgtgttgtaa gtgttgctat gaccatgtca  15180
tgcacacaga ccacaaaaat gttttgtcta taaatcctta catttgctca cagccaggtt  15240
gtggtgaagc agatgttact aaaattgtacc tcggaggtat gtcatacttc tgcgtaatc  15300 ataaaccaaa gttatcaata ccgttagtat ctaatggtac agtgtttgga atttacaggg  15360
ctaattgtgc aggtagcgaa aatgttgatg attttaatca actagctact actaattggt  15420
ctactgtgga accttatatt ttggcaaatc gttgtgtaga ttcgttgaga cgctttgctg  15480
cagagacagt aaaagctaca gaagaattac ataagcaaca atttgctagt gcagaagtga  15540
gagaagtact ctcagatcgt gaattgattc tgtcttggga gccaggtaaa accaggcctc  15600
cattgaatag aaattatgtt ttcactggct ttcactttac tagaactagt aaagttcagc  15660
```

```
tcggtgattt tacatttgaa aaaggtgaag gtaaggacgt tgtctattat cgagcgacgt   15720
ctactgctaa attgtctgtt ggagacattt ttgttttaac ctcacacaat gttgtttctc   15780
ttatagcgcc aacgttgtgt cctcagcaaa ccttttctag gtttgtgaat ttaagaccta   15840
atgtgatggt acctgcgtgt tttgtaaaca acattccatt gtaccattta gtaggcaagc   15900
agaagcgtac tacagtacaa ggccctcctg gcagtggtaa atcccatttt gctataggat   15960
tggcggctta ctttagtaac gcccgtgtcg ttttttactgc atgctctcat gcagctgttg   16020
atgctttatg tgaagaagct tttaagtttc ttaaagtaga tgattgcact cgtatagtac   16080
ctcaaaggac tactatcgat tgcttctcta agtttaaagc taatgacaca ggcaaaaagt   16140
acatttttag tactattaat gccttgccag aagttagttg tgacattctt ttggttgacg   16200
aggttagtat gttgaccaat tacgaattgt cttttattaa tggtaagata aactatcaat   16260
atgttgtgta tgtaggtgat cctgctcaat taccggcgcc tcgtacgttg cttaacggtt   16320
cactctctcc aaaggattat aatgttgtca caaaccttat ggtttgtgtt aaacctgaca   16380
ttttccttgc aaagtgttac cgttgtccta agaaaattgt agatactgtt tctactcttg   16440
tatatgatgg aaagtttatt gcaaataacc cggaatcacg tcagtgtttc acggttatag   16500
ttaataatgg taattctgat gtaggacatg aaagtggctc agcctacaac acaactcaat   16560
tagaatttgt gaaagatttt gtctgtcgca ataaggaatg gcgggaagca acattcattt   16620
caccttataa tgctatgaac cagagagcct accgtatgct tggacttaat gttcagacag   16680
tagactcgtc tcaaggttcg gagtatgatt atgttatctt ttgtgttact gcagattcgc   16740
agcatgcact gaatattaac agattcaatg tagcgcttac aagagccaag cgtggtatac   16800
tagttgtcat gcgtcagcgt gatgaactat attcagctct taagtttata gagcttgata   16860
gtgtagcaag tctgcaaggt acaggcttgt ttaaaatttg caacaaagag tttagtggtg   16920
ttcatccagc ttatgcagtc acaactaagg ctcttgctgc aacttataaa gtaaatgatg   16980
aacttgctgc acttgttaac gtggaagctg gttcagaaat aacatataaa catcttattt   17040
ctttgttagg gtttaagatg agtgttaatg ttgaaggctg ccacaacatg tttataacac   17100
gtgatgaggc tatccgcaac gtaagaggtt gggtaggttt tgatgtagaa gcaacacatg   17160
cttgcggtac taacattggt actaacctgc cttttccaagt aggtttctct actggtgcag   17220
gctttgtagt tacgcctgag ggacttgtag atacttcaat aggcaataat tttgagcctg   17280
tgaattctaa agcacctcca ggtgaacaat ttaatcactt gagagcgtta ttcaaaagtg   17340
ctaaaccttg gcatgttgta aggccaagga ttgtgcaaat gttagcggat aacctatgca   17400
acgtttcaga ttgtgtagtg tttgtcacgt ggtgtcatgg cctagaacta accactttgc   17460 gctatttgt taaaataggc aaggaccaag tttgttcttg cggttctaga gcaacaactt   17520
ttaattctta tactcaggct tatgcttgtt ggaagcattg cttgggtttt gattttgttt   17580
ataatccact cttagtggat attcagcagt ggggttattc tggtaaccta caatttaacc   17640
atgatttgca ttgtaatgtg catggacacg cacatgtagc ttctgcggat gctattatga   17700
cgcgttgtct tgcaattaat aatgcatttt gtcaagatgt caactgggat ttaacttacc   17760
ctcatatagc aaaatgaggat gaagtcaatt ctagctgtag atatttacaa cgcatgtatc   17820
ttaatgcatg tgttgatgct cttaaagtta acgttgtcta tgatataggc aaccctaaag   17880
gtataaaatg tgttagacgt ggagacttaa attttagatt ctatgataag aatccaatag   17940
tacccaatgt caagcagttt gagtatgact ataatcagca caaagataag tttgctgatg   18000
gtctttgtat gttttggaat tgtaatgtgg attgttatcc cgacaattcc ttagtttgta   18060
```

```
ggtacgacac acgaaatttg agtgtgttta acctacctgg ttgtaatggt ggtagcttgt   18120
atgtcaacaa gcatgcattc cacacaccta aatttgatcg cactagcttt cgtaatttga   18180
aagctatgcc attcttttc tatgactcat cgccttgcga gaccattcaa gtggatggag    18240
ttgcgcaaga ccttgtgtca ttagctacga aagattgtat cacaaaatgc aacataggcg   18300
gtgctgtttg taaaaagcac gcacaaatgt atgcagattt tgtgacttct tataatgcag   18360
ctgttactgc tggttttact ttttgggtta ctaataattt taacccatat aatttgtgga   18420 aaagttttc agctctccag tctatcgaca atattgctta taatatgtat aagggtggtc    18480
attatgatgc tattgcagga gaaatgccca ctatcgtaac tggagataaa gtttttgtta   18540
tagatcaagg cgtagaaaaa gcagttttt ttaatcaaac aattctgcct acatctgtag    18600
cgtttgagct gtatgcgaag agaaatattc gcacactgcc aaacaaccgt attttgaaag   18660
gtttgggtgt agatgtgact aatggatttg taatttggga ttacacgaac caaacaccac   18720
tataccgtaa tactgttaag gtatgtgcat atacagacat agaaccaaat ggcctaatag   18780
tgctgtatga tgatagatat ggtgattacc agtcttttct ggctgctgat aatgctgttt   18840
tagtttctac acagtgttac aagcggtatt cgtatgtaga aataccgtca aacctgcttg   18900
ttcagaacgg tattccgtta aaagatggag cgaacctgta tgtttataag cgtgttaatg   18960
gtgcgtttgt tacgctacct aacacattaa acacacaggg tcgcagttat gaaacttttg   19020
aacctcgtag tgatgttgag cgtgattttc tcgacatgtc tgaggagagt tttgtagaaa   19080
agtatggtaa agaattaggt ctacagcaca tactgtatgg tgaagttgat aagccccaat   19140
taggtggttt acacactgtt ataggtatgt gcagacttt acgtgcgaat aagttgaacg    19200
caaagtctgt tactaattct gattctgatg tcatgcaaaa ttattttgta ttggcagaca   19260
atggttccta caagcaagtg tgtactgttg tggatttgct gcttgatgat ttcttagaac   19320
ttcttaggaa catactgaaa gagtatggta ctaataagtc taaagttgta acagtgtcaa   19380
ttgattacca tagcataaat tttatgactt ggtttgaaga tggcattatt aaaacatgtt   19440
atccacagct tcaatcagca tggacgtgtg gttataatat gcctgaactt acaaagttc    19500 agaattgtgt tatggaacct tgcaacattc ctaattatgt tgttgaata gcgttgccaa    19560 gtggtattat gatgaatgtg gcaaagtata cacaactctg tcaatacctt tcgaaaacaa   19620
caatgtgtgt accgcatagt atgcgagtaa tgcatttgg agctggaagt gacaaaggag    19680
tggctccagg tagtactgtt cttaaacaat ggctcccaga agggacactc cttgtcgata   19740
atgatattgt agactatgtg tctgatgcac atgtttctgt gctttcagat tgcaataaat   19800
ataagacaga gcacaagttt gatcttgtga tatctgatat gtatacagac aatgattcaa   19860
aaagaaagca tgaaggcgtg atagccaata atggcaatga tgacgttttc atatatctct   19920 caagtttct acgcaataat ttggctctgg gaggcagttt tgctgtaaaa ttaacagaga    19980
caagttggca tgagagttta tatgacattg cacaggattg tgcatggtgg acaatgttct   20040
gtacagcagt gaatgcatct tcttcagaag cattcctgat tggtgttaat tacttgggtg   20100
caagtgcaaa ggttaaagtt agtggaaaaa cactgcacgc aaattatata ttttggagga   20160
attgtaatta tttacaaacc tctgcttata gtatatttga tgttgctaag tttgatttga   20220
gattgaaagc aacgccagtt gttaatttga aaactgaaca aaagacagac ttagtctta    20280 atttaattaa gtgtggtaag ttactggtaa gagatgttgg taacaccctct tttactagtg   20340 actcttttgt gtgcactatg tagtgctgtt ttgtatgaca gtagttctta cgtgtactac   20400
```

```
taccaaagtg ccttcagacc acctgatggt tggcatttac atgggggtgc gtatgcggtt    20460
gttaatattt ctagtgaatc taataatgca ggctcttcat ctgggtgtac tgttggtatt    20520
attcatggtg gtcgtgttgt taatgcttct tctatagcta tgacggcacc gtcatcaggt    20580
atggcttggt ctagcagtca gttttgtact gcatactgta acttttcaga tactacagtg    20640
tttgttacac attgttataa acatgttggg tgtcctataa ctggcatgct tcaacagcat    20700
tctatacgtt tttctgctat gaaaaatggc cagccttttt ataatttaac agttagtgta    20760
gctaagtacc ctacttttaa atcatttcag tgtgttaata atttaacatc cgtatattta    20820
aatggtgatc ttgtttacac ctctaatgag accacagatg ttacatctgc aggtgtttat    20880 tttaagctg gtggacctat aacttataaa gttatgagag aagttagagc cctggcttat    20940
tttgttaatg gtactgcaca agatgttatt ttgtgtgatg gccacctag aggcttgtta    21000 gcatgccagt ataatactgg caattttca gatggctttt atccttttac taatagtagt    21060
ttagttaagc agaagtttat tgtctatcgt gaaaatagtg ttaatactac ttttacgtta    21120
cgcaatttca cttttcataa tgagactggc gccaaccca atcctagtgg tgttcagaat    21180
attcaaactt accaaacaca aacagctcag agtggttatt ataatttaa ttttccttt    21240 ctgagtagtt ttgtttataa ggagtctaat tttatgtatg atcttatca cccaagttgt    21300 aattttagac tagaaactat taataatggt ttgtggttta attcacttc agtttcaatt    21360 gcttacggtc ctcttcaagg tggttgcaag caatctgtct ttagtggtag agcaacctgt    21420
tgttatgctt actcatatgg aggtccttg ctgtgtaaag gtgttattc aggtgagtta    21480 ggtcataatt ttgaatgtgg actgttagtt tatgttacta agagcggtgg ctctcgtata    21540
caaacagcca ctgaaccgcc agttataact caacacaatt ataataatat tactttaaat    21600
acttgtgttg attataatat atatggcaga actggccaag gttttattac taatgtaacc    21660
gactcagctg ttagttataa ttatctagca gacgcaggtt tggctatttt agatacatct    21720
ggttccatag acatctttgt tgtacaaggt gaatatggtc ttacttatta taaggttaac    21780
ccttgcgaag atgtcaacca gcagtttgta gtttctggtg gtaaattagt aggtattctt    21840
acttcacgta atgagactgg ttctcagctt cttgagaacc agttttacat taaaaatcact    21900 aatggaacac gtcgttttag acgttctatt actgaaaatg ttgaaaattg cccttatgtt    21960
agttatggta agttttgtat aaaacctgat ggttcaattg ccacaatagt accaaaacaa    22020
ttggaacagt ttgtggcacc tttacttaat gttactgaaa atgtgctcat acctaacagt    22080
tttaatttaa ctgttacaga tgagtacata caaacgcgta tggataaggt ccaaattaat    22140
tgtctgcagt atgtttgtgg caattctctg gattgtagag atttgtttcg acaatatggg    22200
catgtttgtg acaacatatt gtctgtagta aatagtattg tcaaaaaga agatatggaa    22260 cttttgaatt tctattcttc tactaaaccg gttggtttta atacaccatt tcttagtaat    22320
gttagcactg gtgagtttaa tatttctctt ctgttaacaa ctcctagtag tcctagaagg    22380
cgttctttta ttgaagacct tctatttaca agcgttgaat ctgttggatt accaacagat    22440
gacgcataca aaaattgcac tgcaggacct ttaggttttc ttaaggacct tgcgtgtgct    22500
cgtgaatata atggtttgct tgtgttgcct cccattataa cagcagaaat gcaaactttg    22560
tatactagtt ctctagtagc ttctatggct tttggtggta ttactgcagc tggtgctata    22620
ccttttgcca cacaactgca ggctagaatt aatcacttgg gtattaccca gtcacttttg    22680
ttgaagaatc aagaaaaaat tgctgcttcc tttaataagg ccattggtcg tatgcaggaa    22740
ggttttagaa gtacatcttt agcattacaa caaattcaag atgttgttaa taagcagagt    22800
```

```
gctattctta ctgagactat ggcatcactt aataaaaatt ttggtgccat ttcttctgtg   22860
attcaagaaa tctaccagca acttgacgcc atacaagcaa atgctcaagt ggatcgtctc   22920
ataactggta gattgtcatc actttctgtt ttagcatctg ctaagcaggc ggagtatatt   22980
agagtgtcac aacagcgtga gttagctact cagaagatta atgagtgtgt taagtcacag   23040
tccattaggt actccttttg tggtaatgga cgacatgttt taaccatacc gcaaaatgca   23100
cctaatggta tagtgtttat acactttct  tacactccag atagttttgt taatgttact   23160
gcaatagtgg gttttttgtgt aaagccagct aatgctagtc agtatgcaat agtacccgct   23220
aatggtaggg gtattttcat acaagttaat ggtagttact acatcactgc acgagatatg   23280
tatatgccaa gagctattac tgcaggagat atagttacgc ttacttcttg tcaagtaaat   23340
tatgtaagtg taaataagac cgtcattact acattcgtag acaatgatga ttttgatttt   23400
aatgacgaat tgtcaaaatg gtggaatgat actaagcatg agctaccaga ctttgacaaa   23460
ttcaattaca cagtacctat acttgacatt gatagtgaaa ttgatcgtat tcaaggcgtt   23520
atacagggtc ttaatgactc tctaatagac cttgaaaaac tttcaatact caaaacttat   23580
attaagtggc cttggtatgt gtggttagcc atagcttttg ccactattat cttcatctta   23640
atattaggat gggttttctt catgactggg tgttgtggtt gttgtgtgg atgctttggc   23700 attatgcctc taatgagtaa gtgtggtaag aaatcttctt attacacgac ttttgataac   23760
gatgtggtaa ctgaacaata cagacctaaa aagtctgttt aatgatccaa agtcccacgt   23820
ccttcttaat agtattaatt ttgctttggt gtaaacttgt actaagttgt tttagagagt   23880
ttattatagc gcttcaacaa ctaacacaag ttttactcca aattatcgat agtaatttac   23940
agtctagact gaccctttgt cacagtctag actaatgtta aacttagaag caattattga   24000
aactggtgag caagtgattc aaaaaatcag tttcaattta cagcatattt caagtgtatt   24060
aaacacagaa gtatttgacc cctttgacta ttgttattac agaggaggta attttttggga   24120 aatagagtca gctgaagatt gttcaggtga tgatgaattt attgaataag tcgctagagg   24180
aaaatggaaa ttttctaaca gcgctttaca tatttgtagg attttttagca ctttatcttc   24240 taggtagagc acttcaagca tttgtacagg ctgctgatgc ttgttgttta ttttggtata   24300
catgggtagt aattccagga gctaagggta cagccttttgt atacaagtat acatatggta   24360
gaaaacttaa caatccggaa ttagaagcag ttattgtcaa cgagtttcct aagaacggtt   24420
ggaataataa aaatccagca aattttcaag atgtccaacg agacaaattg tactcttgac   24480
tttgaacagt cagttgagct ttttaaagag tataatttat ttataactgc attcttgttg   24540
ttcttaacca taatacttca gtatggctat gcaacaagag gtaagtttat ttatatactg   24600
aaaatgatag tgttatggtg cttttggccc cttaacattg cagtaggtgt aatttcatgt   24660
atatacccac caaacacagg aggtcttgtc gcagcgataa tacttacagt gtttgcgtgt   24720
ctgtcttttg taggttattg gatccagagt attagactct ttaagcggtg taggtcatgg   24780
tggtcattta acccagaatc taatgccgta ggttcaatac tcctaactaa tggtcaacaa   24840
tgtaattttg ctatagagag tgtgccaatg gtgctttctc caattataaa gaatggtgtt   24900
ctttattgtg agggtcagtg gcttgctaag tgtgaaccag accacttgcc taaagatata   24960 tttgttttgta caccggatag acgtaatatc taccgtatgg tgcagaaata tactggtgac   25020
caaagcggaa ataagaaaag gtttgctacg tttgtctatg caaagcagtc agtagacact   25080
ggcgagctag aaagtgtagc aacaggtgga agtagccttt acacataaat gtgtgtgtgt   25140
```

```
agagagtatt taaaattatt cttcaatagt gcctctattt taagagcgcg gaagagtatt    25200
tgttttgagg atattaatat aaatcctctt tgttttgtac tctctttaca agagttatta    25260
tttaagcaac agttttttcct ttcctttgtt tggaagaaag ttgttgttaa tggtgtagaa   25320
ttccaagtag aaaatggaaa agtccactac gaaggaaacc ccattttcta aaaaggttgt   25380
tgtaggttgt ggtcccatta taagaaggat taaatggatt aaaccaccta cactacttac   25440
ttgtaataag ggcgtttgga cttacaagcg cttaacaaat acagacgatg aaatggctga   25500
ctagttttgg aagagcagtt atttcttgtt ataaagccct actattaact cagttaagag   25560
tattagatag gttaatttta gatcacggac caaaacgcgt cttaacgtgt ggtaggcgag   25620 tgctttatc tcaattagat ctagtttata ggttggcata tacgcccacc caatcgctgg    25680
tatgaataat agtaaagata atccttttcg cggagcaata gcaagaaaag cgcgaattta   25740
tctgagagaa ggattagagt gtgtttactt tcttaacaaa gcaggacaag cagagtcttg   25800
tcccgcgtgt acctctctag tattccaggg gaaaacttgt gaggaacaca aagataataa   25860
taatcttttg tcatggcaag cggtaaggca actggaaaga cagatgcccc aactccagtc   25920
atcaaactag gaggaccaaa gccacctaaa gttggttctt ctggaaatgt atcttggttt   25980
caagcaataa aagccaagaa gttaaattca cctccgccta agtttgaagg tagcggtgtt   26040
cctgataatg aaaatctaaa accaagtcag cagcatggat attggagacg ccaagctagg   26100
tttaagccag gtaaaggtgg aagaaaacca gtcccagatg cttggtattt ttactatact   26160
ggaacaggac cagccgctaa cctgaattgg ggtgatagcc aagatggtat agtgtgggtt   26220
gctggtaagg gtgctgatac taaatttaga tctaatcagg gtactcgtga ctctgacaag   26280
tttgaccaat atccgctacg gttttcagac ggaggacctg atggtaattt ccgttgggat   26340
ttcattcctc tgaatcgtgg taggagtgga agatcaacag cggcttcatc agcagcatct   26400
agtagagcac cgtcgcgtga tggctcgcgt ggacgtagaa gcggagctga agatgatctt   26460
atagctcgtg cagcaaagat cattcaggat cagcagaaga agggttctcg cattactaaa   26520
gctaaggccg atgaaatggc tcatcgccgg tattgtaagc gtactatccc acctggttat   26580
aaggttgatc aagtatttgg tcccgtact aaatgtaagg agggaaattt tggtgatgac   26640
aagatgaatg aggagggtat taaggatggg cgcgttacag caatgctcaa cctagtccct   26700
agcagccatg cttgtctttt tggaagtaga gtgacgccca aacttcaacc agatgggctg   26760
cacttgagat ttgaatttac tactgtggtt tcacgtgatg atccgcagtt tgataattat   26820
gtgaaaattt gtgatcagtg tgtcgatggt gtagggacgc gtccaaaaga cgatgaaccg   26880
agaccaaagt cacgcccaaa ttcaagacct gctacaagaa caagttctcc agcgccaaga   26940
caacagcgtc aaaagaagga gaagaagtca agaagcagg atgatgaagt agataaggca   27000
ttgacctcag atgaggagag gaacaatgca cagctggaat tgatgatga acccaaggtg     27060 attaactggg gggagtcagc acttggagag aatgagttgt aaagctagat ttccaactta   27120
acatcatgga cgtgcgtatg ctgttttttcc ctactataga cttttttagca tattattttt   27180 tgctatttgt atggtttatt acaggtgaag attgtatgta tttgttgtac actcgtatgt   27240
tctatattat gttttctgta gttgttatta gtgttgttct tgttcttact ctactgttct   27300
cttttcttta ttttagagta tcaataagaa tcaaggaaga taggcatgta gtttgattac   27360
ctacatgtct atcgccaggg aaatgtctaa tctgtctact tagtagcctg gaaacgaacg   27420 gtagacccctt agatttttaat ttagtttaat ttttagttta gttaagtta gtttagagta   27480 ggtataaaga agccagtgcc gggccacgc ggagtacgat cgagggtaca gcactaggac   27540
```

```
gcccattagg ggaagagcta aattttagtt taagttaagt ttaataggct atgtatagtt    27600
aaaatttata ggctagtata gagttagagc aaaaaaaaaa aaaaaa                  27646
```

<210> SEQ ID NO 79
<211> LENGTH: 1162
<212> TYPE: PRT
<213> ORGANISM: Avian infectious bronchitis virus

<400> SEQUENCE: 79

```
Met Leu Val Thr Pro Leu Leu Val Thr Leu Leu Cys Ala Leu Cys
1               5                   10                  15

Ser Ala Val Leu Tyr Asp Ser Ser Tyr Val Tyr Tyr Gln Ser
            20                  25                  30

Ala Phe Arg Pro Pro Asp Gly Trp His Leu His Gly Ala Tyr Ala
            35                  40                  45

Val Val Asn Ile Ser Ser Glu Ser Asn Asn Ala Gly Ser Ser Gly
            50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala Tyr Cys Asn Phe Ser Asp Thr Thr Val Phe Val Thr
                100                 105                 110

His Cys Tyr Lys His Val Gly Cys Ser Leu Thr Gly Met Leu Gln Gln
                115                 120                 125

His Ser Ile Arg Val Ser Ala Met Lys Asn Gly Gln Leu Phe Tyr Asn
            130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Glu Val Arg Ala Leu Ala
            195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270

Thr Phe His Asn Glu Thr Gly Ala Asn Pro Asn Pro Ser Gly Val Gln
            275                 280                 285

Asn Ile Gln Thr Tyr Gln Thr Gln Thr Ala Gln Ser Gly Tyr Tyr Asn
        290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
            340                 345                 350
```

-continued

```
Pro Leu Gln Gly Gly Cys Lys Gln Ser Val Phe Ser Gly Arg Ala Thr
        355                 360                 365

Cys Cys Tyr Ala Tyr Ser Tyr Gly Gly Pro Leu Leu Cys Lys Gly Val
370                 375                 380

Tyr Ser Gly Glu Leu Asp His Asn Phe Glu Cys Gly Leu Leu Val Tyr
385                 390                 395                 400

Val Thr Lys Ser Gly Ser Arg Ile Gln Thr Ala Thr Glu Pro Pro
                405                 410                 415

Val Ile Thr Gln His Asn Tyr Asn Asn Ile Thr Leu Asn Thr Cys Val
            420                 425                 430

Asp Tyr Asn Ile Tyr Gly Gly Ile Gly Gln Gly Phe Ile Thr Asn Val
        435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Ser Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Ser Val Glu
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590

Thr Val Thr Asp Glu Tyr Ile Gln Thr Leu Met Asp Lys Val Gln Ile
        595                 600                 605

Asn Cys Leu Gln Tyr Ile Cys Gly Asn Ser Leu Glu Cys Arg Asn Leu
    610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
            660                 665                 670

Gly Glu Phe Asn Ile Ser Leu Phe Leu Thr Thr Pro Ser Ser Pro Arg
        675                 680                 685

Arg Arg Ser Phe Ile Glu Asp Leu Leu Phe Thr Ser Val Glu Ser Val
    690                 695                 700

Gly Leu Pro Thr Asp Asp Ala Tyr Lys Asn Cys Thr Ala Gly Pro Leu
705                 710                 715                 720

Gly Phe Leu Lys Asp Leu Val Cys Ala Arg Glu Tyr Asn Gly Leu Leu
                725                 730                 735

Val Leu Pro Pro Ile Ile Thr Ala Glu Met Gln Thr Leu Tyr Thr Ser
            740                 745                 750

Ser Leu Val Ala Ser Met Ala Phe Gly Gly Ile Thr Ala Ala Gly Ala
        755                 760                 765

Ile Pro Phe Ala Thr Gln Leu Gln Ala Arg Ile Asn His Leu Gly Ile
```

```
                770             775             780
Thr Gln Ser Leu Leu Lys Asn Gln Glu Lys Ile Ala Ala Ser Phe
785             790             795             800

Asn Lys Ala Ile Gly His Met Gln Glu Gly Phe Arg Ser Thr Ser Leu
            805             810             815

Ala Leu Gln Gln Ile Gln Asp Val Val Asn Lys Gln Ser Ala Ile Leu
            820             825             830

Thr Glu Thr Met Ala Ser Leu Asn Lys Asn Phe Gly Ala Ile Ser Ser
            835             840             845

Val Ile Gln Glu Ile Tyr Gln Gln Leu Asp Ala Ile Gln Ala Asn Ala
850             855             860

Gln Val Asp Arg Leu Ile Thr Gly Arg Leu Ser Ser Leu Ser Val Leu
865             870             875             880

Ala Ser Ala Lys Gln Ala Glu Tyr Ile Arg Val Ser Gln Arg Glu
                885             890             895

Leu Ala Thr Gln Lys Ile Asn Glu Cys Val Lys Ser Gln Ser Ile Arg
            900             905             910

Tyr Ser Phe Cys Gly Asn Gly Arg His Val Leu Thr Ile Pro Gln Asn
            915             920             925

Ala Pro Asn Gly Ile Val Phe Ile His Phe Ser Tyr Thr Pro Asp Ser
930             935             940

Phe Val Asn Val Thr Ala Ile Val Gly Phe Cys Val Lys Pro Ala Asn
945             950             955             960

Ala Ser Gln Tyr Ala Ile Val Pro Ala Asn Gly Arg Gly Ile Phe Ile
            965             970             975

Gln Val Asn Gly Ser Tyr Tyr Ile Thr Ala Arg Asp Met Tyr Met Pro
            980             985             990

Arg Ala Ile Thr Ala Gly Asp Ile Val Thr Leu Thr Ser Cys Gln Val
            995             1000            1005

Asn Tyr Val Ser Val Asn Lys Thr Val Ile Thr Thr Phe Val Asp
            1010            1015            1020

Asn Asp Asp Phe Asp Phe Asn Asp Glu Leu Ser Lys Trp Trp Asn
            1025            1030            1035

Asp Thr Lys His Glu Leu Pro Asp Phe Asp Lys Phe Asn Tyr Thr
            1040            1045            1050

Val Pro Ile Leu Asp Ile Asp Ser Glu Ile Asp Arg Ile Gln Gly
            1055            1060            1065

Val Ile Gln Gly Leu Asn Asp Ser Leu Ile Asp Leu Glu Lys Leu
            1070            1075            1080

Ser Ile Leu Lys Thr Tyr Ile Lys Trp Pro Trp Tyr Val Trp Leu
            1085            1090            1095

Ala Ile Ala Phe Ala Thr Ile Ile Phe Ile Leu Ile Leu Gly Trp
            1100            1105            1110

Val Phe Phe Met Thr Gly Cys Cys Gly Cys Cys Cys Gly Cys Phe
            1115            1120            1125

Gly Ile Met Pro Leu Met Ser Lys Cys Gly Lys Lys Ser Ser Tyr
            1130            1135            1140

Tyr Thr Thr Phe Asp Asn Asp Val Val Thr Glu Gln Tyr Arg Pro
            1145            1150            1155

Lys Lys Ser Val
            1160

<210> SEQ ID NO 80
```

```
<211> LENGTH: 409
<212> TYPE: PRT
<213> ORGANISM: Avian infectious bronchitis virus

<400> SEQUENCE: 80
```

| | | | | | | | | | | | | | | |
|---|---|---|---|---|---|---|---|---|---|---|---|---|---|---|
| Met | Ala | Ser | Gly | Lys | Ala | Thr | Gly | Lys | Thr | Asp | Ala | Pro | Thr | Pro | Val |
| 1 | | | | 5 | | | | | 10 | | | | | 15 | |
| Ile | Lys | Leu | Gly | Gly | Pro | Lys | Pro | Lys | Val | Gly | Ser | Ser | Gly | Asn |
| | | | 20 | | | | | 25 | | | | | 30 | |
| Val | Ser | Trp | Phe | Gln | Ala | Ile | Lys | Ala | Lys | Leu | Asn | Ser | Pro | Pro |
| | | | | 35 | | | | | 40 | | | | | 45 |
| Pro | Lys | Phe | Glu | Gly | Ser | Gly | Val | Pro | Asp | Asn | Glu | Asn | Leu | Lys | Pro |
| | 50 | | | | | 55 | | | | | 60 | | | | |
| Ser | Gln | Gln | His | Gly | Tyr | Trp | Arg | Arg | Gln | Ala | Arg | Phe | Lys | Pro | Gly |
| 65 | | | | | 70 | | | | | 75 | | | | | 80 |
| Lys | Gly | Gly | Arg | Lys | Pro | Val | Pro | Asp | Ala | Trp | Tyr | Phe | Tyr | Tyr | Thr |
| | | | | 85 | | | | | 90 | | | | | 95 | |
| Gly | Thr | Gly | Pro | Ala | Ala | Asn | Leu | Asn | Trp | Gly | Asp | Ser | Gln | Asp | Gly |
| | | | 100 | | | | | 105 | | | | | 110 | | |
| Ile | Val | Trp | Val | Ala | Gly | Lys | Gly | Ala | Asp | Thr | Lys | Phe | Arg | Ser | Asn |
| | | | 115 | | | | | 120 | | | | | 125 | | |
| Gln | Gly | Thr | Arg | Asp | Ser | Asp | Lys | Phe | Asp | Gln | Tyr | Pro | Leu | Arg | Phe |
| 130 | | | | | 135 | | | | | 140 | | | | | |
| Ser | Asp | Gly | Gly | Pro | Asp | Gly | Asn | Phe | Arg | Trp | Asp | Phe | Ile | Pro | Leu |
| 145 | | | | | 150 | | | | | 155 | | | | | 160 |
| Asn | Arg | Gly | Arg | Ser | Gly | Arg | Ser | Thr | Ala | Ala | Ser | Ser | Ala | Ala | Ser |
| | | | | 165 | | | | | 170 | | | | | 175 | |
| Ser | Arg | Ala | Pro | Ser | Arg | Glu | Val | Ser | Arg | Gly | Arg | Arg | Ser | Gly | Ser |
| | | | 180 | | | | | 185 | | | | | 190 | | |
| Glu | Asp | Asp | Leu | Ile | Ala | Arg | Ala | Ala | Arg | Ile | Ile | Gln | Asp | Gln | Gln |
| | | 195 | | | | | 200 | | | | | 205 | | | |
| Lys | Lys | Gly | Ser | Arg | Ile | Thr | Lys | Ala | Lys | Ala | Asp | Glu | Met | Ala | His |
| 210 | | | | | 215 | | | | | 220 | | | | | |
| Arg | Arg | Tyr | Cys | Lys | Arg | Thr | Ile | Pro | Pro | Asn | Tyr | Lys | Val | Asp | Gln |
| 225 | | | | | 230 | | | | | 235 | | | | | 240 |
| Val | Phe | Gly | Pro | Arg | Thr | Lys | Gly | Lys | Glu | Gly | Asn | Leu | Gly | Asp | Asp |
| | | | | 245 | | | | | 250 | | | | | 255 | |
| Lys | Met | Asn | Glu | Glu | Gly | Ile | Lys | Asp | Gly | Arg | Val | Thr | Ala | Met | Leu |
| | | | 260 | | | | | 265 | | | | | 270 | | |
| Asn | Leu | Val | Pro | Ser | Ser | His | Ala | Cys | Leu | Phe | Gly | Ser | Arg | Val | Thr |
| | | | 275 | | | | | 280 | | | | | 285 | | |
| Pro | Arg | Leu | Gln | Pro | Asp | Gly | Leu | His | Leu | Lys | Phe | Glu | Phe | Thr | Thr |
| | | 290 | | | | | 295 | | | | | 300 | | | |
| Val | Val | Pro | Arg | Asp | Asp | Pro | Gln | Phe | Asp | Asn | Tyr | Val | Lys | Ile | Cys |
| 305 | | | | | 310 | | | | | 315 | | | | | 320 |
| Asp | Gln | Cys | Val | Asp | Gly | Val | Gly | Thr | Arg | Pro | Lys | Asp | Asp | Glu | Pro |
| | | | | 325 | | | | | 330 | | | | | 335 | |
| Arg | Pro | Lys | Ser | Arg | Ser | Ser | Ser | Arg | Pro | Ala | Thr | Arg | Gly | Asn | Ser |
| | | | 340 | | | | | 345 | | | | | 350 | | |
| Pro | Ala | Pro | Arg | Gln | Gln | Arg | Pro | Lys | Lys | Glu | Lys | Lys | Pro | Lys | Lys |
| | | | 355 | | | | | 360 | | | | | 365 | | |
| Gln | Asp | Asp | Glu | Val | Asp | Lys | Ala | Leu | Thr | Ser | Asp | Glu | Glu | Arg | Asn |
| | 370 | | | | | 375 | | | | | 380 | | | | |
| Asn | Ala | Gln | Leu | Glu | Phe | Asp | Asp | Glu | Pro | Lys | Val | Ile | Asn | Trp | Gly |

```
                385                 390                 395                 400
Asp Ser Ala Leu Gly Glu Asn Glu Leu
                405

<210> SEQ ID NO 81
<211> LENGTH: 409
<212> TYPE: PRT
<213> ORGANISM: Avian infectious bronchitis virus

<400> SEQUENCE: 81

Met Ala Ser Gly Lys Ala Ala Gly Lys Thr Asp Ala Pro Thr Pro Val
1               5                   10                  15

Ile Lys Leu Gly Gly Pro Lys Pro Pro Lys Val Gly Ser Ser Gly Asn
            20                  25                  30

Val Ser Trp Phe Gln Ala Ile Lys Ala Lys Lys Leu Asn Ser Pro Pro
        35                  40                  45

Pro Lys Phe Glu Gly Ser Gly Val Pro Asp Asn Glu Asn Leu Lys Pro
    50                  55                  60

Ser Gln Gln His Gly Tyr Trp Arg Arg Gln Ala Arg Phe Lys Pro Gly
65                  70                  75                  80

Lys Gly Gly Arg Lys Pro Val Pro Asp Ala Trp Tyr Phe Tyr Tyr Thr
                85                  90                  95

Gly Thr Gly Pro Ala Ala Asn Leu Asn Trp Gly Asp Ser Gln Asp Gly
            100                 105                 110

Ile Val Trp Val Ala Gly Lys Gly Ala Asp Thr Lys Phe Arg Ser Asn
        115                 120                 125

Gln Gly Thr Arg Asp Ser Asp Lys Phe Asp Gln Tyr Pro Leu Arg Phe
    130                 135                 140

Ser Asp Gly Gly Pro Asp Gly Asn Phe Arg Trp Asp Phe Ile Pro Leu
145                 150                 155                 160

Asn Arg Gly Arg Ser Gly Arg Ser Thr Ala Ala Ser Ser Ala Ala Ser
                165                 170                 175

Ser Arg Ala Pro Ser Arg Glu Val Ser Arg Gly Arg Arg Ser Gly Ser
            180                 185                 190

Glu Asp Asp Leu Ile Ala Arg Ala Ala Arg Ile Ile Gln Asp Gln Gln
        195                 200                 205

Lys Lys Gly Ser Arg Ile Thr Lys Ala Lys Ala Asp Glu Met Ala His
    210                 215                 220

Arg Arg Tyr Cys Lys Arg Thr Ile Pro Pro Asn Tyr Lys Val Asp Gln
225                 230                 235                 240

Val Phe Gly Pro Arg Thr Lys Gly Lys Glu Gly Asn Phe Gly Asp Asp
                245                 250                 255

Lys Met Asn Glu Glu Gly Ile Lys Asp Gly Arg Val Thr Ala Met Leu
            260                 265                 270

Asn Leu Val Pro Ser Ser His Ala Cys Leu Phe Gly Ser Arg Val Thr
        275                 280                 285

Pro Arg Leu Gln Pro Asp Gly Leu His Leu Lys Phe Glu Phe Thr Thr
    290                 295                 300

Val Val Pro Arg Asp Asp Pro Gln Phe Asp Asn Tyr Val Lys Ile Cys
305                 310                 315                 320

Asp Gln Cys Val Asp Gly Val Gly Thr Arg Pro Lys Asp Asp Glu Pro
                325                 330                 335

Arg Pro Lys Ser Arg Ser Ser Ser Arg Pro Ala Thr Arg Gly Asn Ser
            340                 345                 350
```

```
Pro Ala Pro Arg Gln Gln Arg Pro Lys Lys Glu Lys Lys Pro Lys Lys
            355                 360                 365

Gln Asp Asp Glu Val Asp Lys Ala Leu Thr Ser Asp Glu Glu Arg Asn
    370                 375                 380

Asn Ala Gln Leu Glu Phe Asp Asp Glu Pro Lys Val Ile Asn Trp Gly
385                 390                 395                 400

Asp Ser Ala Leu Gly Glu Asn Glu Leu
                405

<210> SEQ ID NO 82
<211> LENGTH: 109
<212> TYPE: PRT
<213> ORGANISM: Avian infectious bronchitis virus

<400> SEQUENCE: 82

Met Met Asn Leu Leu Asn Lys Ser Leu Glu Glu Asn Gly Ser Phe Leu
1               5                   10                  15

Thr Ala Leu Tyr Ile Phe Val Gly Phe Leu Ala Phe Tyr Leu Leu Gly
            20                  25                  30

Arg Ala Leu Gln Ala Phe Val Gln Ala Ala Asp Ala Cys Cys Leu Phe
        35                  40                  45

Trp Tyr Thr Trp Leu Val Ile Pro Gly Val Lys Gly Thr Ala Phe Val
    50                  55                  60

Tyr Lys Tyr Thr Tyr Gly Arg Lys Leu Asn Asn Ser Glu Leu Glu Ala
65                  70                  75                  80

Val Val Val Asn Glu Phe Pro Lys Asn Gly Trp Asn Asn Lys Asn Pro
                85                  90                  95

Ala Asn Phe Gln Asp Val Gln Arg Asn Lys Leu Tyr Ser
            100                 105

<210> SEQ ID NO 83
<211> LENGTH: 225
<212> TYPE: PRT
<213> ORGANISM: Avian infectious bronchitis virus

<400> SEQUENCE: 83

Met Ser Asn Glu Thr Asn Cys Thr Leu Asp Phe Glu Gln Ser Val Glu
1               5                   10                  15

Leu Phe Lys Glu Tyr Asn Leu Phe Ile Thr Ala Phe Leu Leu Phe Leu
            20                  25                  30

Thr Ile Ile Leu Gln Tyr Gly Tyr Ala Thr Arg Ser Lys Phe Ile Tyr
        35                  40                  45

Ile Leu Lys Met Ile Val Leu Trp Cys Phe Trp Pro Leu Asn Ile Ala
    50                  55                  60

Val Gly Val Ile Ser Cys Ile Tyr Pro Pro Asn Thr Gly Gly Leu Val
65                  70                  75                  80

Ala Ala Ile Ile Leu Thr Val Phe Ala Cys Leu Ser Phe Val Gly Tyr
                85                  90                  95

Trp Ile Gln Ser Ile Arg Leu Phe Lys Arg Cys Arg Ser Trp Trp Ser
            100                 105                 110

Phe Asn Pro Glu Ser Asn Ala Val Gly Ser Ile Leu Leu Thr Asn Gly
        115                 120                 125

Gln Gln Cys Asn Phe Ala Ile Glu Ser Val Pro Met Val Leu Ser Pro
    130                 135                 140

Ile Ile Lys Asn Gly Val Leu Tyr Cys Glu Gly Gln Trp Leu Ala Lys
145                 150                 155                 160
```

-continued

```
Cys Glu Pro Asp His Leu Pro Lys Asp Ile Phe Val Cys Thr Pro Asp
                165                 170                 175

Arg Arg Asn Ile Tyr Arg Met Val Gln Lys Tyr Thr Gly Asp Gln Ser
            180                 185                 190

Gly Asn Lys Lys Arg Phe Ala Thr Phe Val Tyr Ala Lys Gln Ser Val
        195                 200                 205

Asp Thr Gly Glu Leu Glu Ser Val Ala Thr Gly Gly Ser Ser Leu Tyr
    210                 215                 220

Thr
225

<210> SEQ ID NO 84
<211> LENGTH: 32
<212> TYPE: DNA
<213> ORGANISM: Artificial Sequence
<220> FEATURE:
<223> OTHER INFORMATION: Primer

<400> SEQUENCE: 84
ctttggatca ttaaacagac tttttaggtc tg                                32

<210> SEQ ID NO 85
<211> LENGTH: 29
<212> TYPE: DNA
<213> ORGANISM: Artificial Sequence
<220> FEATURE:
<223> OTHER INFORMATION: Primer

<400> SEQUENCE: 85
gtctgtttaa tgatccaaag tcccactag                                    29
```

H52 IBV VACCINE WITH HETEROLOGOUS SPIKE PROTEIN

CROSS-REFERENCE TO OTHER APPLICATIONS

This application claims the benefit of E.P. Patent Application No. 18203637.6, filed Oct. 31, 2018, the entire contents of which are hereby incorporated by reference herein.

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Avian coronavirus infectious bronchitis virus (IBV) is the prototype gammacoronavirus of the family Coronaviridae, order Nidovirales. Infectious bronchitis virus principally infects the upper respiratory epithelium of chickens, causing a respiratory disease, commonly complicated by sec ondary bacterial pathogens (Cook et al. 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-thirds of the viral genome comprise a large coding region (also designated as gene 1), divided into two open reading frames 1a and 1b, which encode for 15 nonstructural proteins involved in RNA replication, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms the ribonucleoprotein core along with the viral RNA. The coronavirus spike protein determines the host species tropism (Kuo et al. 2000. J. Virol. 74:1393-1406). It is a dimeric or trimeric transmembrane protein, which is proteolytically cleaved into two subunits, S1 and S2. The heavily glycosylated S1 domain forms the 'head' of the spike protein and contains the receptor binding domain that interacts with 2,3-linked sialic acids on the host cell surface (Promkuntod et al. 2014. Virology. 448:26-32). The S2 domain contains the remaining part of the ectodomain (the 'stalk'), the transmembrane domain and the endodomain located in the cytoplasm.

The to date most widely used live-attenuated IBV vaccine strains were developed in the 1960s in the Netherlands, by serial passaging of a Massachusetts-like IBV strain (Bijlenga et al. 2004; Avian Pathol. 33:550-557). However, since the 1970s new IBV serotypes emerged against which the traditional Massachusetts-like vaccines did not protect sufficiently (Cook et al. 2012. Avian Pathol. 41:239-250). Therefore, there is a need for new and highly efficacious IBV vaccines against other IBV serotypes.

IBV Beaudette (Geilhausen et al. 1973. Arch Gesamte Virusforsch.: 40 (3) (1973), pp. 285-290) and H120 (G. Bijlenga et al. 2004. Avian Pathol.: 33 (6); pp. 550-557) are attenuated IBVs. However, attenuation may result in a loss of immunogenicity.

Further, recombinant IBVs have been generated. Zhou et al. 2016 (Arch Virol.; 161:3179-3187) disclose a H120 (Massachusetts genotype) IBV with Beaudette (Massachusetts genotype) spike protein. Hodgson et al. 2004 (J Virol 78: 13804-13811) disclose a Beaudette (Massachusetts genotype) IBV with M41 (Massachusetts genotype) Spike protein. Furthermore, Armesto et al. 2011 (PLoS One: 6(8):e24352) disclose IBV Beaudette (Massachusetts genotype) with a heterologous spike protein from 4/91 (4/91 genotype).

However, the recombinant IBVs disclosed in Zhou et al. 2016 and Hodgson et al. 2004 cannot be regarded as IBVs with a heterologous spike protein as both, the IBV and the inserted spike is from the same genotype/serotype (Massachusetts). Further, all mentioned vaccines are based on a Beaudette based backbone or have a spike protein from Beaudette.

Further, no Beaudette based vaccines and no such recombinant vaccines (with heterologous spike proteins) are commercially available although Beaudette was already described many decades ago and recombinant approaches using Beaudette are known for more than one decade, respectively. Recombinant IBVs based on Beaudette are not suitable as vaccines. Wei et al 2014 (Apl Microbiol Biotechnol 98) discloses a Beaudette IBV having the S1 subunit of H120.

Ellis et al 2018 (J. Virol. 92(23)), Hodgson et al (J. Virol. 78(24)) and Armesto et al. 2011 (PLoS One: 6(8):e24352) all disclose Beaudette IBV with a M41 or 4/91 spike protein. However, Ellis et al 2018 (J. Virol. 92(23)) describe that recombinant Beaudette with chimeric spikes with heterologous S1 subunits from M41 or QX in combination with Beaudette spike S2 subunit do not confer sufficient protection against S1 homologous challenges ("A single vaccination of specific-pathogen-free chickens with rIBV expressing S1 of virulent strains M41 or QX, BeauR-M41 (S1) and BeauR-QX (S1), gave incomplete protection against homologous challenge, based on ciliary activity and clinical signs"; abstract). Further, Ellis et al 2018 (J. Virol. 92(23)) describe that the full length S gene (S1 and S2 from M41) only gave partial protection against challenge with an IBV of homologous serotype (page 12), suggesting that the IBV Beaudette strain is not suitable as backbone for recombinant IBV vaccines. Hodgson et al (J. Virol. 78(24)) further discloses that the Baudette strain "is also considered to be poorly immunogenic" and consequently, "it has never been used as a vaccinal strain" (page 13802, left column, second paragraph). Therefore, there is a need for generating novel and highly efficacious IBV vaccines and recombinant IBV vaccines, respectively. Further, there is a need for highly efficacious IBV vaccine vectors.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an H52 IBV (infectious bronchitis virus) encoding for a heterologous IBV S (spike) protein or fragment thereof.

The term "H52 IBV" is well known to the person skilled in the art. The term "IBV" refers to an infectious bronchitis virus. The term "H52" defines the specific IBV strain. The H52 strain is well known to the person skilled in the art and belongs to the Massachusetts genotype. IBV strains are typically differentiated by the coding sequence of the S1 subunit of the spike protein (Valastro et al. 2016. Infect Genet Evol. 39:349-364) but can also be differentiated by their complete nucleotide sequence or the sequences of specific proteins such as the spike protein, Nucleocapsid protein, envelope (E) protein or membrane (M) glycoprotein. Because the spike protein determines host tropism and antigenicity of IBV, the IBV genotypes are classified by the coding sequence of the subunit 1 of the spike proteins. Alternatively, IBV strains can be differentiated by their serotype. Serotype classification involves treatment of the virus with neutralizing antibodies.

Further, H52 can be differentiated from H120 by higher pathogenicity upon application in young chickens.

It is in the general knowledge of a person skilled in the art where to obtain H52 IBV. H52 IBV strains can be commercially purchased such as exemplary Nobilis IB H52 (MSD Animal Health), AviPro IB H52 (Lohmann Animal Health GmbH & Co. KG), Bronchovac (Ceva) and the alike. Further, McDonald et al. 1980 (Avain Pathology 9:245-259) disclose that H52 IBV can be obtained by Central Veterinary Laboratory Rotterdam, Kusters (J. gen Virol 68:343-352) disclose that H52 IBV can be obtained by the Poultry Health Institute Dorn in the Netherlands (which is now GD Animal Health) and Chen et al. 2007 (Avian Pathology 36(4):269-274) disclose that H52 IBV can be obtained by the China Institute of Veterinary Drug Control. Furthermore, H52 IBV is used as vaccine strain for decades (Bijlenga et al. 2004, Avian Pathology 33 (6): 550-557) and, therefore, can be isolated from the field. The methods to isolate H52 IBV strains and to characterize the H52 IBV strains are well known to the person skilled in the art. Exemplary, H52 IBV strains can be characterized as described in Zwaagstra et al. 1992 (J. Clin. Microbiol. 30 (1): 79-84), Handberg et al. 1999 (Avian Pathology 28: 327-335) or Callison et al. 2006 (Journal of Virological Methods 138: 60-65). Zwaagstra et al. 1992 and Handberg et al. 1999 for example disclose Massachusetts specific primers (for the S and N protein, respectively) for RT-PCR and sequencing and reference sequences for comparison. Further, H52 IBVs have been sequenced and the genomic sequences are available such as EU817497. Thus, the virus genome can be generated by synthesizing its sequence and generated upon the application of reverse genetic systems.

The term "spike" refers to a specific protein of the IBV that is well known by the person skilled in the art. The spike protein is the major inducer of antibodies and protective immune response. Further, the spike (S) protein facilitates cell entry of IBV by binding cellular receptors of the host cell and also by mediating virus-cell membrane fusion with the host cell. In addition, it determines the tissue and cell tropism of the virus strain.

The term "heterologous S (spike)" means that the spike protein or fragment thereof that has been introduced into the H52 IBV is from a different genotype or serotype than the H52 IBV. Because the H52 is Massachusetts genotype and serotype, the heterologous spike is of a non-Massachusetts genotype or serotype.

The term "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

Further, the present invention also provides an immunogenic composition comprising an H52 IBV (infectious bronchitis virus) encoding for a heterologous S (spike) protein or fragment thereof.

Furthermore, the present invention also provides an immunogenic composition comprising an IBV (infectious bronchitis virus) as described herein. Thus, provided is an immunogenic composition comprising an H52 IBV (infectious bronchitis virus) encoding for a heterologous IBV S (spike) protein or fragment thereof.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutical response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

H52-IBV—Definition by Protein Encoding Sequences

In another specific aspect of the IBV or the immunogenic composition according to the present invention the H52 IBV has a nucleotide sequence as shown for EU817497 (SEQ ID NO: 78) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

The term "nucleic acid" or "nucleic acid sequence" or "nucleotide sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificially modified ones such as biotinylated polynucleotides. Further, the terms "nucleic acid" and "polynucleotide" are interchangeable and refer to any nucleic acid. The terms "nucleic acid" and "polynucleotide" also specifically include nucleic acids composed of bases other than the five biologically occurring bases (adenine, guanine, thymine, cytosine and uracil).

The term "RNA" refers to any ribonucleic acid. The term encompasses single as well as double stranded RNAs. The RNA of the present invention encompasses isolated RNA (i.e. isolated from its natural context) and genetically modified forms. Moreover, comprised are also chemically modified RNAs including naturally occurring modified RNAs such as methylated RNA or artificially modified ones such as biotinylated RNA. The terms "RNA" also specifically include RNA composed of bases other than the four biologically occurring nucleotides/bases (adenine, guanine, cytosine and uracil).

In another specific aspect of the IBV or the immunogenic composition according to the present invention the H52 IBV strain has a spike (S) protein having an amino acid sequence as shown for AF352315 (SEQ ID NO: 79) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

It has to be understood that the spike protein or nucleic acid sequence can be used to determine whether any IBV strain is of H52 origin. However, because the H52 IBV is used as a backbone and the H52 spike protein or nucleic acid sequence is replaced by a heterologous spike or fragment thereof, the final IBV with the heterologous spike does not comprise any or only remaining parts of the H52 spike.

In another specific aspect of the IBV or the immunogenic composition according to the present invention the H52 IBV strain has a spike (S) protein having an amino acid sequence as shown SEQ ID NO:1 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the H52 IBV has a nucleocapsid (N) protein having an amino acid sequence as shown for AY044185 (SEQ ID NO:80) or a sequence having at least 95%, 96%, 97%, 98%, 99%, 99.2%, 99.5%, 99.6%, 99.7%, 99.8%, 99.9%, 99.95%, 99.98% or 99.99% sequence identity to at least one of the above mentioned sequences.

In another specific aspect of the IBV or the immunogenic composition according to the present invention the H52 IBV has a nucleocapsid (N) protein having an amino acid sequence as shown for AF352310 (SEQ ID NO: 81) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according o the present invention the H52 IBV has a nucleocapsid (N) protein having an amino acid sequence as shown SEQ ID NO:2 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the H52 IBV has an envelope (E) protein having an amino acid sequence as shown for AF317210 (SEQ ID NO: 82) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the H52 IBV has an envelope (E) protein having an amino acid sequence as shown in SEQ ID NO:3 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the H52 IBV has a membrane glycoprotein (M) protein having an amino acid sequence as shown for AF286185 (SEQ ID NO: 83) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the IBV or the immunogenic composition according to the present invention the H52 IBV has a membrane glycoprotein (M) protein having an amino acid sequence as shown in SEQ ID NO:4 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are of the same length.

A sequence comparison may be carried out over the entire lengths of the two sequences being compared or over fragments of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package, using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms.

The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-

3402. When utilizing BLAST and Gapped BLAST programs, the default parameters of the respective programs (e.g., BLASTP and BLASTN) can be used. See the internet homepage of the National Center for Biotechnology Information.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. In this context, "X" is any integer selected from 1 to 85 so that "SEQ ID NO: X" represents any of the SEQ ID NOs mentioned herein.

Heterologous S Protein
IBV Strains

IBV strains can be classified by serotype and genotype. Serotype classification involves treatment of the virus with neutralizing antibodies, whereas genotype classification generally involves examining the sequence of the S1 (spike) protein. However, the different IBV strains are well known to the person skilled in the art. Infectious bronchitis virus was first discovered in the United States in the 1930s. The first IBV serotype identified was Massachusetts, but in the United States several serotypes, including Arkansas and Delaware have been identified in addition to the originally identified Massachusetts type.

The IBV strain Beaudette is of Massachusetts type and was derived following at least 150 passages in chick embryos. The IBV strain Beaudette was originally isolated by Beaudette and Hudson (J. Am. Vet. Med. A. 90, 51-60, 1937) and passaged in chicken embryos. Other Massachusetts type IBV strains besides Beaudette are H120, H52, and M41. The H120 strain was passaged 120 times.

IBV QX is described as virulent field isolate of IBV which was originally isolated in China. However, the virus has spread towards Europe and has been identified in parts of Western Europe, predominantly in the Netherlands, but also in Germany, France, Belgium, Denmark and in the UK. In addition, the QX genotype or serotype has been described in several countries in Asia and Africa.

IBV 4/91 which is commonly also called 793B was first reported in the UK in the early nineties and is now distributed to many parts of the world. CR88 is an attenuated strain belonging to this genotype and commercially available as a vaccine.

The strains designated "Italian-02" or "Italy-02" was isolated in the late 1990's in Italy. The sequence analysis of one of these isolates was published in 2002 (NCBI-BLAST, number AJ457137). However, studies have shown that this Italian-02 strain is widespread in Europe and that, apart from IBV variant strain 4/91 it has become one of the most predominant genotypes in the UK, Spain, France and The Netherlands.

Since 1996 a new Infectious Bronchitis virus (IBV) genotype, referred to as Q1, has circulated in China and was reported for the first time in Italy in 2011. Q1 is associated with an increase of mortality, kidney lesions and proventriculitis.

Furthermore, strains D274, B1648/D8880, D1466, V1397 and Arkansas have been identified in Europe as well.

It is in the general knowledge of a person skilled in the art where to obtain any IBV strains. IBV strains can be be commercially purchased, obtained from scientific Institutes or the genomes can be synthetical synthesized as complementary DNA as IBV strains have been sequenced and the sequences have been published and are, thus, available. Furthermore, IBV strains can be isolated from the field. The methods to isolate IBV strains and to characterize the IBV strains are well known to the person skilled in the art. Valter Leonardo de Quadros 2011 (Dissertation, Das Infektiöse Bronchitis Virus (IBV): Molekularbiologische Untersuchungen zur Diagnostik and zum Vorkommen sowie zur Pathogenität des Genotyps IBV QX in spezifisch pathogenfreien (SPF) Broilern, Freie Universität Berlin), Worthington et al. 2009 (Avian Pathology 37(3), 247-257), Liu et al. 2009 (Virus Genes 38: 56-65), Dolz et al. 2006 (Avian Pathology 35 (2): 77-85), Farsang et al. 2002 (Avian Pathology 31: 229-236) and Feng et al. 2014 (Virus Genes 49: 292-303) describe how to isolate and differentiate different IBV strains.

In another specific aspect of the IBV or the immunogenic composition according to the present invention the heterologous spike is of a non-Massachusetts genotype or serotype.

In another specific aspect of the IBV or the immunogenic composition according to the present invention the heterologous S protein or fragment thereof is from an IBV with a genotype or serotype selected from a list consisting of: Arkansas (such as Arkansas 99), Brazil (such as BR-1, BR-2, 23/2013, IBV/Brazil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV or the immunogenic composition according to the present invention the heterologous S protein or fragment thereof is from an IBV selected from a list of genotypes or serotypes consisting of 4/91, QX, Q1, Italy 02, Arkansas, Connecticut, Georgia, LDT3, PL84084, Variant 2 or Brazil.

In another specific aspect of the IBV or the immunogenic composition according to the present invention the heterologous S protein or fragment thereof is from an IBV selected from a list of genotypes or serotypes consisting of 4/91, QX, Q1, Arkansas, Variant 2 and Brazil.

In another specific aspect of the IBV or the immunogenic composition according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated, IB4-91 and CR88.

In another specific aspect of the IBV or the immunogenic composition according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV or the immunogenic composition according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV or the immunogenic composition according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV or the immunogenic composition according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/24/10_EG, TR8 and IB VAR2-06.

In another specific aspect of the IBV or the immunogenic composition according to the present invention the Brazil strain is selected from a list consisting of: BR-1, BR-2, 23/2013 and IBV/Brazil/351/1984.

In another specific aspect of the IBV or the immunogenic composition according to the present invention the heterologous S protein or fragment thereof is from 4/91 genotype or serotype.

In another specific aspect of the IBV or the immunogenic composition according to the present invention the heterologous S protein or fragment thereof is from genotype or serotype 4/91 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:5 or 6.

In another specific aspect of the IBV or the immunogenic composition according to the present invention the heterologous S protein or fragment thereof is from genotype or serotype QX having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:7 or 8.

In another specific aspect of the IBV or the immunogenic composition according to the present invention the heterologous S protein or fragment thereof is from genotype or serotype Q1 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:9 or 10.

In another specific aspect of the IBV or the immunogenic composition according to the present invention the heterologous S protein or fragment thereof is from genotype or serotype Arkansas having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:11 or 12.

In another specific aspect of the IBV or the immunogenic composition according to the present invention the heterologous S protein or fragment thereof is from genotype or serotype Variant 2 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:13 or 14.

In another specific aspect of the IBV or the immunogenic composition according to the present invention the heterologous S protein or fragment thereof is from genotype or serotype Brazil having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:15 or 16.

In another specific aspect of the IBV or the immunogenic composition according to the present invention the heterologous S protein or fragment thereof is selected from a list consisting of SEQ ID NO: 5, 6, 7, 8, 9, 10, 11,12, 13, 14, 15 or 16.

In another specific aspect of the IBV or the immunogenic composition according to the present invention the heterologous S protein is the full length spike protein.

The present experimental data show that fragments of the spike protein sequence can be used such as the ectodomain of the spike protein. However, full length spike protein sequences can be used as well.

In another specific aspect of the IBV or the immunogenic composition according to the present invention the fragment of the heterologous S (spike) protein has a length of at least 500, 750, 1000 or 1077 amino acids.

In another specific aspect of the IBV or the immunogenic composition according to the present invention the fragment of the heterologous S (spike) protein has a length of at least 500, 750, 1000 or 1077 amino acids from the N-Terminus.

The term "N-terminus" is well known to the person skilled in the art. The N-terminus is also termed amino-terminus, NH2-terminus, N-terminal end or amine-terminus. When the protein is translated from messenger RNA, it is created from N-terminus to C-terminus. Thus, the N-terminus is the start of an amino acid chain (protein or polypeptide) comprising said amine group (—NH2).

In another specific aspect of the IBV or the immunogenic composition according to the present invention the fragment of the heterologous S (spike) protein has a length of at least 1000 amino acids.

In another specific aspect of the IBV or the immunogenic composition according to the present invention the fragment of the heterologous S (spike) protein is the ectodomain of the spike protein.

The term "ectodomain" is well known to a person skilled in the art. The spike protein comprises different functional parts, the signal sequence, the ectodomain, the transmembrane domain and the endodomain (from N-terminus to C-terminus). Thus, after cleavage of the signal sequence, the N-terminus of the spike protein starts with the ectodooamain. The IBV spike ectodoamins has a length of about 1077 amino acids and differs by a a few amino acids in length dependent on the IBV strain.

In another specific aspect of the IBV or the immunogenic composition according to the present invention the heterologous S (spike) protein or fragment thereof replaces the homologous S protein or fragment thereof.

In another specific aspect of the IBV or the immunogenic composition according to the present invention the heterologous S (spike) protein or fragment thereof replaces the natural occurring S protein or fragment thereof.

In another specific aspect of the IBV or the immunogenic composition according to the present invention the heterologous S (spike) protein or fragment thereof replaces the S protein or fragment thereof in H52 IBV.

In another specific aspect of the IBV or the immunogenic composition according to the present invention the IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated, IBV strain is one that is suitable for incorporation into an immunogenic composition comprising a modified live IBV.

In another specific aspect of the IBV or the immunogenic composition according to the present invention the IBV is inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as polysaccharides, peptides, proteins, or the like, or a combination thereof.

In another specific aspect of the IBV or the immunogenic composition according to the present invention the IBV is genetically engineered.

The term "genetically engineered" refers to an IBV which has been mutated by using "reverse genetics" approaches. Preferably, the IBV according to the present invention has been genetically engineered. The reverse genetics technique involves the preparation of synthetic recombinant viral RNAs. However, "reverse genetics" techniques are well known to the person skilled in the art.

In another specific aspect of the IBV or the immunogenic composition according to the present invention the IBV is a recombinant IBV.

The term "recombinant" as used herein relates to a RNA genome (or RNA sequence, cDNA sequence or protein) having any modifications that do not naturally occur to the corresponding RNA genome (or RNA sequence, cDNA sequence or protein). For instance, a RNA genome (or RNA sequence, cDNA sequence or protein) is considered "recombinant" if it contains an insertion, deletion, inversion, relocation or a point mutation introduced artificially, e.g., by human intervention. Therefore, the RNA genomic sequence (or RNA sequence, cDNA sequence or protein) is not associated with all or a portion of the sequences (or RNA sequence, cDNA sequence or protein) with which it is associated in nature. The term "recombinant" as used with respect to a virus, means a virus produced by artificial manipulation of the viral genome. The term "recombinant virus" encompasses genetically modified viruses.

In another specific aspect of the IBV or the immunogenic composition according to the present invention the IBV is chimeric.

The term "chimeric" refers to an IBV comprising one or more nucleotide sequences from another coronavirus, preferably from another IBV strain. Exemplary, an IBV H52 encoding for a heterologous S (spike) protein or fragment thereof is a chimeric IBV.

In another specific aspect of the immunogenic composition according to the present invention the immunogenic composition is a vaccine. The term "vaccine" already has been described elsewhere herein. However, in case where the host displays a protective immunological response such that resistance to new infection will be enhanced and/or the clinical severity of the disease reduced, the immunogenic composition is described as a "vaccine."

In another specific aspect of the immunogenic composition according to the present invention the immunogenic composition comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In another specific aspect of the immunogenic composition according to the present invention the pharmaceutically acceptable carrier is phosphate buffered saline.

Preferably, the immunogenic composition further comprises sucrose gelatin stabilizer.

Preferably, the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di- (caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among them, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide, or naturally occurring or recombinant cytokines or analogs thereof or stimulants of endogenous cytokine release, among many others It is expected that an adjuvant can be added in an amount of about 100 μg to about 10 mg per dose, preferably in an amount of about 100 μg to about 10 mg per dose, more preferably in an amount of about 500 μg to about 5 mg per dose, even more preferably in an amount of about 750 μg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition according to the present invention the immunogenic composition is effective in the treatment and/or prophylaxis of clinical signs caused by IBV in a subject of need. The terms "treatment and/or prophylaxis", "clinical signs" and "of need" have been defined elsewhere.

In another specific aspect of the immunogenic composition according to the present invention the immunogenic composition protects against a challenge with an IBV strain of the genotype or serotype of the heterologous spike protein.

In another specific aspect of the immunogenic composition according to the present invention the immunogenic composition protects against a challenge with strains of 4/91, QX, Q1, Arkansas, Variant 2 or Brazil genotype.

In another specific aspect of the immunogenic composition according to the present invention the immunogenic composition protects against a challenge with strains of 4/91 genotype.

In another specific aspect of the immunogenic composition according to the present invention said immunogenic composition is formulated for a single-dose administration.

The volume for a single-dose has been defined elsewhere herein.

It has furthermore been shown that one dose of the immunogenic composition of the present invention is effective after the administration of such single dose of such immunogenic composition.

In another specific aspect of the immunogenic composition according to the present invention the immunogenic composition is administered subcutaneously, intramuscularly, oral, in ovo, via spray, via drinking water or by eye drop.

In another specific aspect of the immunogenic composition according to the present invention the immunogenic composition comprises 1 to 10 $\log_{10}$ EID50 per dose of the IBV.

In another specific aspect of the immunogenic composition according to the present invention the immunogenic composition comprises 2 to 5 $\log_{10}$ EID50 per dose of the IBV.

In another specific aspect of the immunogenic composition according to the present invention the immunogenic composition comprises 2 to 4 $\log_{10}$ EID50 per dose of the IBV.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for human administration.

Thus, the present invention provides a kit comprising the IBV or the immunogenic composition as described herein.

In one specific aspect of the kit according to the present invention the kit further comprises an instruction letter for the treatment and/or prophylaxis of diseases of avians.

In one specific aspect of the kit according to the present invention the kit further comprises an instruction letter for the treatment and/or prophylaxis of diseases of poultry.

In one specific aspect of the kit according to the present invention the kit further comprises an instruction letter for the treatment and/or prophylaxis of IB (infectious bronchitis).

Method of Treatments

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular IBV infection in a flock or in the reduction in the severity of clinical signs caused by or associated with the particular IBV infection.

Further, the immunization of a subject in need with the immunogenic compositions as provided herewith, results in preventing infection of a subject by IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized. However, the term requires that a significant portion of subjects of a flock are effectively immunized.

Preferably, a flock of subjects is envisaged in this context which normally, i.e. without immunization, would develop clinical signs normally caused by or associated with a IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular IBV.

Further, the present invention provides a method of treating or preventing clinical signs caused by IBV in a subject of need, the method comprising administering to the subject a therapeutically effective amount of an immunogenic composition as described herein.

The term "treating or preventing" refers to the lessening of the incidence of the particular IBV infection in a flock or the reduction in the severity of clinical signs caused by or associated with the particular IBV infection. Thus, the term "treating or preventing" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. The clinical signs of infection depend on the pathogen selected. Examples for such clinical signs include but are not limited to respiratory distress, nephritis, salphingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

The term "reducing" or or "reduced" or "reduction" or lower" are used interchangeable in this application. The term "reduction" means, that the clinical sign is reduced by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, even more preferably by at least 90%, still more preferably by at least 95% most preferably by 100% in comparison to subjects that are not treated (not immunized) but subsequently infected by the particular IBV.

Further, the present invention provides a method of reducing the ciliostasis in a subject of need, in comparison to a subject of a non-immunized control group of the same species, the method comprising administering to the subject a therapeutically effective amount of an immunogenic composition as described herein.

As shown in the Examples, the immunogenic composition as provided herein has been proven to be efficacious in reducing ciliostasis.

The term "ciliostasis" refers to a reduced movement of the cilia in the trachea. Thus, ciliostasis may be determined by examining the inner lining of the tracheal rings for the movement of the cilia. It is in the general knowledge of a person skilled in the art how to determine the movement of the cilia in the trachea.

Preferably, the movement of the cilia is not reduced from day 10 after challenge or infection, more preferably from day 5 after challenge or infection, more preferably from day 4 after challenge or infection, more preferably from day 3 after challenge or infection and most preferably from day 1 or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the ciliostasis.

In one aspect of the present invention said subject is avian.

The term "avian" is well known to the person skilled in the art. The term "avian" encompasses all birds including poultry.

In one aspect of the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred as breeders.

In one aspect of the present invention said subject is selected from the list consisting of chicken, turkey, quail, or pheasant.

In one aspect of the present invention said subject is chicken.

In one aspect of the present invention the immunogenic composition is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 µl per dose at any age. Preferably, the single-dose for eye drop vaccines has a total volume between about 5 µl and 70 µl and more preferably between about 20 µl and 50 µl with a single 20 µl, 25 µl, 30 µl, 35 µl, 40 µl, 45 µl or 50 µl dose being preferred. Most preferred, the single-dose for eye drop vaccines has a total volume between between about 30 µl and 50 µl with a single 30 µl, 35 µl, 40 µl, 45 µl or 50 µl dose being preferred.

Spray vaccines may contain the dose in a volume of 25 to 1000 µl for day-old poultry. Preferably, the single-dose for spray vaccines has a total volume between about 50 µl and 5000 µl, more preferably between about 75 µl and 2000 µl, more preferably between about 100 µl and 1000 µl, even more preferably between about 200 µl and 900 µl, even more preferably between about 300 µl and 800 µl and even more preferably between about 400 µl and 700 µl with a single 400 µl, 425 µl, 450 µl, 475 µl, 500 µl, 525 µl, 550 µl, 575 µl, 600 µl, 625 µl, 650 µl, 675 µl or 700 µl dose being preferred. Most preferred the single-dose has a total volume of 400 µl, 450 µl 500 µl, 550 µl, 600 µl, 650 µl or 700 µl.

The vaccine for in ovo vaccination may contain the dose in a volume of 50 to 100 µl, preferably 50 µl. Preferably, the single-dose for in ovo vaccines has a total volume between about 10 µl and 250 µl, more preferably between about 15 µl and 200 µl, even more preferably between about 20 µl and 150 µl, even more preferably between about 30 µl and 100 µl, even more preferably between about 30 µl and 75 µl and with a single 30 µl, 35 µl, 40 µl, 45 µl, 50 µl, 55 µl, 60 µl, 65 µl, 70 µl or 75 µl dose being preferred. Most preferred the single-dose has a total volume of 40 µl, 45 µl, 50 µl, 55 µl or 60 µl.

The vaccine for intramuscular or subcutaneous vaccination or one dose of a drinking water vaccine may contain the dose in a volume of 30 µl to 1000 µl. Preferably, the single-dose has a total volume between about 30 µl and 1000 µl, more preferably between about 50 µl and 500 µl, more preferably between about 75 µl and 250 µl and even more preferably between about 100 µl and 200 µl with a single 100 µl, 110 µl, 120 µl, 125 µl, 130 µl, 135 µl, 140 µl, 145 µl, 150 µl, 160 µl, 170 µl, 175 µl, 180 µl, 190 µl, 155 µl, or 200 µl dose being the most preferred.

In one aspect of the present invention the immunogenic composition is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above.

In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

Preferably, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary, the initial (first) vaccination is performed at 1-10 days of age and the second vaccination (booster) is performed with a live or inactivated vaccine at 6-12 or 16-18 weeks of age. More preferably, the initial (first) vaccination is performed at one day-of-age and the second vaccination (booster) is performed with a live or inactivated vaccine at 6-12 or 16-18 weeks of age.

In case in ovo vaccination is used, preferably the first administration is performed when embryos are between 15 to 19 days old, preferably at day 17, 18 or 19, most preferably at day 18 of age. A second administration can be performed within the first three weeks of age, preferably within the first 10 days of age.

In one aspect of the present invention said immunogenic composition is administered subcutaneously, intramuscularly, oral, in ovo, via spray, via drinking water or by eye drop.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, most preferred the immunogenic composition is administered subcutaneously, intramuscularly, oral, in ovo, via spray, via drinking water or by eye drop.

Live IBV vaccines are preferably administered individually by eye drop, intranasal, intramuscular or subcutaneous.

More preferably, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

In Ovo Administration

As outlined above, the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e. g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

Preferably, the vaccine is injected into embryonated eggs during late stages of the embryonation, generally during the final quarter of the incubation period, preferably 3-4 days prior to hatch. Preferably, the administration is performed when embryos are between 15 to 19 days old, preferably at day 17, 18 or 19, most preferably at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined. However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apathogenic for embryos.

In one aspect of the present invention said immunogenic composition is administered via eye drop.

Typically, the live vaccine for post-hatch administration comprises the attenuated IBV in a concentration of $10^1$ to $10^8$ $EID_{50}$ (50% Egg Infective Dose) per dose, preferably in a concentration of $10^2$ to $10^5$ $EID_{50}$ per dose and, more preferably, in a concentration of $10^2$ to $10^4$ $EID_{50}$ per dose and, even more preferably, in a concentration of $10^2$ to $10^3$ $EID_{50}$ per dose.

The live vaccine for in ovo administration typically comprises an amount of the attenuated IBV of $10^2$ to $10^7$ $EID_{50}$/embryo, preferably $10^2$ to $10^3$ $EID_{50}$/embryo in a volume of 50 to 100 µl, preferably 50 µl.

Preferably, the immunogenic composition of the present invention comprises the IBV of the present invention in amounts of about 1 to about 10 $\log_{10}$ EID (egg infective dose)$_{50}$ per dose, preferably about 2 to about 8 $\log_{10}$ $EID_{50}$ per dose, preferably in an amount of about 2 to about 7 $\log_{10}$ $EID_{50}$ per dose, more preferably in an amount of about 2 to about 6 $\log_{10}$ $EID_{50}$ per dose, even more preferably in an amount of about 2 to about 5 $\log_{10}$ $EID_{50}$ per dose, even more preferably in an amount of about 2 to about 4 $\log_{10}$ $EID_{50}$ per dose, most preferably in an amount of about 2 to about 3 $\log_{10}$ $EID_{50}$ per dose. More preferably, the immunogenic composition of the present invention comprises the IBV of the present invention in amounts of about 1, 1.5, 2, 2.5, 3, 3.5, 4, 4.5, 5, 5.5, 6, 6.5, 7, 7.5 or $\log_{10}$ $EID_{50}$ per dose.

In one aspect of the present invention the immunogenic composition comprises 1 to 10 $\log_{10}$ $EID_{50}$ per dose of the IBV.

In one aspect of the present invention the immunogenic composition comprises 2 to 5 $\log_{10}$ $EID_{50}$ per dose of the IBV.

In one aspect of the present invention the immunogenic composition comprises 2 to 4 $\log_{10}$ $EID_{50}$ per dose of the IBV.

In one aspect of the present invention the immunogenic composition is administered to subjects within the first week of age, within the first three days of age, within the first two days of age, or within the first day of age.

Preferably, the subject to be immunized is 1, 2, 3, 4, 5, 6, 7, 8, 9, 10, 11, 12, 13, 14, 15, 16, 17, 18, 19, 20 or 21 days of age. More preferably, said subject to be immunized is 1, 2, 3, 4, 5, 6, 7, 8, 9, 10, 11, 12, 13 or 14 days of age. Most preferably, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, preferably, the subjects are immunized within the first 24 h of age.

In one aspect of the present invention the immunogenic composition is administered to subjects within the first day of age. As shown in the Examples the immunogenic composition as provided herein has been proven to be safe and efficacious when administered to 1-day old poultry.

In one aspect of the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" is well known to the person skilled in that art. The term virus load is interchangeable used with the term viral titer herein. The virus load or virus titer is a measure of the severity of an active viral infection, and can be determined by methods known to the person skilled in the art. The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

The term "ciliostasis" is well known to the person skilled in that art. The surface of the trachea is covered with specialised epithelial cells, which are lined with numerous, motile, hair-like structures called cilia. The term "ciliostasis" encompasses the reduction or loss of cilia and/or loss or partial loss of ciliary activity. Ciliostasis can be determined without further ado by the person skilled in the art.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term "egg drop" encompasses a decreased egg production.

In one aspect of the present invention the treatment or prevention results in a prevention or reduction of ciliostasis as compared to subjects of a non-treated control group of the same species.

In one aspect of the present invention the treatment or prevention results in a prevention or reduction of kidney lesions as compared to subjects of a non-treated control group of the same species.

In one aspect of the present invention the treatment or prevention results in a prevention or reduction of egg drop as compared to subjects of a non-treated control group of the same species.

The present invention further provides an IBV or an immunogenic composition as described herein for therapeutic use.

The present invention further provides an IBV or an immunogenic composition as described herein for use as an immunogen or vaccine.

The present invention further provides an IBV or an immunogenic composition as described herein for use as a medicament.

The present invention further provides the use of the IBV or immunogenic composition as described herein for the manufacture of a medicament.

The present invention further provides the use of the IBV or immunogenic composition as described herein for the treatment and/or prophylaxis of IBV infections in a subject.

The present invention further provides an immunogenic composition comprising an H52 IBV (infectious bronchitis virus) encoding for a heterologous S (spike) protein or fragment thereof, wherein said H52 IBV comprises a Nucleocapsid (N) protein, Envelope (E) protein or Membrane glycoprotein (M) having an amino acid sequence as shown for SEQ ID NO:2, SEQ ID NO:3, SEQ ID NO:4, AY044185 (SEQ ID NO:80), AF352310 (SEQ ID NO:81), AF317210 (SEQ ID NO:82) or AF286185 (SEQ ID NO:83) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto, and, wherein the heterologous S protein or fragment thereof is selected from a list of genotypes or serotypes consisting of 4/91, QX, Q1, Arkansas, Variant 2 and Brazil or from an amino acid sequence as shown SEQ ID NO: 5, 6, 7, 8, 9, 10, 11, 12, 13, 14, 15 or 16 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

In another specific aspect of the immunogenic composition according to the present invention the heterologous S protein is the full length spike protein.

In another specific aspect of the immunogenic composition according to the present invention the fragment of the heterologous S (spike) protein has a length of at least 500, 750, 1000 or 1077 amino acids from the N-Terminus.

In another specific aspect of the immunogenic composition according to the present invention the fragment of the heterologous S (spike) protein is the Ectodomain of the spike protein.

In another specific aspect of the immunogenic composition according to the present invention the IBV is attenuated.

The present invention further provides a method of preparing an immunogenic composition for the treatment and/or prophylaxis of IBV infections in a subject comprising:

a.) providing an H52 IBV comprising a spike (S) protein, nucleocapsid (N) protein, envelope (E) protein or membrane glycoprotein (M) having an amino acid sequence as shown for SEQ ID NO:1, SEQ ID NO:2, SEQ ID NO:3, SEQ ID NO:4, AF352315 (SEQ ID NO:79), AY044185 (SEQ ID NO:80), AF352310 (SEQ ID NO:81), AF317210 (SEQ ID NO:82) or AF286185 (SEQ ID NO:83) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto; and b.) providing a heterologous S protein or fragment thereof selected from a list of genotypes or serotypes consisting of 4/91, QX, Q1, Arkansas, Variant 2 and Brazil or from an amino acid sequence as shown SEQ ID NO: 5, 6, 7, 8, 9, 10, 11, 12, 13, 14, 15 or 16 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto; and c.) replacing the spike protein or fragment thereof of H52 IBV of a) with said heterologous S (spike) protein or fragment thereof of b) to have an H52 IBV with a heterologous S protein or fragment thereof; and d.) obtaining said H52 IBV with a heterologous S protein or fragment thereof; and e.) addition of a pharmaceutically acceptable carrier.

The term "obtaining" comprises the harvest, isolation, purification and/or formulation (e.g. finishing, inactivation and/or blending) of said H52 IBV with a heterologous S protein or fragment thereof.

The term "harvest" refers to collecting or recovering said said H52 IBV with a heterologous S protein or fragment thereof from the transfected or infected cell or cell line. Any conventional method known in the art can be used, e.g. any separation method. Well known methods in the art comprise centrifugation or filtration, such as using a semi-permeable membrane having a certain pore size.

The term "isolation" comprises an isolation step of said H52 IBV with a heterologous S protein or fragment thereof. Methods for the isolation from the transfected or infected cell or cell line are known to a person skilled in the art. Those methods comprise physical and/or chemical methods, including but are not limited to freeze thaw cycles, treatment with ultrasound and the alike.

Methods for the "purification" of said said H52 IBV with a heterologous S protein or fragment thereof from the isolate are known to a person skilled in the art, for example by those methods described in Protein purification methods—a practical approach (E. L. V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The vector can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein may also include further finishing steps as part of the final formulation process, like the addition of buffer, inactivation, neutralization steps and the alike.

In another specific aspect of the method of preparing an immunogenic composition according to the present invention, the fragment of the heterologous S (spike) protein is the ectodomain of the spike protein.

In another specific aspect of the immunogenic composition according to the present invention said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

In another specific aspect of the method of preparing an immunogenic composition according to the present invention, the heterologous S protein is the full length spike protein.

The present invention further concerns a plasmid comprising a nucleic acid encoding a partial H52 IBV (infectious bronchitis virus) genome including a heterologous IBV S (spike) protein or fragment thereof, such as the pUC57-s H52 rIBV CR88 S Ecto donor plasmid (SEQ ID NO:21).

Clauses

The following clauses are also described herein:

1. An H52 IBV (infectious bronchitis virus) encoding for a heterologous IBV S (spike) protein or fragment thereof.

2. An immunogenic composition comprising an H52 IBV (infectious bronchitis virus) encoding for a heterologous S (spike) protein or fragment thereof.

3. An immunogenic composition comprising an IBV (infectious bronchitis virus) of clause 1.

IBV H52—Definition by Protein Encoding Sequences

4. The IBV or the immunogenic composition of any one of clauses 1 to 3, wherein the H52 IBV has or consists of or comprises a nucleotide sequence as shown for EU817497 (SEQ ID NO:78) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

5. The IBV or the immunogenic composition of any one of clauses 1 to 4, wherein the H52 IBV strain has or consists of or comprises a spike (S1) protein having an amino acid sequence as shown for AF352315 (SEQ ID NO:79) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

6. The IBV or the immunogenic composition of any one of clauses 1 to 5, wherein the H52 IBV strain has or consists of or comprises a spike (S) protein having an amino acid sequence as shown SEQ ID NO:1 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

7. The IBV or the immunogenic composition of any one of clauses 1 to 6, wherein the H52 IBV has or consists of or comprises a nucleocapsid (N) protein having an amino acid sequence as shown for AY044185 (SEQ ID NO:80) or AF352310 (SEQ ID NO:81) a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

8. The IBV or the immunogenic composition of any one of clauses 1 to 7, wherein the H52 IBV has or consists of or comprises a nucleocapsid (N) protein having an amino acid sequence as shown SEQ ID NO:2 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

9. The IBV or the immunogenic composition of any one of clauses 1 to 8, wherein the H52 IBV has or consists of or comprises an envelope (E) protein having an amino acid sequence as shown for AF317210 (SEQ ID NO: 82) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

10. The IBV or the immunogenic composition of any one of clauses 1 to 9, wherein the H52 IBV has or consists of or comprises an envelope (E) protein having an amino acid sequence as shown in SEQ ID NO:3 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

11. The IBV or the immunogenic composition of any one of clauses 1 to 10, wherein the H52 IBV has or consists of or comprises a membrane glycoprotein (M) protein having an amino acid sequence as shown for AF286185 (SEQ ID NO:83) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

12. The IBV or the immunogenic composition of any one of clauses 1 to 11, wherein the H52 IBV has a or consists of or comprises membrane glycoprotein (M) protein having an amino acid sequence as shown in SEQ ID NO:4 or a sequence having at least 95%, 96%, 97%, 98%, 99%, 99.2%, 99.5%, 99.6%, 99.7%, 99.8%, 99.9%, 99.95%, 99.98% or 99.99% sequence identity thereto.

Heterologous S Protein

13. The IBV or the immunogenic composition of any one of clauses 1 to 12, wherein the heterologous spike is of a non-Massachusetts genotype or serotype.

14. The IBV or the immunogenic composition of any one of clauses 1 to 13, wherein the heterologous S protein or fragment thereof is from an IBV with a genotype or serotype selected from a list consisting of: Arkansas (such as Arkansas 99), Brazil (such as BR-1, BR-2, 23/2013, IBV/Brazil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy (such as Italy 02), JMK, LDT3, Maine (such as Maine 209), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

15. The IBV or the immunogenic composition of any one of clauses 1 to 14, wherein the heterologous S protein or fragment thereof is from an IBV selected from a list of genotypes or serotypes consisting of 4/91, QX, Q1, Italy 02, Arkansas, Connecticut, Georgia, LDT3, PL84084, Variant 2 or Brazil.

16. The IBV or the immunogenic composition of any one of clauses 1 to 15, wherein the heterologous S protein or fragment thereof is from an IBV selected from a list of genotypes or serotypes consisting of 4/91, QX, Q1, Arkansas, Variant 2 and Brazil.

17. The IBV or the immunogenic composition of clause 16, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91attenuated, IB4-91 and CR88.

18. The IBV or the immunogenic composition of clause 16, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

19. The IBV or the immunogenic composition of clause 16, wherein the Q1 strain is selected from a list consisting of: CK/CH/LDL/98I, CK/CH/LSD/08-10, J2, Q1, AR08ER22, AR08BA21 and Chile-295-10.

20. The IBV or the immunogenic composition of clause 16, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

21. The IBV or the immunogenic composition of clause 16, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

22. The IBV or the immunogenic composition of clause 16, wherein the Brazil strain is selected from a list consisting of: BR-1, BR-2, 23/2013 and IBV/Brazil/351/1984.

23. The IBV or the immunogenic composition of any one of clauses 1 to 22, wherein the heterologous S protein or fragment thereof is from 4/91 genotype or serotype.

24. The IBV or the immunogenic composition of any one of clauses 1 to 23, wherein the heterologous S protein or fragment thereof is from genotype or serotype 4/91 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:5 or 6 or the heterologous S protein or fragment thereof consists of or comprises an amino acid sequence as shown in SEQ ID NO: 5 or 6 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

25. The IBV or the immunogenic composition of any one of clauses 1 to 24, wherein the heterologous S protein or fragment thereof is from genotype or serotype QX having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:7 or 8 or the heterologous S protein or fragment thereof consists of or comprises an amino acid sequence as shown in SEQ ID NO: 7 or 8 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

26. The IBV or the immunogenic composition of any one of clauses 1 to 25, wherein the heterologous S protein or fragment thereof is from genotype or serotype Q1 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:9 or 10 or the heterologous S protein or fragment thereof consists of or comprises an amino acid sequence as shown in SEQ ID NO: 9 or 10 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

27. The IBV or the immunogenic composition of any one of clauses 1 to 26, wherein the heterologous S protein or fragment thereof is from genotype or serotype Arkansas having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:11 or 12 or the heterologous S protein or fragment thereof consists of or comprises an amino acid sequence as shown in SEQ ID NO: 11 or 12 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

28. The IBV or the immunogenic composition of any one of clauses 1 to 27, wherein the heterologous S protein or fragment thereof is from genotype or serotype Variant 2 having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:13 or 14 or the heterologous S protein or fragment thereof consists of or comprises an amino acid sequence as shown in SEQ ID NO: 13 or 14 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

29. The IBV or the immunogenic composition of any one of clauses 1 to 28, wherein the heterologous S protein or fragment thereof is from genotype or serotype Brazil having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity to SEQ ID NO:15 or 16 or the heterologous S protein or fragment thereof consists of or comprises an amino acid sequence as shown in SEQ ID NO: 15 or 16 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

30. The IBV or the immunogenic composition of any one of clauses 1 to 29, wherein the heterologous S protein or fragment thereof is selected from a list consisting of SEQ ID NO: 5, 6, 7, 8, 9, 10, 11, 12, 13, 14, 15 or 16.

31. The IBV or the immunogenic composition of any one of clauses 1 to 30, wherein the heterologous S protein is the full length Spike protein.

32. The IBV or the immunogenic composition of any one of clauses 1 to 31, wherein the fragment of the heterologous S (spike) protein has a length of at least 500, 750, 1000 or 1077 amino acids.

33. The IBV or the immunogenic composition of any one of clauses 1 to 32, wherein the fragment of the heterologous S (spike) protein has a length of at least 500, 750, 1000 or 1077 amino acids from the N-Terminus.

34. The IBV or the immunogenic composition of any one of clauses 1 to 33, wherein the fragment of the heterologous S (spike) protein has a length of at least 1000 amino acids.

35. The IBV or the immunogenic composition of any one of clauses 1 to 34, wherein the fragment of the heterologous S (spike) protein is the ectodomain of the spike protein.

36. The IBV or the immunogenic composition of any one of clauses 1 to 35, wherein the heterologous S (spike) protein or fragment thereof replaces the homologous S protein or fragment thereof.

37. The IBV or the immunogenic composition of any one of clauses 1 to 36, wherein the heterologous S (spike) protein or fragment thereof replaces the natural occurring S protein or fragment thereof.

38. The IBV or the immunogenic composition of any one of clauses 1 to 37, wherein the heterologous S (spike) protein or fragment thereof replaces the S protein or fragment thereof in H52.

39. The IBV or the immunogenic composition of any one of clauses 1 to 38, wherein the IBV is attenuated.

40. The IBV or the immunogenic composition of any one of clauses 1 to 39, wherein the IBV is inactivated.

41. The IBV or the immunogenic composition of any one of clauses 1 to 40, wherein the IBV is genetically engineered.

42. The IBV or the immunogenic composition of any one of clauses 1 to 41, wherein the IBV is a recombinant IBV.

43. The immunogenic composition of any one of clauses 2 to 42, wherein the immunogenic composition is a vaccine.

44. The immunogenic composition of any one of clauses 2 to 43, wherein the immunogenic composition comprises a pharmaceutically acceptable carrier.

45. The immunogenic composition of clause 44, wherein the pharmaceutically acceptable carrier is phosphate buffered saline.

46. The immunogenic composition of any one of clauses 2 to 45, wherein the immunogenic composition is effective in the treatment and/or prophylaxis of clinical signs caused by IBV in a subject of need.

47. The immunogenic composition of any one of clauses 2 to 46, wherein the immunogenic composition protects against a challenge with an IBV strain of the serotype of the heterologous spike protein.

48. The immunogenic composition of any one of clauses 2 to 47, wherein the immunogenic composition protects against a challenge with strains of 4/91, QX, Q1, Arkansas Variant 2 or Brazil genotype.

49. The immunogenic composition of any one of clauses 2 to 48, wherein the immunogenic composition protects against a challenge with strains of 4/91 genotype.

50. The immunogenic composition of any one of clauses 2 to 49, wherein said immunogenic composition is formulated for a single-dose administration.

51. The immunogenic composition of any one of clauses 2 to 50, wherein said immunogenic composition is administered subcutaneously, intramuscularly, oral, in ovo, via spray, via drinking water or by eye drop.

52. The immunogenic composition of any one of clauses 2 to 51, wherein the immunogenic composition comprises 1 to 10 $\log_{10}$ $EID_{50}$ per dose of the IBV.

53. The immunogenic composition of any one of clauses 2 to 52, wherein the immunogenic composition comprises 2 to 5 $\log_{10}$ $EID_{50}$ per dose of the IBV.

54. The immunogenic composition of any one of clauses 2 to 53, wherein the immunogenic composition comprises 2 to 4 $\log_{10}$ $EID_{50}$ per dose of the IBV.

55. A kit comprising the IBV or the immunogenic composition of any one of clauses 1 to 54.

56. The kit according to clause 55, wherein the kit further comprises an instruction letter for the treatment and/or prophylaxis of diseases of avians.

57. The kit according to clause 55, wherein the kit further comprises an instruction letter for the treatment and/or prophylaxis of diseases of poultry.

58. The kit according to clauses 55, wherein the kit further comprises an instruction letter for the treatment and/or prophylaxis of IB.

59. A method for immunizing a subject comprising administering to such subject an immunogenic composition according to any one of clauses 2 to 54.

60. A method of treating or preventing clinical signs caused by IBV in a subject of need, the method comprising administering to the subject a therapeutically effective amount of an immunogenic composition according to any one of clauses 2 to 54.

61. A method of reducing the ciliostasis in a subject of need, in comparison to a subject of a non-immunized control group of the same species, the method comprising administering to the subject a therapeutically effective amount of an immunogenic composition according to any one of clauses 2 to 54.

62. The immunogenic composition according to any one of clauses 2 to 54 for use in a method for immunizing a subject, the method comprising administering to the subject a therapeutically effective amount of said immunogenic composition.

63. The immunogenic composition according to any one of clauses 2 to 54 for use in a method of treating or preventing clinical signs caused by IBV in a subject of need, the method comprising administering to the subject a therapeutically effective amount of said immunogenic composition.

64. The immunogenic composition according to any one of clauses 2 to 54 for use in a method of reducing the ciliostasis in a subject of need, in comparison to a subject of a non-immunized control group of the same species, the method comprising administering to the subject a therapeutically effective amount of said immunogenic composition.

65. The method or use of any one of clauses 59 to 64, wherein said subject is avian.

66. The method or use of any one of clauses 59 to 65, wherein said subject is poultry.

67. The method or use of any one of clauses 59 to 66, wherein said subject is selected from the list consisting of chicken, turkey, quail, or pheasant.

68. The method or use of any one of clauses 59 to 67, wherein said subject is chicken.

69. The method or use of any one of clauses 59 to 68, wherein the immunogenic composition is administered once.

70. The method or use of any one of clauses 59 to 68, wherein the immunogenic composition is administered at two or more doses.

71. The method or use of any one of clauses 59 to 70, wherein said immunogenic composition is administered subcutaneously, intramuscularly, oral, in ovo, via spray, via drinking water or by eye drop.

72. The method or use of any one of clauses 59 to 71, wherein said immunogenic composition is administered via eye drop.

73. The method or use of any one of clauses 59 to 72, wherein the immunogenic composition comprises 1 to 10 $\log_{10}$ $EID_{50}$ per dose of the IBV.

74. The method or use of any one of clauses 59 to 73, wherein the immunogenic composition comprises 2 to 5 $\log_{10}$ $EID_{50}$ per dose of the IBV.

75. The method or use of any one of clauses 59 to 74, wherein the immunogenic composition comprises 2 to 4 $\log_{10}$ $EID_{50}$ per dose of the IBV.

76. The method or use of any one of clauses 59 to 75, wherein the immunogenic composition is administered to subjects within the first week of age, within the first three days of age, within the first two days of age, or within the first day of age.

77. The method or use of any one of clauses 59 to 76, wherein the immunogenic composition is administered to subjects within the first day of age.

78. The method or use of any one of clauses 59 to 77, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

79. The method or use of any one of clauses 59 to 78, wherein the treatment or prevention results in a prevention or reduction of ciliostasis as compared to subjects of a non-treated control group of the same species.

80. The method or use of any one of clauses 59 to 79, wherein the treatment or prevention results in a prevention or reduction of kidney lesions as compared to subjects of a non-treated control group of the same species.

81. The method or use of any one of clauses 59 to 80, wherein the treatment or prevention results in a prevention or reduction of egg drop as compared to subjects of a non-treated control group of the same species.

82. The IBV or immunogenic composition of any one of clauses 1 to 54 for therapeutic use.

83. The IBV or immunogenic composition of any one of clauses 1 to 54 for use as an immunogen or vaccine.

84. The IBV or immunogenic composition any one of clauses 1 to 54 for use as a medicament.

85. Use of the IBV or immunogenic composition of any one of clauses 1 to 54 for the manufacture of a medicament.

86. Use of the IBV or immunogenic composition of any one of clauses 1 to 54 for the treatment and/or prophylaxis of IBV infections in a subject.

87. An immunogenic composition comprising an H52 IBV (infectious bronchitis virus) encoding for a heterologous S (spike) protein or fragment thereof, wherein said H52 IBV comprises a Nucleocapsid (N) protein, Envelope (E) protein or Membrane glycoprotein (M) having or consisting of or comprising an amino acid sequence as shown for SEQ ID NO:2, SEQ ID NO:3, SEQ ID NO:4, AY044185 (SEQ ID NO:80), AF352310 (SEQ ID NO:81), AF317210 (SEQ ID NO:82) or AF286185 (SEQ ID NO:83) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto, and, wherein the heterologous S protein or fragment thereof is selected from a list of genotypes or serotypes consisting of 4/91, QX, Q1, Arkansas, Variant 2 and Brazil or from an amino acid sequence as shown SEQ ID NO: 5, 6, 7, 8, 9, 10, 11, 12, 13, 14, 15 or 16 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto or the heterologous S protein or fragment thereof consists of or comprises an amino acid sequence as shown in SEQ ID NO: 5, 6, 7, 8, 9, 10, 11, 12, 13, 14, 15 or 16 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto.

88. The immunogenic composition of clause 87, wherein the heterologous S protein is the full length Spike protein.

89. The immunogenic composition of clause 87, wherein the fragment of the heterologous S (spike) protein has a length of at least 500, 750, 1000 or 1077 amino acids from the N-Terminus.

90. The immunogenic composition of clause 87 or 89, wherein the fragment of the heterologous S (spike) protein is the Ectodomain of the spike protein.

91. The immunogenic composition of any one of clauses 87 to 90, wherein the IBV is attenuated.

92. A method of preparing an immunogenic composition for the treatment and/or prophylaxis of IBV infections in a subject comprising:
  a.) providing an H52 IBV comprising a spike (S) protein, Nucleocapsid (N) protein,
  Envelope (E) protein or Membrane glycoprotein (M) having or consisting of or comprising an amino acid sequence as shown for SEQ ID NO:1, SEQ ID NO:2, SEQ ID NO:3, SEQ ID NO:4, AF352315 (SEQ ID NO:79), AY044185 (SEQ ID NO:80), AF352310 (SEQ ID NO:81), AF317210 (SEQ ID NO:82) or AF286185 (SEQ ID NO:83) or a sequence having at least 95%, 96%, 97%, 98%, 99%, 99.2%, 99.5%, 99.6%, 99.7%, 99.8%, 99.9%, 99.95%, 99.98% or 99.99% sequence identity thereto; and
  b.) providing a heterologous S protein or fragment thereof selected from a list of genotypes or serotypes consisting of 4/91, QX, Q1, Arkansas, Variant 2 and Brazil or from an amino acid sequence as shown SEQ ID NO: 5, 6, 7, 8, 9, 10, 11, 12, 13, 14, 15 or 16 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto or providing a heterologous S protein or fragment thereof consisting of or comprising an amino acid sequence as shown in SEQ ID NO: 5, 6, 7, 8, 9, 10, 11, 12, 13, 14, 15 or 16 or a sequence having at least 90%, 91%, 92%, 93%, 94%, 95%, 96%, 97%, 98%, 99%, 99.2%, 99.5%, 99.6%, 99.7%, 99.8%, 99.9%, 99.95%, 99.98% or 99.99% sequence identity thereto; and c.) replacing the spike protein of H52 IBV of a) with said heterologous S (spike) protein or fragment thereof of b) to have an H52 IBV with a heterologous S protein or fragment thereof; and d.) obtaining said H52 IBV with a heterologous S protein or fragment thereof; and e.) addition of a pharmaceutically acceptable carrier.

93. The method of clause 92, wherein the fragment of the heterologous S (spike) protein is the Ectodomain of the Spike protein.

94. The method of clause 92 or 93, wherein said pharmaceutically acceptable carrier is selected from the group consisting of solvents, dispersion media, coatings, stabilizing agents, diluents, preservatives, antibacterial and antifungal agents, isotonic agents, adsorption delaying agents, adjuvants, immune stimulants, and combinations thereof.

95. The method of any one of clauses 92 or 94, wherein the heterologous S protein is the full length spike protein.

BRIEF DESCRIPTION OF THE DRAWINGS

FIG. 1. In ovo replication kinetics for H52 rIBV CR88 S ecto in comparison to recombinant wild type viruses H52 and CR88. One data point represents the mean of 5 samples per time point. Error bars indicate the standard deviation.

FIG. 2. Summary of ciliostasis scoring. The sum of the 10 individual scores for the 10 rings of one animal is calculated and is represented by one dot in the graph. Maximum ciliostasis corresponds to a score of 40, while absence of ciliostasis is represented by a score of 0. Mean and significance are calculated using GraphPad Prism and an ordinary one-way ANOVA test ($p<0.007$).

SEQUENCES OVERVIEW

Figure 3:
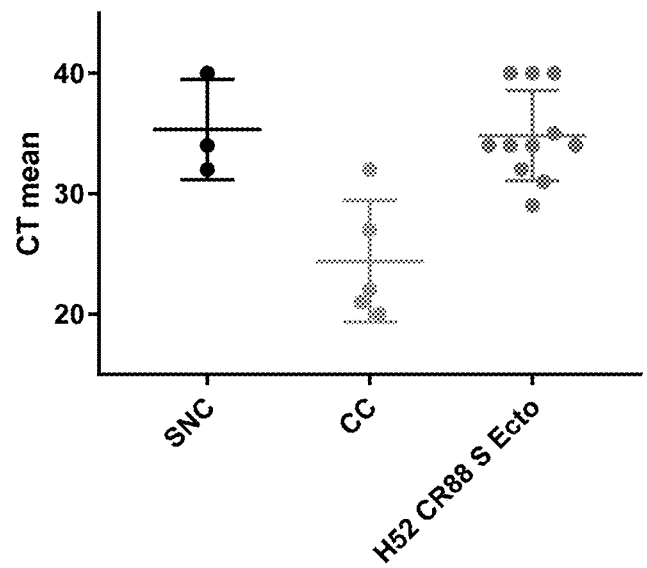
FIG. 3. Summary of RT-qPCR results of kidney tissues. Each individual bird is indicated by one data point.

SEQ ID NO:1: H52 IBV spike (S) protein.
SEQ ID NO:2: H52 IBV nucleocapsid (N) protein.
SEQ ID NO:3: H52 IBV envelope (E) protein.
SEQ ID NO:4: H52 IBV membrane glycoprotein (M) protein.
SEQ ID NO:5 and 6: Heterologous S protein or fragment from genotype or serotype 4/91.
SEQ ID NO:7 and 8: Heterologous S protein or fragment thereof from genotype or serotype QX.
SEQ ID NO:9 and 10: Heterologous S protein or fragment thereof from genotype or serotype Q1.
SEQ ID NO:11 and 12: Heterologous S protein or fragment thereof from genotype or serotype Arkansas.
SEQ ID NO:13 and 14: Heterologous S protein or fragment thereof from genotype or serotype Variant 2.
SEQ ID NO:15 and 16: Heterologous S protein or fragment thereof from genotype or serotype Brazil.
SEQ ID NO:17: IBV CR88 spike nucleic acid coding sequence.
SEQ ID NO:18: IBV H52 spike ectodomain nucleic acid coding sequence
SEQ ID NO:19: pUC57-s H52 rIBV donor plasmid.
SEQ ID NO:20: IBV CR88 spike ectodomain nucleic acid coding sequence.
SEQ ID NO:21: pUC57-s H52 rIBV CR88 S Ecto donor plasmid.
SEQ ID NO:22 to SEQ ID NO:77: Primer.
SEQ ID NO:78: EU817497 (H52 IBV nucleotide sequence)
SEQ ID NO:79: AF352315 (H52 IBV S protein amino acid sequence)
SEQ ID NO:80: AY044185 (H52 IBV N protein amino acid sequence)
SEQ ID NO:81: AF352310 (H52 IBV N protein amino acid sequence)
SEQ ID NO:82: AF317210 (H52 IBV E protein amino acid sequence)
SEQ ID NO:83: AF286185 (H52 IBV M protein amino acid sequence)
SEQ ID NO:84 and SEQ ID NO:85: Primer

EXAMPLES

The following examples are set forth below to illustrate specific embodiments of the present invention. These examples are merely illustrative and are understood not to limit the scope or the underlying principles of the present invention.

Example 1

Generation of Recombinant IBV H52 in Which the Coding Sequence For the H52 Spike or Spike Ectodomain is Replaced by the Coding Sequence For a Heterologous Spike or Spike Ectodomain Donor Plasmid Construction Exemplary the replacement of the H52 spike ectodomain by the CR88 ectodomain is described in detail: The IBV CR88 spike nucleic acid coding sequence (SEQ ID NO:17) is synthesized by a commercial supplier. It is used as a template to replace the IBV H52 spike ectodomain nucleic acid coding sequence (SEQ ID NO:18) in the pUC57-s IBV-5-1b-S-SIR-3T donor plasmid described by van Beurden et al. (Virol J. 2017; 14(1):109), hereafter referred to as pUC57-s H52 rIBV donor plasmid (SEQ ID NO:19). Bases 1717 to 4941 of SEQ ID NO:19 are replaced with the corresponding IBV CR88 spike ectodomain nucleic acid coding sequence (SEQ ID NO:20) which corresponds to bases 55 to 3285 of SEQ ID NO 15, respectively. This generates the pUC57-s H52 rIBV CR88 S Ecto donor plasmid (SEQ ID NO:21) in which the IBV CR88 spike ectodomain is encoded by bases 1717 to 4947. For this, the pUC57-s H52 rIBV donor plasmid (SEQ ID NO:19) is digested using the unique restriction sites 5' (EcoRV) and 3' (PmlI) close to the H52 spike coding sequence to linearize the plasmid and remove the H52 spike and flanking sequences. The QIAquick gel extraction kit (Qiagen) is used to purify the band corresponding to the pUC57-s IBV H52 backbone without the H52 spike coding sequence. The CR88 spike ectodomain nucleic acid coding sequence and the flanking 5' and 3' IBV H52 sequences are amplified in three separate PCR reactions with Q5® High-Fidelity DNA Polymerase (NEB; see table 1 for primers). The PCR products are purified by QIAquick gel extraction (Qiagen) and are used for Gibson assembly with the NEBuilder® HiFi DNA Assembly Cloning Kit (NEB) according to the kit protocol to generate the pUC57-s H52 rIBV CR88 S Ecto donor plasmid.

TABLE 1

Gibson assembly primers designed with the NEBuilder online tool by NEB and used to generate PCR products to assemble the pUC57-s H52 rIBV CR88 S Ecto donor plasmid.

| PCR | Product | Primer |
|---|---|---|
| 1 | H52 5' flank | cagagcacaagtttgatcttgtgatatctgatatgtatacagacaatgattc (SEQ ID NO: 22) <br> tatcatagagcaaagcactacatagtgcacac (SEQ ID NO: 23) |
| 2 | CR88 spike Ectodomain | actatgtagtgctttgctctatgataataatacttacg (SEQ ID NO: 24) <br> cataccaaggccatttaatataagttttgagaattgagag (SEQ ID NO: 25) |
| 3 | H52 3' flank | aacttatattaaatggccttggtatgtgtgg (SEQ ID NO: 26) <br> cttaactcctggaattactaaccacgtgtaccaaaataaacaacaagc (SEQ ID NO: 27) |

Targeted RNA Recombination and Rescue of Recombinant IBV

For the generation of recombinant IBV the method of targeted RNA recombination as described by van Beurden et al. (Virol J. 2017; 14(1):109) is applied. In brief, the H52 murinized (m)IBV is generated as described. For the generation of H52 rIBV CR88 S Ecto, LR7 cells are infected with H52 mIBV and electroporated with in vitro transcript generated from the pUC57-s H52 rIBV CR88 S Ecto donor plasmid and subsequently injected into 8 day old embryonated SPF chicken eggs (VALO BioMedia). After up to 9 days of incubation at 37.5° C. and 60% humidity, the allantoic fluids of all eggs are analyzed separately for the rescue of recombinant IBV after RNA isolation by the QIAamp viral RNA mini kit (Qiagen) and by using SuperScript™ III One-Step RT-PCR System with Platinum™ Taq DNA Polymerase (ThermoFisher). Primers PO1323 and PO1729 binding in H52 IBV 1ab and CR88 IBV S ectodomain are used (table 2) specific for recombinant IBV but not mIBV. The positive allantoic fluid of the egg inoculated with the highest dilution of LR7 cells is selected for two rounds of end-point dilution in 8-day old SPF eggs. Nucleic acids isolation of samples of the limiting dilution is performed using the MagMAX™ Core Nucleic Acid Purification Kit (ThermoFisher) with the KingFisher™ Duo Prime Purification System (ThermoFisher) and are subsequently analyzed for the presence of rIBV by the RT-PCR described above. After the second limiting dilution the positive-tested allantoic fluid of the egg inoculated with the highest dilution is used for propagation in 10-day old embryonated SPF chicken eggs. The allantoic fluid is diluted 1:1000 in 1×PBS and 100 µl is injected per egg. Allantoic fluid is harvested 48 hours post inoculation, cleared from debris and stored at −80° C. To confirm the sequence derived from the donor plasmid in the generated rIBV, viral nucleic acids are isolated with the QIAamp viral RNA mini kit followed by the SuperScript III One-Step RT-PCR using the primers listed in table 3, QIAquick PCR purification and subsequent Sanger sequencing with the same primers, performed by a commercial supplier.

TABLE 1

Primers to identify recombinant IBV after rescue

| name | sequence | Region | Amplicon [bp] |
|---|---|---|---|
| PO1323 | TCAGCATGGACGTGTGGTTA (SEQ ID NO: 28) | 1ab | ~970 |
| PO1729 | aggttggcacctatatgggg (SEQ ID NO: 29) | spike | |

TABLE 2

Sequencing primers to confirm sequence of the donor region in H52 rIBV CR88 S Ecto

| PCR | Name | Sequence | Region | Amplicon [bp] |
|---|---|---|---|---|
| 1 | PO765 <br> PO730 | tgacttggtttgaagatggc (SEQ ID NO: 30) <br> aagagatgttggtaacacct (SEQ ID NO: 31) | Pol 1ab <br> Pol 1ab | 904 |
| 2 | PO706 <br> PO1409 | gacagagcacaagtttgatc (SEQ ID NO: 32) <br> ggagtgaaaacaagatcacc (SEQ ID NO: 33) | Pol 1ab <br> S | 1044 |
| 3 | PO1398 <br> PO1410 | aatttaacagttagcgtatc (SEQ ID NO: 34) <br> tttgtatacgagagccatca (SEQ ID NO: 35) | S <br> S | 801 |
| 4 | PO1399 <br> PO1411 | ggtcctactagatgtaaggg (SEQ ID NO: 36) <br> ctctctttgacctacaccat (SEQ ID NO: 37) | S <br> S | 809 |
| 5 | PO1400 <br> PO1412 | ttgccttcagtatgtttgtg (SEQ ID NO: 38) <br> agtgaagaaagtctacctgt (SEQ ID NO: 39) | S <br> S | 803 |
| 6 | PO1401 <br> PO1413 | atttcctccgtacttcaaga (SEQ ID NO: 40) <br> tgaagataataatggcaaaagc (SEQ ID NO: 41) | S <br> S | 786 |

TABLE 2-continued

Sequencing primers to confirm sequence of the donor region in H52 rIBV CR88 S Ecto

| PCR | Name | Sequence | Region | Amplicon [bp] |
|---|---|---|---|---|
| 7 | PO1402 | tcttgaaacactctcaattct (SEQ ID NO: 42) | S | 1471 |
|   | PO715 | ggtcaccagtatatttctgc (SEQ ID NO: 43) | M |  |
| 8 | PO710 | ggtcaacaatgtaattttgct (SEQ ID NO: 44) | 5ab | 958 |
|   | PO734 | cttgtcctgctttgttaaga (SEQ ID NO: 45) | 5ab |  |
| 9 | PO1405 | ttataggttggcttgtacgc (SEQ ID NO: 46) | 5ab | 1025 |
|   | PO716 | gcccatccttaataccttcc (SEQ ID NO: 47) | N |  |
| 10 | PO759 | ctcgcattacaaaggctaag (SEQ ID NO: 48) | N | 1123 |
|   | PO719 | gctctaactctatactagcct (SEQ ID NO: 49) | 3'-UTR |  |

Generation and characterization of H52 recombinant IBV in which the coding sequence for the H52 spike or spike ectodomain is replaced by the coding sequence for a spike or spike ectodomain from another IBV genotype The same methods as described for the generation of H52 rIBV CR88 S Ecto are applied to generate and characterize recombinant H52 IBV in which the spike coding sequence (bases 1663 to 5151 in SEQ ID NO:19) or the H52 spike ectodomain coding sequence (bases 1717 to 4941 of SEQ ID NO:19) is replaced with the coding sequences for the IBV spikes or spike ectodomains of the serotypes and genotypes listed in Table 3.

TABLE 3

Primers used for Gibson assembly of H52 rIBV donor plasmids with heterologous spike or spike ectodomain

| spike | PCR | product | Primer |
|---|---|---|---|
| CR88 S SEQ ID NO: 5 | 1 | H52 5' flank | cagagcacaagtttgatcttgtgatatctgatatgtatacagacaatgattc (SEQ ID NO: 22)<br>gtttgtccaacatctcttaccagtaacttacc (SEQ ID NO: 50) |
|  | 2 | CR88 S | ttactggtaagagatgttggacaaaccgcttttac (SEQ ID NO: 51)<br>ggactttggatcattaaaacgacttttaggtctgtattg (SEQ ID NO: 52) |
|  | 3 | H52 3' flank | aaagtctgtttaatgatccaaagtcccactag (SEQ ID NO: 53)<br>cttaactcctggaattactaaccacgtgtaccaaaataaacaacaagc (SEQ ID NO: 27) |
| QX S SEQ ID NO: 7 | 1 | H52 5' flank | cagagcacaagtttgatcttgtgatatctgatatgtatacagacaatgattc (SEQ ID NO: 22)<br>acttcaccaacatctcttaccagtaacttacc (SEQ ID NO: 54) |
|  | 2 | QX S | ttactggtaagagatgttggtgaagtcactg (SEQ ID NO: 55)<br>ggactttggatcattaaaacagacttttaggtctg (SEQ ID NO: 52) |
|  | 3 | H52 3' flank | aaagtctgtttaatgatccaaagtcccactag (SEQ ID NO: 53)<br>cttaactcctggaattactaaccacgtgtaccaaaataaacaacaagc (SEQ ID NO: 27) |
| QX S Ecto SEQ ID NO: 8 | 1 | H52 5' flank | cagagcacaagtttgatcttgtgatatctgatatgtatacagacaatgattc (SEQ ID NO: 22)<br>aatcaaacaaattagcactacatagtgcacac (SEQ ID NO: 56) |
|  | 2 | QX S ecto | actatgtagtgctaatttgtttgattctgataataattatg (SEQ ID NO: 57)<br>cataccaaggccacttaatataagttttaattattgaaagttcttc (SEQ ID NO: 58) |
|  | 3 | H52 3' flank | aacttatattaagtggccttggtatgtgtgg (SEQ ID NO: 59)<br>cttaactcctggaattactaaccacgtgtaccaaaataaacaacaagc (SEQ ID NO: 27) |
| Q1 S SEQ ID NO: 9 | 1 | H52 5' flank | cagagcacaagtttgatcttgtgatatctgatatgtatacagacaatg (SEQ ID NO: 60)<br>acttcccaacatctcttaccagtaacttacc (SEQ ID NO: 61) |
|  | 2 | Q1 S | ttactggtaagagatgttggggaagtcactg (SEQ ID NO: 62)<br>ggactttggatcattaaaacagacttttaggtctg (SEQ ID NO: 52) |
|  | 3 | H52 3' flank | aaagtctgtttaatgatccaaagtcccactag (SEQ ID NO: 53)<br>cttaactcctggaattactaaccacgtgtaccaaaataaacaacaag (SEQ ID NO: 63) |
| Q1 S Ecto SEQ ID NO: 10 | 1 | H52 5' flank | cagagcacaagtttgatcttgtgatatctgatatgtatacagacaatgattc (SEQ ID NO: 22)<br>tatcaaacaaagcagcactacatagtgcacac (SEQ ID NO: 64) |
|  | 2 | Q1 S Ecto | actatgtagtgctgctttgtttgataataatgaaac (SEQ ID NO: 65)<br>cataccaaggccatttaatataagtcttgagtattgaaag (SEQ ID NO: 66) |
|  | 3 | H52 3' flank | gacttatattaaatggccttggtatgtgtgg (SEQ ID NO: 67)<br>cttaactcctggaattactaaccacgtgtaccaaaataaacaacaagc (SEQ ID NO: 27) |
| Ark S SEQ ID NO 11 | 1 | H52 5' flank | cagagcacaagtttgatcttgtgatatctgatatgtatacagacaatg (SEQ ID NO: 60)<br>acttcaccaacatctcttaccagtaacttacc (SEQ ID NO: 54) |
|  | 2 | Ark S | ttactggtaagagatgttggtgaagtcactg (SEQ ID NO: 55)<br>ctttggatcattaaaacagacttttaggtctg (SEQ ID NO: 84) |
|  | 3 | H52 3' flank | gtctgtttaatgatccaaagtcccactag (SEQ ID NO: 85)<br>cttaactcctggaattactaaccacgtgtaccaaaataaacaacaag (SEQ ID NO: 63) |

TABLE 3-continued

Primers used for Gibson assembly of H52 rIBV donor plasmids with heterologous spike or spike ectodomain

| spike | PCR | product | Primer |
|---|---|---|---|
| Ark S Ecto SEQ ID NO 12 | 1 | H52 5' flank | cagagcacaagtttgatcttgtgatatctgatatgtatacagacaatgattc (SEQ ID NO: 22)<br>tgtcatataaattagcactacatagtgcacac (SEQ ID NO: 68) |
| | 2 | Ark S Ecto | actatgtagtgctaatttatatgacaacgaatcttttg (SEQ ID NO: 69)<br>cataccaaggccacttaatataagttttgagtattgaaag (SEQ ID NO: 70) |
| | 3 | H52 3' flank | aacttatattaagtggccttggtatgtgtgg (SEQ ID NO: 59)<br>cttaactcctggaattactaaccacgtgtaccaaaataaacaacaagc (SEQ ID NO: 27) |
| Variant 2 S SEQ ID NO 13 | 1 | H52 5' flank | cagagcacaagtttgatcttgtgatatctgatatgtatacagacaatg (SEQ ID NO: 60)<br>acttcaccaacatctcttaccagtaacttacc (SEQ ID NO: 54) |
| | 2 | Variant 2 S | ttactggtaagagatgttggtgaagtcactg (SEQ ID NO: 55)<br>ggactttggatcattaaacagactttttaggtctg (SEQ ID NO: 52) |
| | 3 | H52 3' flank | aaagtctgtttaatgatccaaagtcccactag (SEQ ID NO: 53) |
| Variant 2 S Ecto SEQ ID NO 14 | 1 | H52 5' flank | cttaactcctggaattactaaccacgtgtaccaaaataaacaacaag (SEQ ID NO: 63)<br>cagagcacaagtttgatcttgtgatatctgatatgtatacagacaatgattc (SEQ ID NO: 22) |
| | 2 | Variant S Ecto | tatcaaacagagcagcactacatagtgcacac (SEQ ID NO: 71)<br>actatgtagtgctgctctgtttgataataatcag (SEQ ID NO: 72)<br>cataccaaggccacttaatataagttttaattattgaaagttcttc (SEQ ID NO: 58) |
| | 3 | H52 3' flank | aacttatattaagtggccttggtatgtgtgg (SEQ ID NO: 59)<br>cttaactcctggaattactaaccacgtgtaccaaaataaacaacaagc (SEQ ID NO: 27) |
| Brazil S SEQ ID NO 15 | 1 | H52 5' flank | cagagcacaagtttgatcttgtgatatctgatatgtatacagacaatg (SEQ ID NO: 60)<br>gttgaaccaacatctcttaccagtaacttacc (SEQ ID NO: 73) |
| | 2 | BR-1 S | ttactggtaagagatgttggttcaacctcttttac (SEQ ID NO: 74)<br>ggactttggatcattaaacagactttttaggtctg (SEQ ID NO: 52) |
| | 3 | H52 3' flank | aaagtctgtttaatgatccaaagtcccactag (SEQ ID NO: 53)<br>cttaactcctggaattactaaccacgtgtaccaaaataaacaacaag (SEQ ID NO: 63) |
| Brazil S Ecto SEQ ID NO 16 | 1 | H52 5' flank | cagagcacaagtttgatcttgtgatatctgatatgtatacagacaatgattc (SEQ ID NO: 22)<br>tattgtacaaagaagcactacatagtgcacac (SEQ ID NO: 75) |
| | 2 | BR-1 S Ecto | actatgtagtgcttctttgtacaataatgatagctatg (SEQ ID NO: 76)<br>cataccaaggccatttaatataagtttttaaaatagaaagtgtttc (SEQ ID NO: 77) |
| | 3 | H52 3' flank | aacttatattaaatggccttggtatgtgtgg (SEQ ID NO: 26)<br>cttaactcctggaattactaaccacgtgtaccaaaataaacaacaagc (SEQ ID NO: 27) |

Primers in table 2 and 3 are used for identification and sequencing of the different recombinant viruses and are adapted to the respective spike sequence if necessary.

Example 2

In Ovo Replication Kinetics

Eight day-old embryonated chicken eggs are inoculated with $10^2$ $EID_{50}$ of rIBV and the respective controls. Eggs are incubated at 37.5° C., 60% humidity and candled daily 0, 8, 24, 34, 48 and 72 hours after inoculation and embryo mortality is recorded. Five preselected eggs per sample and time point are removed and transferred to 4° C. for at least 2 hours. Subsequently, the allantoic fluid is harvested and stored at −80° C. For analysis, samples are thawed and diluted 1:10 in 1×PBS without Ca and Mg and nucleic acids are extracted with the QIAamp DNA Blood Mini kit (Qiagen) with addition of carrier RNA using the Hamilton Starlet pipet robot. Extracted nucleic acids are analyzed by RT-qPCR for the relative amount of IBV RNA with a protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the ABI™ 7900HT Fast Real-Time PCR System (Thermo Fisher Scientific). All nucleic acid samples are analyzed in triplicates using a 10-fold dilution series of IBV H52 as reference.

Figures 1, 2:
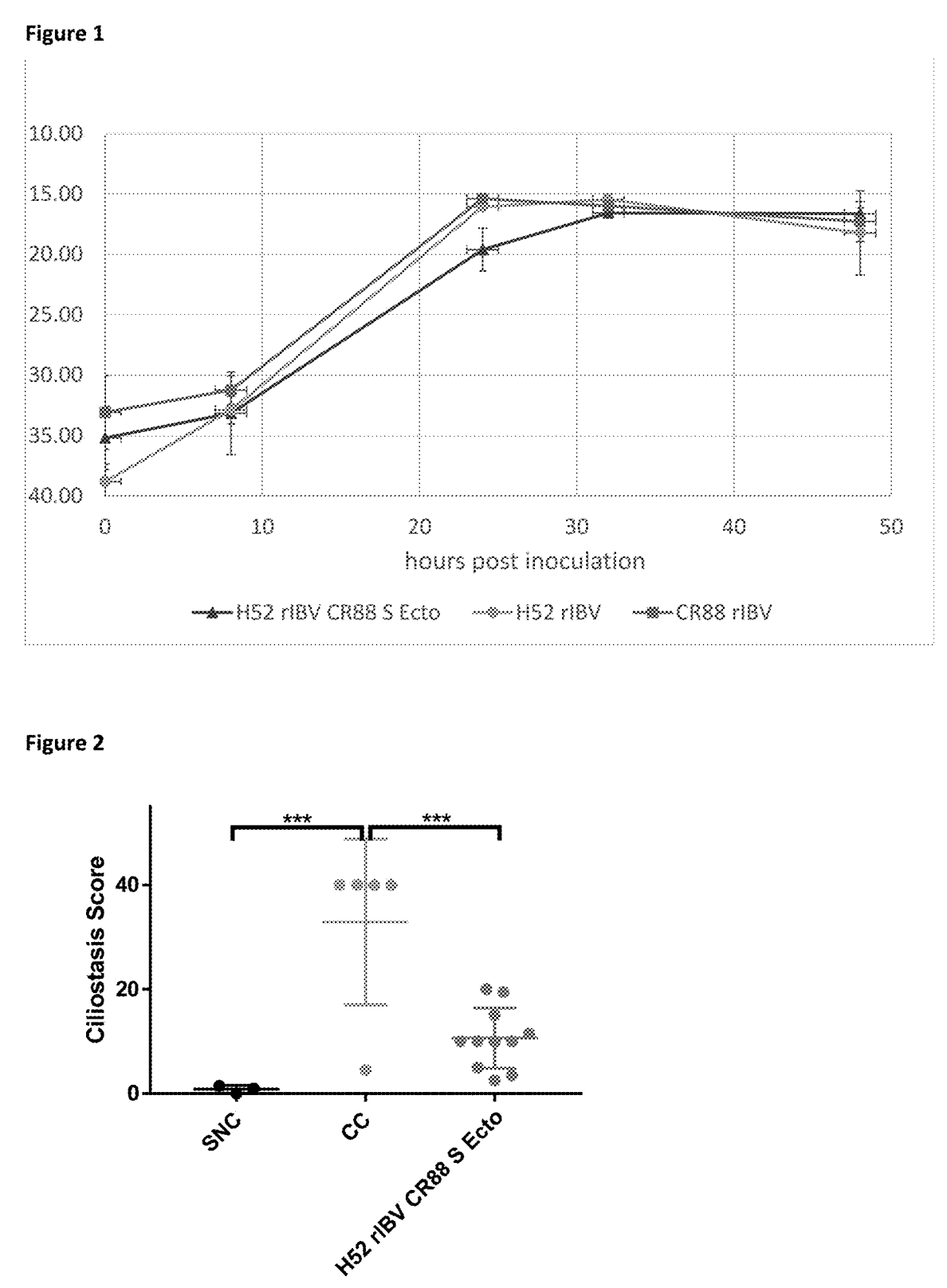

For H52 rIBV CR88 S Ecto in comparison to the recombinant wild type viruses H52 and CR88 slightly similar replication kinetics are observed at early time points. However, after 32 hours all viruses reach comparable ct values. All embryos are alive at 32 hours post inoculation, while at time point 48 hours post infection all remaining embryos are dead for all samples. Therefore, the replication of H52 rIBV CR88 S ecto is considered equally efficient compared to the wild type viruses (see Figure 1).

Example 3

Preparation of Vaccine and Challenge Virus

To demonstrate the efficacy of the H52 rIBV with heterologous spike or spike ectodomain in chickens, an aliquot of the virus stock is thawed and 10-fold diluted in 1×PBS to determine the 50% embryo infectious dose ($EID_{50}$) by inoculation of 100 μl into five 8-day old embryonated chicken eggs per dilution. Eggs are incubated at 37.5° C., 60% humidity until 7 days post inoculation. Eggs with dead embryos after 24 hours are excluded from the experiment. All other eggs with dead embryos at 7 days post inoculation are considered positive. All eggs with living embryos are candled from the bottom at 7 days post inoculation to identify dwarfs, which are considered positive. The $EID_{50}$/ml is calculated with the formula of Reed and Muench (Am J Epidemiol, 1938; 27(3):493-497). For vaccination the virus stock is diluted in 1×PBS to obtain a titer of $10^{4.3}$ EID50/ml ($10^3$ EID50 per chicken in 50 μl).

The challenge viruses for genotypes and serotypes 793B, QX, Q1, Ark, Variant 2 and Brazil are propagated in 10-day-old embryonated SPF eggs. 24 hours post inoculation the eggs are transferred to 4° C. for at least 2 hours. The allantoic fluid is harvested, aliquoted and stored at −80° C. The virus titer is determined as described above. The titer is set to $10^{4.3}$ to $10^{5.3}$ $EID_{50}$/ml by dilution with 1×PBS ($10^3$ to $10^4$ $EID_{50}$ per chicken in 50 μl).

Example 4

Determination of Vaccine Efficacy

Fertilized SPF eggs are incubated for 18 days in an egg setter at 99.7° F. and 50% humidity with 1 turn per hour. At day 18 of incubation the eggs are candled and fertile eggs are transferred to the hatcher and incubated at 99° F. and 70% humidity until hatch. Chicks without clinical signs or deformation are randomly distributed into respective treatment groups and transferred into separate isolators. At least two chicks serve as strict negative control (SNC) group, five chicks are enrolled in the challenge control (CC) group and at least 10 in groups which are vaccinated with the recombinant IBV with heterologous spike or spike ectodomain and and subsequently challenged. Animals are kept under housing conditions in compliance to local and national requirements for animal welfare recommendations. The light regime is adjusted to 16 hours light per day. Feed and water are provided ad libitum. After transfer to the isolator, chicks are vaccinated (1-day old) with $10^3$ $EID_{50}$ per chicken via eye drop (total volume 50 μl, 25 μl per eye) while the SNC and CC groups remain untreated. At 21 days post vaccination chickens of the CC and vaccinated groups are challenged with $10^3$ to $10^4$ $EID_{50}$ per chicken of the respective spike-homologous challenge strain (793B, QX, Q1, Ark, Variant 2 or Brazil) via eye drop (total volume 50 μl, 25 μl per eye). At 7 days post challenge all chickens are euthanized, choanal swabs are taken and kidneys are removed and stored in RNAlater Stabilization Solution (ThermoFisher) at 4° C. for IBV-specific RT-qPCR analysis. In addition, tracheas are removed and transferred into 50 ml tubes with warm cell culture medium. Afterwards, tracheas are cleaned from connective tissues and flushed with cell culture medium. The tracheas are cut into tracheal rings using the McIlwain tissue chopper set to 0.6-0.8 mm slice thickness. Per trachea three rings of the upper part, four rings of the middle part and three rings of the lower part are analyzed for cilia beating by light microscopy and scored for ciliostasis (see table 5). A ring is recorded as normal if more than 50% of the internal ring shows vigorous cilia movement (Score 2 and lower). A ring is recorded as positive for ciliostasis if less than 50% of the cilia are beating (Score 3 and 4). For IBV-specific RT-qPCR analysis kidney tissue pieces are warmed up to room temperature and transferred to separate 2 ml Precellys tubes, which are filled with medium and PBS, respectively. Kidneys are homogenized with the Precellys® tissue homogenizer (Bertin Instruments) for 1×20 sec at 6800 rpm. Choanal swabs are eluted in 2 ml 1×PBS. Nucleic acids are isolated from 200 μl eluate and tissue homogenate respectively using the MagMAX™ Core Nucleic Acid Purification Kit (ThermoFisher) and the KingFisher™ Duo Prime Purification System (ThermoFisher). RT-qPCR is performed as described for the in ovo kinetics above, except for using a StepOnePlus™ Real-Time PCR System (ThermoFisher) for analysis in duplicates.

TABLE 4

Scoring of ciliostasis in tracheal rings

| Ciliar activity [%] | Ciliostasis score |
|---|---|
| 100 | 0 |
| <100 - 75 | 1 |
| <75 - 50 | 2 |
| <50 - 25 | 3 |
| <25 - 0 | 4 |

Example 5

Efficacy of Recombinant IBV H52 Encoding a Heterologous Spike or Spike Ectodomain The objective of the studies is to demonstrate that recombinant IBV H52 (Mass genotype) encoding a heterologous spike or spike ectodomain is able to confer protection against challenge with a spike-homologous challenge strain.

It is analyzed if the recombinant IBV H52 encoding the spike ectodomain of IBV CR88 (4/91 genotype) is able to confer protection against challenge with a virulent 793B strain (4/91 genotype), considered as homologous challenge for the encoded IBV CR88 spike ectodomain and as heterologous challenge considering the IBV H52 backbone. All chickens are observed daily for clinical signs. No clinical signs are recorded after vaccination or challenge. Back titrations for the vaccination with H52 rIBV CR88 S Ecto at 1-day of age determine a titer of $10^{4.13}$ $EID_{50}$/ml (target $10^{4.3}$ $EID_{50}$/ml) and $10^{4.69}$ $EID_{50}$/ml (target $10^{4.3}$ $EID_{50}$/ml) for the 793B challenge virus applied at 21 days post vaccination, respectively. Ciliostasis is scored as described above and results are depicted in Error! Reference source not found.2 and summarized in Table 5 Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0).

TABLE 5

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). An animal is considered not affected if not fewer than 9 out of 10 rings show normal ciliar activity.

| Group | Vaccine | Challenge | Mean Ciliostasis Score | not affected [%] |
|---|---|---|---|---|
| 1 | — | — | 0.83 | 100 |
| 2 | — | 793B | 32.9 | 20 |

TABLE 5-continued

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). An animal is considered not affected if not fewer than 9 out of 10 rings show normal ciliar activity.

| Group | Vaccine | Challenge | Mean Ciliostasis Score | not affected [%] |
|---|---|---|---|---|
| 3 | H52 rIBV CR88 S Ecto | 793B | 10.64 | 82 |

Figure 4:
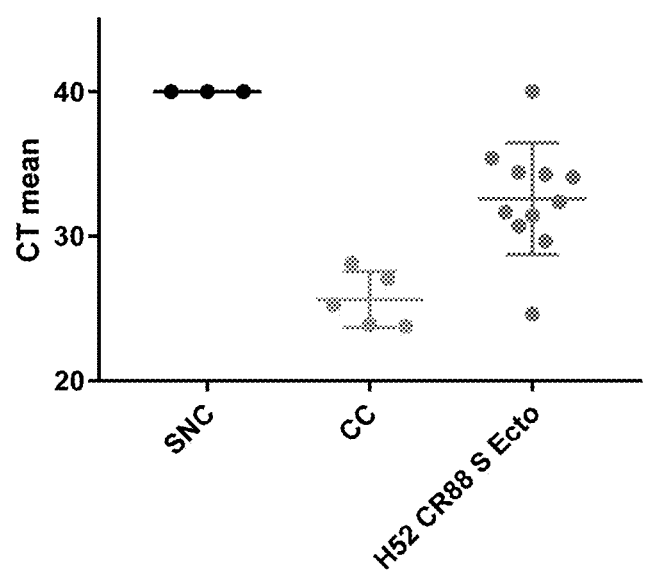
FIG. 4. Summary of RT-qPCR results of choanal swab eluates. Each individual bird is indicated by one data point.
Figure 5:
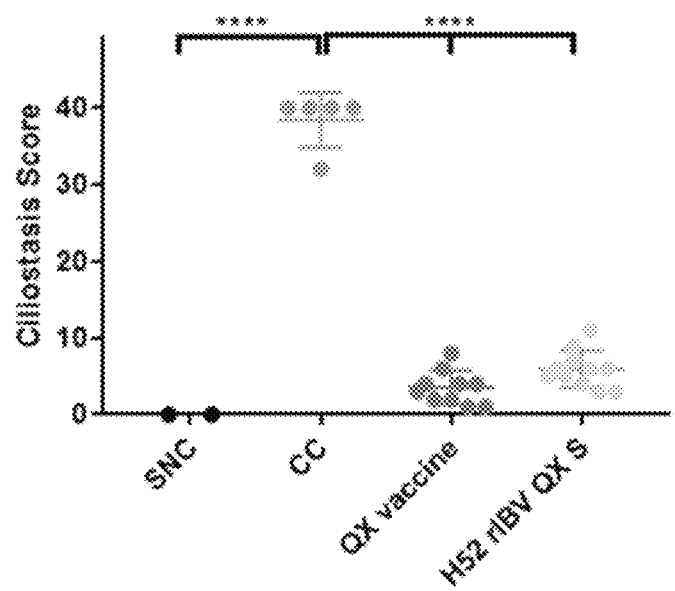
FIG. 5. Summary of ciliostasis scoring. The sum of the 10 individual scores for the 10 rings of one animal is calculated and is represented by one dot in the graph. Maximum ciliostasis corresponds to a score of 40, while absence of ciliostasis is represented by a score of 0. Mean and significance are calculated using GraphPad Prism and an ordinary one-way ANOVA test ($p<0.0001$).

All animals of the strict negative control show normal cilia movement while 80% animals of the challenge control group are positive for ciliostasis. In contrast, 82% of the animals vaccinated with H52 rIBV CR88 S Ecto are protected. In addition, the viral load in kidneys and choanal swabs of animals vaccinated with H52 CR88 S Ecto is reduced compared to the challenge control (FIG. 3 and FIG. 4).

Further, it is analyzed if the recombinant IBV H52 encoding the spike of IBV QX is able to confer protection against challenge with a virulent D388 QX strain, considered as homologous challenge for the encoded IBV QX spike and as heterologous challenge considering the IBV H52 backbone. All chickens are observed daily for clinical signs. No clinical signs are recorded after vaccination or challenge. Back titrations for the vaccination with H52 rIBV QX S at 1-day of age determine a titer of $10^4$ $EID_{50}$/ml while the QX vaccines exceeds a titer of $10^5$ $EID_{50}$/ml (target $10^{4.3}$ $EID_{50}$/ml). The titer of $10^{4.83}$ $EID_{50}$/ml (target $10^{4.3}$ $EID_{50}$/ml) is determined for the D388 QX challenge virus applied at 21 days post vaccination, respectively. Ciliostasis is scored as described above and results are depicted in Error! Reference source not found.5 and summarized in Table 5 Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0).

TABLE 7

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). An animal is considered not affected if not fewer than 9 out of 10 rings show normal ciliar activity.

| Group | Vaccine | Challenge | Mean Ciliostasis Score | Not affected [%] |
|---|---|---|---|---|
| 1 | — | — | 0 | 100 |
| 2 | — | D388 QX | 38.4 | 0 |
| 3 | QX vaccine | D388 QX | 3.5 | 100 |
| 3 | H52 rIBV QX S | D388 QX | 5.9 | 100 |

All animals of the strict negative control show normal cilia movement while all animals of the challenge control group are positive for ciliostasis. In contrast, 100% of the animals vaccinated with H52 rIBV QX S or the QX vaccine are protected.

Similar results are obtained with the other H52 rIBV with heterologous spikes or spike ectodomains.

The results highlight the suitability of IBV 4/91 strains as a potent backbones for the generation of recombinant IBV with heterologous spike and show excellent results, in particular, when compared to prior art data for the IBV Beaudette backbone.

The invention claimed is:

1. A recombinant, infectious bronchitis virus (IBV) comprising an H52 IBV backbone having at least 95% sequence identity to SEQ ID NO: 78 and a heterologous IBV spike protein (S protein) or fragment thereof,
   wherein the heterologous IBV S protein is from a different genotype or serotype than the H52 IBV and replaces the homologous H52 IBV S protein or fragment thereof,
   wherein the heterologous IBV S protein or fragment thereof is of a non-Massachusetts genotype or serotype,
   wherein the heterologous IBV S protein or fragment thereof comprises an amino acid sequence having at least 90% sequence identity to at least one of SEQ ID NOs: 5, 6, 9, 10, 11, 12, 13, 14, 15, or 16 or wherein the heterologous IBV S protein or fragment thereof comprises an amino acid sequence having at least 99% sequence identity to SEQ ID NO: 7 or 8, and
   wherein the heterologous IBV S protein or fragment thereof has a length of at least 1000 amino acids.

2. The IBV of claim 1, wherein the heterologous IBV S protein or fragment thereof is from an IBV with a genotype or serotype selected from: 4/91, QX, Q1, Arkansas, Variant 2, and Brazil.

3. The IBV of claim 1, wherein the heterologous IBV S protein or fragment thereof is from an IBV with a genotype or serotype selected from: 4/91 and QX.

4. The IBV of claim 1, wherein the heterologous IBV S protein or fragment thereof comprises an amino acid sequence having at least 90% sequence identity to at least one of SEQ ID NOs: 5 or SEQ ID NO: 6 or wherein the heterologous IBV S protein or fragment thereof comprises an amino acid sequence having at least 99% sequence identity to SEQ ID NO: 7 or 8.

5. A method for immunizing a subject, comprising:
   administering to the subject an immunogenic composition comprising a recombinant IBV comprising an H52 IBV backbone having at least 95% sequence identity to SEQ ID NO: 78 and a heterologous IBV S protein or fragment thereof,
   wherein the heterologous IBV S protein is from a different genotype or serotype than the H52 IBV and replaces the homologous H52 IBV S protein or fragment thereof,
   wherein the heterologous IBV S protein or fragment thereof is of a non-Massachusetts genotype or serotype,
   wherein the heterologous IBV S protein or fragment thereof comprises an amino acid sequence having at least 90% sequence identity to at least one of SEQ ID NOs: 5, 6, 9, 10, 11, 12, 13, 14, 15, or 16 wherein the heterologous IBV S protein or fragment thereof comprises an amino acid sequence having at least 99% sequence identity to SEQ ID NO: 7 or 8, and
   wherein the heterologous IBV S protein or fragment thereof has a length of at least 1000 amino acids.

6. The method of claim 5, wherein a protective immune response effective to reduce or eliminate subsequent IBV-infection clinical signs in the subject, relative to a non-vaccinated control subject of the same species, is elicited by administration of the immunogenic composition.

7. The method of claim 5, wherein a protective immune response effective to reduce ciliostasis risk in the subject, relative to a non-vaccinated control subject of the same species, is elicited by administration of the immunogenic composition.

8. The method of claim 5, wherein the subject is a poultry.

9. The method of claim 5, wherein the method is effective to prevent or reduce ciliostasis, rales, egg drop, kidney lesions, watery diarrhea, weight loss, viral load, and/or viral shedding in the subject relative to a non-vaccinated control subject of the same species if the subject is subsequently infected with IBV.

10. The method of claim 5, wherein the heterologous IBV S protein or fragment thereof is from an IBV with a genotype or serotype selected from the group consisting of: 4/91 and QX, and wherein administration of the immunogenic composition to an animal results in 82-100% protection against challenge with a spike-homologous challenge strain.

11. An immunogenic composition comprising a recombinant IBV comprising an H52 IBV backbone having at least 95% sequence identity to SEQ ID NO: 78 and a heterologous IBV S protein or fragment thereof,
 wherein the heterologous IBV S protein is from a different genotype or serotype than the H52 IBV and replaces the homologous H52 IBV S protein or fragment thereof, and
 wherein the heterologous IBV S protein or fragment thereof is of a non-Massachusetts genotype or serotype, and
 wherein the heterologous IBV S protein or fragment thereof comprises an amino acid sequence having at least 90% sequence identity to at least one of SEQ ID NOs: 5, 6, 9, 10, 11, 12, 13, 14, 15, or 16 or wherein the heterologous IBV S protein or fragment thereof comprises an amino acid sequence having at least 99% sequence identity to SEQ ID NO: 7 or 8
 wherein the heterologous IBV S protein or fragment thereof has a length of at least 1000 amino acids.

12. The immunogenic composition of claim 11, wherein the heterologous IBV S protein or fragment thereof is from an IBV with a genotype or serotype selected from: 4/91, QX, Q1, Arkansas, Variant 2, and Brazil.

13. The immunogenic composition of claim 12, wherein the heterologous IBV S protein or fragment thereof is from an IBV with a genotype or serotype selected from: 4/91 and QX.

14. The immunogenic composition of claim 11, wherein the immunogenic composition is a vaccine.

15. The immunogenic composition of claim 11, wherein the immunogenic composition is part of a kit.

16. The immunogenic composition of claim 11, wherein the heterologous IBV S protein or fragment thereof comprises an amino acid sequence having at least 90% sequence identity to at least one of SEQ ID NOs: 5 or SEQ ID NO: 6 or wherein the heterologous IBV S protein or fragment thereof comprises an amino acid sequence having at least 99% sequence identity to SEQ ID NO: 7 or 8.

17. The immunogenic composition of claim 11, wherein the heterologous IBV S protein or fragment thereof is from an IBV with a genotype or serotype selected from the group consisting of: 4/91 and QX, and wherein administration of the immunogenic composition to an animal results in 82-100% protection against challenge with a spike-homologous challenge strain.

18. A recombinant, infectious bronchitis virus (IBV) comprising an H52 IBV backbone and a heterologous IBV spike protein (S protein) or fragment thereof,
 wherein the heterologous IBV S protein is from a different genotype or serotype than the H52 IBV and replaces the homologous H52 IBV S protein or fragment thereof,
 wherein the heterologous IBV S protein or fragment thereof is of a non-Massachusetts genotype or serotype,
 wherein the heterologous IBV S protein or fragment thereof comprises an amino acid sequence having at least 90% sequence identity to at least one of SEQ ID NOs: 5, 6, 7, 8,
 wherein the heterologous IBV S protein or fragment thereof has a length of at least 1000 amino acids,
 wherein the heterologous IBV S protein or fragment thereof is from an IBV with a genotype or serotype selected from the group consisting of 4/91 and QX, and
 wherein administration of the immunogenic composition to an animal results in 82-100% protection against challenge with a spike-homologous challenge strain.

* * * * *